(12) United States Patent
Schoenfisch et al.

(10) Patent No.: US 8,981,139 B2
(45) Date of Patent: Mar. 17, 2015

(54) TERTIARY S-NITROSOTHIOL-MODIFIED NITRIC_OXIDE-RELEASING XEROGELS AND METHODS OF USING THE SAME

(71) Applicant: The University of North Carolina at Chapel Hill, Chapel Hill, NC (US)

(72) Inventors: Mark Schoenfisch, Chapel Hill, NC (US); Daniel Riccio, Raleigh, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/975,995

(22) Filed: Aug. 26, 2013

(65) Prior Publication Data
US 2014/0017121 A1 Jan. 16, 2014

Related U.S. Application Data

(63) Continuation of application No. PCT/US2012/026972, filed on Feb. 28, 2012.

(60) Provisional application No. 61/565,694, filed on Dec. 1, 2011, provisional application No. 61/447,368, filed on Feb. 28, 2011.

(51) Int. Cl.
*C07F 7/08* (2006.01)
*A61L 2/18* (2006.01)
(Continued)

(52) U.S. Cl.
CPC ............... *A61L 2/18* (2013.01); *C07F 7/0874* (2013.01); *C07F 7/1836* (2013.01); *C08G 77/26* (2013.01); *C08G 77/28* (2013.01); *C07F 7/10* (2013.01)
USPC ...................................................... 556/419

(58) Field of Classification Search
USPC ............... 422/22; 556/419; 427/21; 424/724; 564/102
See application file for complete search history.

(56) References Cited

U.S. PATENT DOCUMENTS

| | | |
|---|---|---|
| 4,507,466 A | 3/1985 | Tomalia et al. |
| 4,558,120 A | 12/1985 | Tomalia et al. |

(Continued)

FOREIGN PATENT DOCUMENTS

| | | |
|---|---|---|
| EP | 0 805 678 B1 | 10/2003 |
| EP | 0 746 327 B1 | 4/2004 |

(Continued)

OTHER PUBLICATIONS

Amadeu et al., "Nitric Oxide Donor Improves Healing if Applied on Inflammatory and Proliferative Disease" *Journal of Surgical Research* 149: 84-93 (2008).

(Continued)

*Primary Examiner* — Sean E Conley
(74) *Attorney, Agent, or Firm* — Myers Bigel Sibley & Sajovec, P.A.

(57) ABSTRACT

Provided according to embodiments of the invention are novel tertiary alkyl thiol compounds and novel tertiary alkyl nitrosothiol compounds. Further provided according to embodiments of the invention are methods of forming a nitric oxide (NO)-releasing xerogel coating that include (a) co-condensing a sol precursor solution comprising at least one backbone alkoxysilane and at least one tertiary thiol alkoxysilane in a solvent to form a sol; (b) coating a substrate with the sol; (c) optionally, drying the sol to form the xerogel coating; and (d) contacting the xerogel coating with a nitrosating agent. Methods of using xerogel coatings are also included.

20 Claims, 11 Drawing Sheets

(51) Int. Cl.
  *C07F 7/18* (2006.01)
  *C08G 77/26* (2006.01)
  *C08G 77/28* (2006.01)
  *C07F 7/10* (2006.01)

(56) References Cited

U.S. PATENT DOCUMENTS

| | | |
|---|---|---|
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 4,985,023 A | 1/1991 | Blank et al. |
| 4,990,338 A | 2/1991 | Blank et al. |
| 5,035,892 A | 7/1991 | Blank et al. |
| 5,045,322 A | 9/1991 | Blank et al. |
| 5,061,487 A | 10/1991 | Blank et al. |
| 5,079,004 A | 1/1992 | Blank et al. |
| 5,380,758 A | 1/1995 | Stamler et al. |
| 5,405,919 A | 4/1995 | Keefer et al. |
| 5,418,301 A | 5/1995 | Hult et al. |
| 5,428,070 A | 6/1995 | Cooke et al. |
| 5,504,117 A | 4/1996 | Gorfine |
| 5,519,020 A | 5/1996 | Smith et al. |
| 5,525,357 A | 6/1996 | Keefer et al. |
| 5,574,068 A | 11/1996 | Stamler et al. |
| 5,593,876 A | 1/1997 | Stamler et al. |
| 5,599,984 A | 2/1997 | Bianchi et al. |
| 5,629,322 A | 5/1997 | Guthikonda et al. |
| 5,632,981 A | 5/1997 | Saavedra et al. |
| 5,650,442 A | 7/1997 | Mitchell et al. |
| 5,650,447 A | 7/1997 | Keefer et al. |
| 5,665,077 A | 9/1997 | Rosen et al. |
| 5,676,963 A | 10/1997 | Keefer et al. |
| 5,691,423 A | 11/1997 | Smith et al. |
| 5,693,676 A | 12/1997 | Gorfine |
| 5,700,830 A | 12/1997 | Korthuis et al. |
| 5,718,892 A | 2/1998 | Keefer et al. |
| 5,726,156 A | 3/1998 | Girten et al. |
| 5,750,573 A | 5/1998 | Bianchi et al. |
| 5,753,684 A | 5/1998 | Bianchi et al. |
| 5,760,001 A | 6/1998 | Girten et al. |
| 5,770,645 A | 6/1998 | Stamler et al. |
| 5,786,332 A | 7/1998 | Girten et al. |
| 5,789,447 A | 8/1998 | Wink, Jr. et al. |
| 5,797,887 A | 8/1998 | Rosen et al. |
| 5,810,010 A | 9/1998 | Anbar |
| 5,814,666 A | 9/1998 | Green et al. |
| 5,814,667 A | 9/1998 | Mitchell et al. |
| 5,821,261 A | 10/1998 | Durette et al. |
| 5,837,736 A | 11/1998 | Mitchell et al. |
| 5,840,759 A | 11/1998 | Mitchell et al. |
| 5,849,794 A | 12/1998 | Bianchi et al. |
| 5,852,058 A | 12/1998 | Cooke et al. |
| 5,854,289 A | 12/1998 | Bianchi et al. |
| 5,859,062 A | 1/1999 | Bianchi et al. |
| 5,861,168 A | 1/1999 | Cooke et al. |
| 5,863,890 A | 1/1999 | Stamler et al. |
| 5,891,459 A | 4/1999 | Cooke et al. |
| 5,891,472 A | 4/1999 | Russell |
| 5,910,316 A | 6/1999 | Keefer et al. |
| 5,932,538 A | 8/1999 | Garvey et al. |
| 5,958,427 A | 9/1999 | Salzman et al. |
| 5,961,466 A | 10/1999 | Anbar |
| 5,962,520 A | 10/1999 | Smith et al. |
| 5,994,294 A | 11/1999 | Garvey et al. |
| 5,994,444 A | 11/1999 | Trescony et al. |
| 5,999,843 A | 12/1999 | Anbar |
| 6,008,255 A | 12/1999 | Bianchi et al. |
| 6,022,900 A | 2/2000 | Bianchi et al. |
| 6,035,225 A | 3/2000 | Anbar |
| 6,043,358 A | 3/2000 | Caldwell et al. |
| 6,045,827 A | 4/2000 | Russell |
| 6,070,928 A | 6/2000 | Campbell |
| 6,087,479 A | 7/2000 | Stamler et al. |
| 6,103,275 A | 8/2000 | Seitz et al. |
| 6,110,453 A | 8/2000 | Keefer et al. |
| 6,143,037 A | 11/2000 | Goldstein et al. |
| 6,147,068 A | 11/2000 | Smith et al. |
| 6,151,522 A | 11/2000 | Alfano et al. |
| 6,160,021 A | 12/2000 | Lerner et al. |
| 6,171,232 B1 | 1/2001 | Papandreou et al. |
| 6,174,539 B1 | 1/2001 | Stamler et al. |
| 6,180,082 B1 | 1/2001 | Woltering et al. |
| 6,180,676 B1 | 1/2001 | Bianchi et al. |
| 6,190,704 B1 | 2/2001 | Murrell |
| 6,200,558 B1 | 3/2001 | Saavedra et al. |
| 6,207,855 B1 | 3/2001 | Toone et al. |
| 6,218,016 B1 | 4/2001 | Tedeschi et al. |
| 6,232,336 B1 | 5/2001 | Hrabie et al. |
| 6,232,434 B1 | 5/2001 | Stamler et al. |
| 6,238,683 B1 | 5/2001 | Burnett et al. |
| 6,248,787 B1 | 6/2001 | Bianchi et al. |
| 6,255,277 B1 | 7/2001 | Stamler et al. |
| 6,261,594 B1 | 7/2001 | Smith et al. |
| 6,270,779 B1 | 8/2001 | Fitzhugh et al. |
| 6,287,601 B1 | 9/2001 | Russell |
| 6,290,981 B1 | 9/2001 | Keefer et al. |
| 6,291,424 B1 | 9/2001 | Stamler et al. |
| 6,294,517 B1 | 9/2001 | Garvey et al. |
| 6,299,980 B1 | 10/2001 | Shah et al. |
| 6,323,211 B1 | 11/2001 | Garvey et al. |
| 6,350,467 B1 | 2/2002 | Demopoulos et al. |
| 6,352,709 B1 | 3/2002 | Stamler et al. |
| 6,358,536 B1 | 3/2002 | Thomas |
| 6,359,167 B2 | 3/2002 | Toone et al. |
| 6,359,182 B1 | 3/2002 | Stamler et al. |
| 6,369,071 B1 | 4/2002 | Haj-Yehia |
| 6,372,733 B1 | 4/2002 | Caldwell et al. |
| 6,377,321 B1 | 4/2002 | Khan et al. |
| 6,379,660 B1 | 4/2002 | Saavedra et al. |
| 6,379,691 B1 | 4/2002 | Tedeschi et al. |
| 6,391,895 B1 | 5/2002 | Towart et al. |
| 6,403,759 B2 | 6/2002 | Stamler et al. |
| 6,410,622 B1 | 6/2002 | Endres |
| 6,417,162 B1 | 7/2002 | Garvey et al. |
| 6,432,077 B1 | 8/2002 | Stenzler |
| 6,433,182 B1 | 8/2002 | Garvey et al. |
| 6,436,975 B1 | 8/2002 | Del Soldato |
| 6,441,254 B1 | 8/2002 | Dobert |
| 6,448,267 B1 | 9/2002 | Anggard et al. |
| 6,451,337 B1 | 9/2002 | Smith et al. |
| 6,455,542 B1 | 9/2002 | Anggard et al. |
| 6,469,065 B1 | 10/2002 | Garvey et al. |
| 6,471,978 B1 | 10/2002 | Stamler et al. |
| 6,472,390 B1 | 10/2002 | Stamler et al. |
| 6,488,951 B2 | 12/2002 | Toone et al. |
| 6,492,405 B2 | 12/2002 | Haj-Yehia |
| 6,511,991 B2 | 1/2003 | Hrabie et al. |
| 6,514,934 B1 | 2/2003 | Garvey et al. |
| 6,538,033 B2 | 3/2003 | Bing |
| 6,560,478 B1 | 5/2003 | Alfano et al. |
| 6,562,344 B1 | 5/2003 | Stamler et al. |
| 6,562,785 B1 | 5/2003 | Shapiro |
| 6,583,113 B2 | 6/2003 | Stamler et al. |
| 6,583,311 B2 | 6/2003 | Toone et al. |
| 6,605,447 B2 | 8/2003 | Weiss et al. |
| 6,610,660 B1 | 8/2003 | Saavedra et al. |
| 6,627,602 B2 | 9/2003 | Stamler et al. |
| 6,642,208 B2 | 11/2003 | Cooke et al. |
| 6,642,260 B2 | 11/2003 | Haj-Yehia |
| 6,645,518 B2 | 11/2003 | Tedeschi et al. |
| 6,646,006 B2 | 11/2003 | Cooke et al. |
| 6,656,217 B1 | 12/2003 | Herzog, Jr. et al. |
| 6,673,338 B1 | 1/2004 | Arnold et al. |
| 6,673,891 B2 | 1/2004 | Stamler et al. |
| 6,699,846 B2 | 3/2004 | Elliott et al. |
| 6,703,046 B2 | 3/2004 | Fitzhugh et al. |
| 6,706,274 B2 | 3/2004 | Hermann et al. |
| 6,709,681 B2 | 3/2004 | Benjamin et al. |
| 6,723,703 B2 | 4/2004 | Gaston et al. |

(56) References Cited

U.S. PATENT DOCUMENTS

| | | |
|---|---|---|
| 6,737,447 B1 | 5/2004 | Smith et al. |
| 6,747,062 B2 | 6/2004 | Murrell |
| 6,750,254 B2 | 6/2004 | Hrabie et al. |
| 6,758,214 B2 | 7/2004 | Fine et al. |
| 6,759,430 B2 | 7/2004 | Anggard et al. |
| 6,780,849 B2 | 8/2004 | Herrmann et al. |
| 6,793,644 B2 | 9/2004 | Stenzler |
| 6,796,966 B2 | 9/2004 | Thomas |
| 6,841,166 B1 | 1/2005 | Zhang et al. |
| 6,855,366 B2 | 2/2005 | Smith et al. |
| 6,875,840 B2 | 4/2005 | Stamler et al. |
| 6,887,485 B2 | 5/2005 | Fitzhugh et al. |
| 6,887,994 B2 | 5/2005 | Stamler et al. |
| 6,894,073 B2 | 5/2005 | Lee et al. |
| 6,896,899 B2 | 5/2005 | Demopolos et al. |
| 6,897,218 B2 | 5/2005 | Casella et al. |
| 6,911,433 B2 | 6/2005 | Saavedra et al. |
| 6,911,478 B2 | 6/2005 | Hrabie et al. |
| 6,946,484 B2 | 9/2005 | Adams et al. |
| 6,949,530 B2 | 9/2005 | Hrabie et al. |
| 6,951,902 B2 | 10/2005 | McDonald et al. |
| 6,964,984 B2 | 11/2005 | Stamler et al. |
| 6,974,801 B2 | 12/2005 | Honda et al. |
| 7,012,098 B2 | 3/2006 | Manning et al. |
| 7,015,347 B2 | 3/2006 | Toone et al. |
| 7,025,869 B2 | 4/2006 | Fine et al. |
| 7,030,238 B2 | 4/2006 | Stamler et al. |
| 7,033,999 B2 | 4/2006 | Stamler et al. |
| 7,040,313 B2 | 5/2006 | Fine et al. |
| 7,048,951 B1 | 5/2006 | Seitz et al. |
| 7,049,308 B2 | 5/2006 | Stamler et al. |
| 7,052,711 B2 | 5/2006 | West et al. |
| 7,070,798 B1 | 7/2006 | Michal et al. |
| 7,081,524 B2 | 7/2006 | Saavedra et al. |
| 7,087,588 B2 | 8/2006 | Del Soldato |
| 7,087,709 B2 | 8/2006 | Stamler et al. |
| 7,122,018 B2 | 10/2006 | Stenzler et al. |
| 7,122,027 B2 | 10/2006 | Trescony et al. |
| 7,122,529 B2 | 10/2006 | Ruane et al. |
| 7,128,904 B2 | 10/2006 | Batchelor et al. |
| 7,135,189 B2 | 11/2006 | Knapp |
| 7,135,498 B1 | 11/2006 | Chopp et al. |
| 7,157,500 B2 | 1/2007 | Stamler et al. |
| 7,169,809 B2 | 1/2007 | Berthelette et al. |
| 7,176,237 B2 | 2/2007 | Honda et al. |
| 7,179,475 B1 | 2/2007 | Burnett et al. |
| 7,189,761 B2 | 3/2007 | Gorfine |
| 7,199,154 B2 | 4/2007 | Berthelette et al. |
| 7,204,980 B2 | 4/2007 | Clark |
| 7,226,586 B2 | 6/2007 | Fitzhugh et al. |
| 7,234,079 B2 | 6/2007 | Cheng |
| 7,259,250 B2 | 8/2007 | Stamler et al. |
| 7,279,176 B1 | 10/2007 | West et al. |
| 7,282,519 B2 | 10/2007 | Garvey et al. |
| 7,314,857 B2 | 1/2008 | Madhyastha |
| 7,335,383 B2 | 2/2008 | Meyerhoff et al. |
| 7,345,053 B2 | 3/2008 | Garvey |
| 7,348,319 B2 | 3/2008 | Hrabie et al. |
| 7,364,585 B2 | 4/2008 | Weber |
| 7,396,829 B2 | 7/2008 | Garvey et al. |
| 7,417,109 B2 | 8/2008 | Stamler et al. |
| 7,425,218 B2 | 9/2008 | Keefer et al. |
| 7,432,301 B2 | 10/2008 | Gaston et al. |
| 7,452,916 B2 | 11/2008 | Cooke |
| 7,468,435 B2 | 12/2008 | Waterhouse et al. |
| 7,485,324 B2 | 2/2009 | Miller et al. |
| 7,520,866 B2 | 4/2009 | Stenzler et al. |
| 7,531,164 B2 | 5/2009 | Daaka et al. |
| 7,569,559 B2 | 8/2009 | Arnold et al. |
| 7,582,623 B2 | 9/2009 | Mascharak |
| 7,595,313 B2 | 9/2009 | Garvey et al. |
| 7,622,501 B2 | 11/2009 | Dufresne et al. |
| 7,622,502 B2 | 11/2009 | Berthelette et al. |
| 7,645,748 B2 | 1/2010 | Orchansky et al. |
| 7,645,749 B2 | 1/2010 | Orchansky et al. |
| 7,651,697 B2 | 1/2010 | West et al. |
| 7,655,423 B2 | 2/2010 | Chopp et al. |
| 7,678,391 B2 | 3/2010 | Graham et al. |
| 7,678,830 B2 | 3/2010 | Honda et al. |
| 7,696,247 B2 | 4/2010 | Herrmann et al. |
| 7,745,656 B2 | 6/2010 | Toone et al. |
| 7,763,283 B2 | 7/2010 | Batchelor et al. |
| 7,785,616 B2 | 8/2010 | Stamler et al. |
| 7,795,286 B2 | 9/2010 | Lucet-Levannier |
| 7,799,335 B2 | 9/2010 | Herrmann et al. |
| 7,807,716 B2 | 10/2010 | Farber |
| 7,811,600 B2 | 10/2010 | Cheng et al. |
| 7,820,284 B2 | 10/2010 | Terry |
| 7,829,553 B2 | 11/2010 | Arnold et al. |
| 7,838,023 B2 | 11/2010 | Garvey et al. |
| 7,846,400 B2 | 12/2010 | Hyde et al. |
| 7,862,598 B2 | 1/2011 | Hyde et al. |
| 7,892,198 B2 | 2/2011 | Stenzler |
| 7,897,399 B2 | 3/2011 | Hyde et al. |
| 7,928,079 B2 | 4/2011 | Hrabie et al. |
| 7,928,096 B2 | 4/2011 | Waterhouse et al. |
| 7,947,299 B2 | 5/2011 | Knapp |
| 7,972,137 B2 | 7/2011 | Rosen |
| 7,975,699 B2 | 7/2011 | Hyde et al. |
| 8,003,811 B2 | 8/2011 | Almirante |
| 8,017,074 B2 | 9/2011 | Arnold |
| 8,021,679 B2 | 9/2011 | Chen |
| 8,034,384 B2 | 10/2011 | Meyerhoff |
| 8,043,246 B2 | 10/2011 | Av-Gay et al. |
| 2001/0012851 A1 | 8/2001 | Lundy et al. |
| 2001/0025057 A1 | 9/2001 | Gorfine |
| 2001/0038832 A1 | 11/2001 | Bonavida et al. |
| 2001/0053772 A1 | 12/2001 | Bonavida et al. |
| 2002/0028851 A1 | 3/2002 | Bianchi et al. |
| 2002/0049157 A1 | 4/2002 | Wu et al. |
| 2002/0061879 A1 | 5/2002 | Garvey et al. |
| 2002/0068365 A1 | 6/2002 | Kuhrts |
| 2002/0090401 A1 | 7/2002 | Tucker et al. |
| 2002/0115586 A1 | 8/2002 | Enikolopov |
| 2002/0132234 A1 | 9/2002 | Moskowitz |
| 2002/0136763 A1 | 9/2002 | Demopolos et al. |
| 2002/0138051 A1 | 9/2002 | Hole et al. |
| 2002/0143007 A1 | 10/2002 | Garvey et al. |
| 2002/0143062 A1 | 10/2002 | Lopez-Berestein et al. |
| 2002/0155174 A1 | 10/2002 | Benjamin et al. |
| 2002/0161042 A1 | 10/2002 | Gorfine |
| 2003/0027844 A1 | 2/2003 | Soldato |
| 2003/0039697 A1 | 2/2003 | Zhao et al. |
| 2003/0050305 A1 | 3/2003 | Tejada |
| 2003/0072783 A1 | 4/2003 | Stamler et al. |
| 2003/0093143 A1 | 5/2003 | Zhao et al. |
| 2003/0134779 A1 | 7/2003 | Diarra et al. |
| 2003/0170674 A1 | 9/2003 | Moskowitz |
| 2003/0203915 A1 | 10/2003 | Fang et al. |
| 2003/0205234 A1 | 11/2003 | Bardach et al. |
| 2004/0009238 A1 | 1/2004 | Miller et al. |
| 2004/0013747 A1 | 1/2004 | Tucker et al. |
| 2004/0033480 A1 | 2/2004 | Wong |
| 2004/0037836 A1 | 2/2004 | Stamler et al. |
| 2004/0037897 A1 | 2/2004 | Benjamin et al. |
| 2004/0043068 A1 | 3/2004 | Tedeschi et al. |
| 2004/0076582 A1 | 4/2004 | Dimatteo et al. |
| 2004/0082659 A1 | 4/2004 | Cooke et al. |
| 2004/0105898 A1 | 6/2004 | Benjamin et al. |
| 2004/0110691 A1 | 6/2004 | Stamler |
| 2004/0131703 A1 | 7/2004 | Bach et al. |
| 2004/0143010 A1 | 7/2004 | Esteve-Soler et al. |
| 2004/0147598 A1 | 7/2004 | Haj-Yehia |
| 2004/0157936 A1 | 8/2004 | Burnett et al. |
| 2004/0228889 A1 | 11/2004 | Cals-Grierson |
| 2004/0254419 A1 | 12/2004 | Wang et al. |
| 2004/0265244 A1 | 12/2004 | Rosen |
| 2005/0036949 A1 | 2/2005 | Tucker et al. |
| 2005/0037093 A1 | 2/2005 | Benjamin |
| 2005/0054714 A1 | 3/2005 | Munoz et al. |
| 2005/0065161 A1 | 3/2005 | Garvey et al. |
| 2005/0069595 A1 | 3/2005 | Chen et al. |
| 2005/0074506 A1 | 4/2005 | Natan et al. |
| 2005/0079132 A1 | 4/2005 | Wang et al. |

(56) References Cited

U.S. PATENT DOCUMENTS

| | | |
|---|---|---|
| 2005/0080021 A1 | 4/2005 | Tucker et al. |
| 2005/0080024 A1 | 4/2005 | Tucker et al. |
| 2005/0131064 A1 | 6/2005 | Gaston et al. |
| 2005/0142217 A1 | 6/2005 | Adams et al. |
| 2005/0142218 A1 | 6/2005 | Tucker et al. |
| 2005/0152891 A1 | 7/2005 | Toone et al. |
| 2005/0165452 A1 | 7/2005 | Sigg et al. |
| 2005/0171006 A1 | 8/2005 | Bunting et al. |
| 2005/0171199 A1 | 8/2005 | Murrell |
| 2005/0187222 A1 | 8/2005 | Garvey et al. |
| 2005/0220838 A1 | 10/2005 | Zhao et al. |
| 2005/0249818 A1 | 11/2005 | Sawan et al. |
| 2005/0265958 A1 | 12/2005 | West et al. |
| 2005/0281867 A1 | 12/2005 | Kahn et al. |
| 2006/0008529 A1 | 1/2006 | Meyerhoff et al. |
| 2006/0009431 A1 | 1/2006 | Earl et al. |
| 2006/0035854 A1 | 2/2006 | Goldstein et al. |
| 2006/0039950 A1 | 2/2006 | Zhou et al. |
| 2006/0058363 A1 | 3/2006 | Wang et al. |
| 2006/0067909 A1 | 3/2006 | West et al. |
| 2006/0095120 A1 | 5/2006 | Hermann |
| 2006/0100159 A1 | 5/2006 | Stamler et al. |
| 2006/0142183 A1 | 6/2006 | Diarra et al. |
| 2006/0147553 A1 | 7/2006 | Miller et al. |
| 2006/0147904 A1 | 7/2006 | Wong |
| 2006/0159726 A1 | 7/2006 | Shell |
| 2006/0172018 A1 | 8/2006 | Fine et al. |
| 2006/0198831 A1 | 9/2006 | Stamler et al. |
| 2006/0211601 A1 | 9/2006 | Stamler et al. |
| 2006/0269620 A1 | 11/2006 | Morris et al. |
| 2006/0286158 A1 | 12/2006 | Calvert Murrell et al. |
| 2006/0286159 A1 | 12/2006 | Calvert Murrell et al. |
| 2007/0003538 A1 | 1/2007 | Madhyastha |
| 2007/0014686 A1 | 1/2007 | Arnold et al. |
| 2007/0014733 A1 | 1/2007 | O'Donnell et al. |
| 2007/0014828 A1 | 1/2007 | Fitzhugh et al. |
| 2007/0037821 A1 | 2/2007 | Garvey et al. |
| 2007/0048344 A1 | 3/2007 | Yahiaoui et al. |
| 2007/0053952 A1 | 3/2007 | Chen et al. |
| 2007/0053955 A1 | 3/2007 | Larson et al. |
| 2007/0053966 A1 | 3/2007 | Ang et al. |
| 2007/0059351 A1 | 3/2007 | Murrell et al. |
| 2007/0086954 A1 | 4/2007 | Miller |
| 2007/0087025 A1 | 4/2007 | Fitzhugh et al. |
| 2007/0088345 A1 | 4/2007 | Larson et al. |
| 2007/0089739 A1 | 4/2007 | Fine et al. |
| 2007/0116785 A1 | 5/2007 | Miller |
| 2007/0129690 A1 | 6/2007 | Rosenblatt et al. |
| 2007/0148136 A1 | 6/2007 | Whitlock |
| 2007/0154570 A1 | 7/2007 | Miller et al. |
| 2007/0166227 A1 | 7/2007 | Liu et al. |
| 2007/0172469 A1 | 7/2007 | Clark |
| 2007/0191377 A1 | 8/2007 | Worcel |
| 2007/0196327 A1 | 8/2007 | Kalivretenos et al. |
| 2007/0197543 A1 | 8/2007 | Esteve-Soler et al. |
| 2007/0202155 A1 | 8/2007 | Ang et al. |
| 2007/0203242 A1 | 8/2007 | Calton |
| 2007/0207179 A1 | 9/2007 | Andersen et al. |
| 2007/0219208 A1 | 9/2007 | Kalyanaraman et al. |
| 2007/0225250 A1 | 9/2007 | Brown |
| 2007/0239107 A1 | 10/2007 | Lundberg et al. |
| 2007/0243262 A1 | 10/2007 | Hurley et al. |
| 2007/0248676 A1 | 10/2007 | Stamler et al. |
| 2007/0264225 A1 | 11/2007 | Cheng et al. |
| 2007/0270348 A1 | 11/2007 | Kahn et al. |
| 2007/0275100 A1 | 11/2007 | Miller |
| 2008/0025972 A1 | 1/2008 | Daaka et al. |
| 2008/0039521 A1 | 2/2008 | Yasuda et al. |
| 2008/0045909 A1 | 2/2008 | Fossel |
| 2008/0069848 A1 | 3/2008 | Peters |
| 2008/0069863 A1 | 3/2008 | Peters |
| 2008/0069905 A1 | 3/2008 | Peters |
| 2008/0071206 A1 | 3/2008 | Peters |
| 2008/0089956 A1 | 4/2008 | Da et al. |
| 2008/0139450 A1 | 6/2008 | Madhyastha et al. |
| 2008/0145449 A1 | 6/2008 | Stamler |
| 2008/0171021 A1 | 7/2008 | Bach et al. |
| 2008/0171351 A1 | 7/2008 | Smith |
| 2008/0175881 A1 | 7/2008 | Ippoliti et al. |
| 2008/0182797 A1 | 7/2008 | Nudler et al. |
| 2008/0193385 A1 | 8/2008 | Maibach |
| 2008/0193566 A1 | 8/2008 | Miller et al. |
| 2008/0207491 A1 | 8/2008 | Diarra et al. |
| 2008/0207713 A1 | 8/2008 | Wang et al. |
| 2008/0214646 A1 | 9/2008 | Knaus et al. |
| 2008/0226751 A1 | 9/2008 | Tucker et al. |
| 2008/0241208 A1 | 10/2008 | Shanley et al. |
| 2008/0275093 A1 | 11/2008 | Garvey et al. |
| 2008/0280984 A1 | 11/2008 | Fossel |
| 2008/0286321 A1 | 11/2008 | Reneker et al. |
| 2008/0287861 A1 | 11/2008 | Stenzler et al. |
| 2008/0311163 A1 | 12/2008 | Peters |
| 2008/0317626 A1 | 12/2008 | Arnold et al. |
| 2008/0317679 A1 | 12/2008 | Tamarkin et al. |
| 2009/0004298 A1 | 1/2009 | Gaston et al. |
| 2009/0010989 A1 | 1/2009 | Peters |
| 2009/0018091 A1 | 1/2009 | Ellis et al. |
| 2009/0028966 A1 | 1/2009 | Chen et al. |
| 2009/0036491 A1 | 2/2009 | Tucker et al. |
| 2009/0042819 A1 | 2/2009 | Ellis et al. |
| 2009/0048219 A1 | 2/2009 | Garvey |
| 2009/0069449 A1 | 3/2009 | Smith et al. |
| 2009/0081279 A1 | 3/2009 | Jezek et al. |
| 2009/0088411 A1 | 4/2009 | Renzi et al. |
| 2009/0093510 A1 | 4/2009 | Clementi et al. |
| 2009/0098187 A1 | 4/2009 | Peters et al. |
| 2009/0108777 A1 | 4/2009 | Hyde et al. |
| 2009/0110612 A1 | 4/2009 | Hyde et al. |
| 2009/0110712 A1 | 4/2009 | Hyde et al. |
| 2009/0110933 A1 | 4/2009 | Hyde et al. |
| 2009/0110958 A1 | 4/2009 | Hyde et al. |
| 2009/0112055 A1 | 4/2009 | Hyde et al. |
| 2009/0112193 A1 | 4/2009 | Hyde et al. |
| 2009/0112197 A1 | 4/2009 | Hyde et al. |
| 2009/0118819 A1 | 5/2009 | Merz et al. |
| 2009/0123528 A1 | 5/2009 | Fossel |
| 2009/0131342 A1 | 5/2009 | Ellis |
| 2009/0136410 A1 | 5/2009 | Smith |
| 2009/0137683 A1 | 5/2009 | Yasuda et al. |
| 2009/0143417 A1 | 6/2009 | Smith et al. |
| 2009/0148482 A1 | 6/2009 | Peters |
| 2009/0186859 A1 | 7/2009 | Velázquez et al. |
| 2009/0191284 A1 | 7/2009 | Conoci et al. |
| 2009/0196930 A1 | 8/2009 | Surber et al. |
| 2009/0197964 A1 | 8/2009 | Summar et al. |
| 2009/0203653 A1 | 8/2009 | Garvey |
| 2009/0214618 A1 | 8/2009 | Schoenfisch et al. |
| 2009/0214624 A1 | 8/2009 | Smith et al. |
| 2009/0214674 A1 | 8/2009 | Barraud et al. |
| 2009/0215838 A1 | 8/2009 | Garvey et al. |
| 2009/0221536 A1 | 9/2009 | Fossel |
| 2009/0222088 A1 | 9/2009 | Chen et al. |
| 2009/0226504 A1 | 9/2009 | Peters |
| 2009/0232863 A1 | 9/2009 | Cheng et al. |
| 2009/0232868 A1 | 9/2009 | Chen et al. |
| 2009/0255536 A1 | 10/2009 | Av-Gay et al. |
| 2009/0263416 A1 | 10/2009 | Dawson et al. |
| 2009/0264398 A1 | 10/2009 | Bauer |
| 2009/0270509 A1 | 10/2009 | Arnold et al. |
| 2009/0287072 A1 | 11/2009 | Meyerhoff et al. |
| 2009/0297634 A1 | 12/2009 | Friedman et al. |
| 2009/0304815 A1 | 12/2009 | Cossu et al. |
| 2009/0317885 A1 | 12/2009 | Mascharak |
| 2010/0003338 A1 | 1/2010 | Hubbell et al. |
| 2010/0015253 A1 | 1/2010 | Benjamin |
| 2010/0016790 A1 | 1/2010 | Peters |
| 2010/0021506 A1 | 1/2010 | Jones |
| 2010/0040703 A1 | 2/2010 | Miller et al. |
| 2010/0062055 A1 | 3/2010 | Herrmann et al. |
| 2010/0076162 A1 | 3/2010 | Ameer et al. |
| 2010/0086530 A1 | 4/2010 | Martinov |
| 2010/0087370 A1 | 4/2010 | Jain et al. |
| 2010/0099729 A1 | 4/2010 | Almirante et al. |
| 2010/0112033 A1 | 5/2010 | Ganzarolli de Oliveira et al. |

(56) References Cited

U.S. PATENT DOCUMENTS

| | | |
|---|---|---|
| 2010/0112095 A1 | 5/2010 | Morris et al. |
| 2010/0129474 A1 | 5/2010 | Benjamin et al. |
| 2010/0152683 A1 | 6/2010 | Lindgren et al. |
| 2010/0159119 A1 | 6/2010 | Chen et al. |
| 2010/0166603 A1 | 7/2010 | Opie |
| 2010/0178319 A1 | 7/2010 | Lindgren et al. |
| 2010/0184992 A1 | 7/2010 | Toone et al. |
| 2010/0196517 A1 | 8/2010 | Fossel |
| 2010/0197702 A1 | 8/2010 | Hellberg et al. |
| 2010/0197802 A1 | 8/2010 | Jezek et al. |
| 2010/0209469 A1 | 8/2010 | Bezwada |
| 2010/0221308 A1 | 9/2010 | Madhyastha et al. |
| 2010/0233304 A1 | 9/2010 | Pan |
| 2010/0239512 A1 | 9/2010 | Morris et al. |
| 2010/0247611 A1 | 9/2010 | Balkus, Jr. et al. |
| 2010/0247680 A1 | 9/2010 | Szabo |
| 2010/0255062 A1 | 10/2010 | Kalivretenos et al. |
| 2010/0256755 A1 | 10/2010 | Chen et al. |
| 2010/0261930 A1 | 10/2010 | Honda et al. |
| 2010/0262238 A1 | 10/2010 | Chen et al. |
| 2010/0268149 A1 | 10/2010 | Av-Gay et al. |
| 2010/0276284 A1 | 11/2010 | Meyerhoff et al. |
| 2010/0280122 A1 | 11/2010 | Fossel |
| 2010/0285100 A1 | 11/2010 | Balkus, Jr. et al. |
| 2010/0303891 A1 | 12/2010 | Lee et al. |
| 2010/0311780 A1 | 12/2010 | Farber |
| 2010/0323036 A1 | 12/2010 | Fine |
| 2010/0324107 A1 | 12/2010 | Dos Santos et al. |
| 2010/0331542 A1 | 12/2010 | Smith |
| 2010/0331968 A1 | 12/2010 | Morris et al. |
| 2011/0008815 A1 | 1/2011 | Stamler et al. |
| 2011/0033437 A1 | 2/2011 | Smith et al. |
| 2011/0046182 A1 | 2/2011 | Gilmer et al. |
| 2011/0059036 A1 | 3/2011 | Arnold et al. |
| 2011/0059189 A1 | 3/2011 | Cisneros |
| 2011/0065783 A1 | 3/2011 | O'Donnell et al. |
| 2011/0070318 A1 | 3/2011 | Jezek et al. |
| 2011/0071168 A1 | 3/2011 | Chopp et al. |
| 2011/0076313 A1 | 3/2011 | Av-Gay et al. |
| 2011/0104240 A1 | 5/2011 | Jones et al. |
| 2011/0106000 A1 | 5/2011 | Jones et al. |

FOREIGN PATENT DOCUMENTS

| | | |
|---|---|---|
| EP | 0 724 436 B1 | 7/2004 |
| EP | 1 411 908 B1 | 5/2005 |
| EP | 1 163 528 B1 | 11/2005 |
| EP | 1 681 068 A1 | 7/2006 |
| EP | 1 690 532 A1 | 8/2006 |
| EP | 1 690 554 A1 | 8/2006 |
| EP | 1 690 557 A1 | 8/2006 |
| EP | 1 690 558 A1 | 8/2006 |
| EP | 1 700 611 A1 | 9/2006 |
| EP | 1 704 876 A1 | 9/2006 |
| EP | 1 704 877 A1 | 9/2006 |
| EP | 1 704 879 A1 | 9/2006 |
| EP | 1 707 224 A1 | 10/2006 |
| EP | 1 728 438 A1 | 12/2006 |
| EP | 1 731 176 A1 | 12/2006 |
| EP | 1 757 278 A1 | 2/2007 |
| EP | 1 764 119 A1 | 3/2007 |
| EP | 1 790 335 A1 | 5/2007 |
| EP | 1 861 130 B1 | 9/2008 |
| EP | 1 343 547 B1 | 4/2009 |
| EP | 1 871 433 B1 | 4/2009 |
| EP | 1 161 248 B1 | 5/2009 |
| EP | 1 846 058 B1 | 7/2009 |
| EP | 2 233 437 A1 | 9/2010 |
| WO | WO 95/07691 A1 | 3/1995 |
| WO | WO 95/10267 A1 | 4/1995 |
| WO | WO 95/12394 A1 | 5/1995 |
| WO | WO 95/19767 A1 | 7/1995 |
| WO | WO 95/22335 A1 | 8/1995 |
| WO | WO 95/32715 A1 | 12/1995 |
| WO | WO 96/08966 A1 | 3/1996 |
| WO | WO 96/13164 A1 | 5/1996 |
| WO | WO 96/14844 A1 | 5/1996 |
| WO | WO 96/15781 A1 | 5/1996 |
| WO | WO 96/15797 A1 | 5/1996 |
| WO | WO 96/27386 A1 | 9/1996 |
| WO | WO 96/32118 A1 | 10/1996 |
| WO | WO 96/32136 A1 | 10/1996 |
| WO | WO 96/33757 A1 | 10/1996 |
| WO | WO 96/35416 A1 | 11/1996 |
| WO | WO 97/16983 A1 | 5/1997 |
| WO | WO 97/31654 A1 | 9/1997 |
| WO | WO 97/34014 A1 | 9/1997 |
| WO | WO 97/47254 A1 | 12/1997 |
| WO | WO 98/05689 A1 | 2/1998 |
| WO | WO 98/06389 A1 | 2/1998 |
| WO | WO 98/08482 A2 | 3/1998 |
| WO | WO 98/08482 A3 | 3/1998 |
| WO | WO 98/08496 A1 | 3/1998 |
| WO | WO 98/13358 A1 | 4/1998 |
| WO | WO 98/19996 A1 | 5/1998 |
| WO | WO 98/20015 A1 | 5/1998 |
| WO | WO 98/22090 A1 | 5/1998 |
| WO | WO 98/29101 A1 | 7/1998 |
| WO | WO 98/42661 A1 | 10/1998 |
| WO | WO 99/00070 A1 | 1/1999 |
| WO | WO 99/01427 A2 | 1/1999 |
| WO | WO 99/18949 A1 | 4/1999 |
| WO | WO 99/22729 A1 | 5/1999 |
| WO | WO 99/33823 A1 | 7/1999 |
| WO | WO 99/37616 A1 | 7/1999 |
| WO | WO 99/44595 A2 | 9/1999 |
| WO | WO 99/44595 A3 | 9/1999 |
| WO | WO 99/51221 A1 | 10/1999 |
| WO | WO 99/67210 A1 | 12/1999 |
| WO | WO 99/67296 A1 | 12/1999 |
| WO | WO 00/03640 A1 | 1/2000 |
| WO | WO 00/06151 A1 | 2/2000 |
| WO | WO 00/30658 A1 | 6/2000 |
| WO | WO 00/33877 A1 | 6/2000 |
| WO | WO 00/56333 A1 | 9/2000 |
| WO | WO 00/59304 A1 | 10/2000 |
| WO | WO 00/76318 A1 | 12/2000 |
| WO | WO 01/12067 A1 | 2/2001 |
| WO | WO 01/15738 A2 | 3/2001 |
| WO | WO 01/15738 A3 | 3/2001 |
| WO | WO 01/26702 A2 | 4/2001 |
| WO | WO 01/26702 A3 | 4/2001 |
| WO | WO 01/45732 A2 | 6/2001 |
| WO | WO 01/45732 A3 | 6/2001 |
| WO | WO 01/70199 A1 | 9/2001 |
| WO | WO 01/85227 A2 | 11/2001 |
| WO | WO 01/85227 A3 | 11/2001 |
| WO | WO 01/89572 A1 | 11/2001 |
| WO | WO 02/17880 A2 | 3/2002 |
| WO | WO 02/17880 A3 | 3/2002 |
| WO | WO 02/17881 A2 | 3/2002 |
| WO | WO 02/17881 A3 | 3/2002 |
| WO | WO 02/20026 A2 | 3/2002 |
| WO | WO 02/20026 A3 | 3/2002 |
| WO | WO 02/32418 A1 | 4/2002 |
| WO | WO 02/34705 A2 | 5/2002 |
| WO | WO 02/43786 A2 | 6/2002 |
| WO | WO 02/43786 A3 | 6/2002 |
| WO | WO 02/47675 A1 | 6/2002 |
| WO | WO 02/051353 A2 | 7/2002 |
| WO | WO 02/051353 A3 | 7/2002 |
| WO | WO 02/056864 A2 | 7/2002 |
| WO | WO 02/056864 A3 | 7/2002 |
| WO | WO 02/056874 A2 | 7/2002 |
| WO | WO 02/056904 A1 | 7/2002 |
| WO | WO 02/070496 A1 | 9/2002 |
| WO | WO 02/076395 A2 | 10/2002 |
| WO | WO 02/076395 A3 | 10/2002 |
| WO | WO 03/004097 A1 | 1/2003 |
| WO | WO 03/006427 A1 | 1/2003 |
| WO | WO 03/015605 A2 | 2/2003 |
| WO | WO 03/015605 A3 | 2/2003 |
| WO | WO 03/017989 A1 | 3/2003 |

(56) References Cited

FOREIGN PATENT DOCUMENTS

| | | | |
|---|---|---|---|
| WO | WO 03/026717 | A1 | 4/2003 |
| WO | WO 03/030659 | A1 | 4/2003 |
| WO | WO 03/041713 | A1 | 5/2003 |
| WO | WO 03/047636 | A2 | 6/2003 |
| WO | WO 03/047636 | A3 | 6/2003 |
| WO | WO 03/080039 | A1 | 10/2003 |
| WO | WO 03/092763 | A1 | 11/2003 |
| WO | WO 03/095398 | A2 | 11/2003 |
| WO | WO 03/095398 | A3 | 11/2003 |
| WO | WO 2004/009066 | A1 | 1/2004 |
| WO | WO 2004/009253 | A1 | 1/2004 |
| WO | WO 2004/011421 | A1 | 2/2004 |
| WO | WO 2004/012874 | A1 | 2/2004 |
| WO | WO 2004/037798 | A1 | 5/2004 |
| WO | WO 2004/039313 | A2 | 5/2004 |
| WO | WO 2004/039313 | A3 | 5/2004 |
| WO | WO 2004/060283 | A2 | 7/2004 |
| WO | WO 2004/064767 | A2 | 8/2004 |
| WO | WO 2004/064767 | A3 | 8/2004 |
| WO | WO 2004/087212 | A2 | 10/2004 |
| WO | WO 2004/098538 | A2 | 11/2004 |
| WO | WO 2004/098538 | A3 | 11/2004 |
| WO | WO 2005/003032 | A1 | 1/2005 |
| WO | WO 2005/011575 | A2 | 2/2005 |
| WO | WO 2005/011575 | A3 | 2/2005 |
| WO | WO 2005/030118 | A2 | 4/2005 |
| WO | WO 2005/030118 | A3 | 4/2005 |
| WO | WO 2005/030135 | A2 | 4/2005 |
| WO | WO 2005/030135 | A3 | 4/2005 |
| WO | WO 2005/030147 | A2 | 4/2005 |
| WO | WO 2005/030147 | A3 | 4/2005 |
| WO | WO 2005/034860 | A2 | 4/2005 |
| WO | WO 2005/034860 | A3 | 4/2005 |
| WO | WO 2005/039664 | A2 | 5/2005 |
| WO | WO 2005/039664 | A3 | 5/2005 |
| WO | WO 2005/067986 | A1 | 7/2005 |
| WO | WO 2005/070006 | A2 | 8/2005 |
| WO | WO 2005/070006 | A3 | 8/2005 |
| WO | WO 2005/070008 | A2 | 8/2005 |
| WO | WO 2005/070008 | A3 | 8/2005 |
| WO | WO 2005/070874 | A1 | 8/2005 |
| WO | WO 2005/070883 | A1 | 8/2005 |
| WO | WO 2005/072819 | A1 | 8/2005 |
| WO | WO 2005/077962 | A2 | 8/2005 |
| WO | WO 2005/077962 | A3 | 8/2005 |
| WO | WO 2005/081752 | A2 | 9/2005 |
| WO | WO 2005/081752 | A3 | 9/2005 |
| WO | WO 2005/081964 | A2 | 9/2005 |
| WO | WO 2005/094913 | A1 | 10/2005 |
| WO | WO 2005/102282 | A1 | 11/2005 |
| WO | WO 2005/107384 | A2 | 11/2005 |
| WO | WO 2005/107384 | A3 | 11/2005 |
| WO | WO 2005/112954 | A1 | 12/2005 |
| WO | WO 2005/115440 | A2 | 12/2005 |
| WO | WO 2005/115440 | A3 | 12/2005 |
| WO | WO 2005/120493 | A1 | 12/2005 |
| WO | WO 2006/023693 | A2 | 3/2006 |
| WO | WO 2006/023693 | A3 | 3/2006 |
| WO | WO 2006/037105 | A2 | 4/2006 |
| WO | WO 2006/037105 | A3 | 4/2006 |
| WO | WO 2006/041855 | A2 | 4/2006 |
| WO | WO 2006/041855 | A3 | 4/2006 |
| WO | WO 2006/045639 | A1 | 5/2006 |
| WO | WO 2006/055542 | A2 | 5/2006 |
| WO | WO 2006/055542 | A3 | 5/2006 |
| WO | WO 2006/058318 | A2 | 6/2006 |
| WO | WO 2006/064056 | A2 | 6/2006 |
| WO | WO 2006/066362 | A1 | 6/2006 |
| WO | WO 2006/084909 | A1 | 8/2006 |
| WO | WO 2006/084910 | A2 | 8/2006 |
| WO | WO 2006/084911 | A2 | 8/2006 |
| WO | WO 2006/084912 | A1 | 8/2006 |
| WO | WO 2006/084913 | A2 | 8/2006 |
| WO | WO 2006/084914 | A2 | 8/2006 |
| WO | WO 2006/095193 | A2 | 9/2006 |
| WO | WO 2006/095193 | A3 | 9/2006 |
| WO | WO 2006/096572 | A1 | 9/2006 |
| WO | WO 2006/097348 | A1 | 9/2006 |
| WO | WO 2006/099058 | A2 | 9/2006 |
| WO | WO 2006/099058 | A3 | 9/2006 |
| WO | WO 2006/100154 | A1 | 9/2006 |
| WO | WO 2006/100155 | A1 | 9/2006 |
| WO | WO 2006/100156 | A2 | 9/2006 |
| WO | WO 2006/122960 | A1 | 11/2006 |
| WO | WO 2006/122961 | A1 | 11/2006 |
| WO | WO 2006/125016 | A1 | 11/2006 |
| WO | WO 2006/125262 | A1 | 11/2006 |
| WO | WO 2006/127591 | A2 | 11/2006 |
| WO | WO 2006/127591 | A3 | 11/2006 |
| WO | WO 2006/128121 | A2 | 11/2006 |
| WO | WO 2006/128742 | A2 | 12/2006 |
| WO | WO 2006/128742 | A3 | 12/2006 |
| WO | WO 2006/128743 | A1 | 12/2006 |
| WO | WO 2006/130982 | A1 | 12/2006 |
| WO | WO 2007/003028 | A1 | 1/2007 |
| WO | WO 2007/005910 | A2 | 1/2007 |
| WO | WO 2007/005910 | A3 | 1/2007 |
| WO | WO 2007/012165 | A1 | 2/2007 |
| WO | WO 2007/016677 | A2 | 2/2007 |
| WO | WO 2007/016677 | A3 | 2/2007 |
| WO | WO 2007/023005 | A1 | 3/2007 |
| WO | WO 2007/024501 | A2 | 3/2007 |
| WO | WO 2007/024501 | A3 | 3/2007 |
| WO | WO 2007/027859 | A1 | 3/2007 |
| WO | WO 2007/028657 | A1 | 3/2007 |
| WO | WO 2007/030266 | A2 | 3/2007 |
| WO | WO 2007/030266 | A3 | 3/2007 |
| WO | WO 2007/050379 | A2 | 5/2007 |
| WO | WO 2007/050379 | A3 | 5/2007 |
| WO | WO 2007/053292 | A2 | 5/2007 |
| WO | WO 2007/053578 | A2 | 5/2007 |
| WO | WO 2007/053578 | A3 | 5/2007 |
| WO | WO 2007/054373 | A1 | 5/2007 |
| WO | WO 2007/057763 | A2 | 5/2007 |
| WO | WO 2007/057763 | A3 | 5/2007 |
| WO | WO 2007/059311 | A2 | 5/2007 |
| WO | WO 2007/059311 | A3 | 5/2007 |
| WO | WO 2007/064895 | A2 | 6/2007 |
| WO | WO 2007/064895 | A3 | 6/2007 |
| WO | WO 2007/067477 | A1 | 6/2007 |
| WO | WO 2007/084533 | A2 | 7/2007 |
| WO | WO 2007/084533 | A3 | 7/2007 |
| WO | WO 2007/086884 | A2 | 8/2007 |
| WO | WO 2007/086884 | A3 | 8/2007 |
| WO | WO 2007/088050 | A2 | 8/2007 |
| WO | WO 2007/088050 | A3 | 8/2007 |
| WO | WO 2007/088123 | A2 | 8/2007 |
| WO | WO 2007/088123 | A3 | 8/2007 |
| WO | WO 2007/092284 | A2 | 8/2007 |
| WO | WO 2007/092284 | A3 | 8/2007 |
| WO | WO 2007/100910 | A2 | 9/2007 |
| WO | WO 2007/100910 | A3 | 9/2007 |
| WO | WO 2007/103190 | A2 | 9/2007 |
| WO | WO 2007/103190 | A3 | 9/2007 |
| WO | WO 2007/127725 | A2 | 11/2007 |
| WO | WO 2007/127725 | A3 | 11/2007 |
| WO | WO 2007/133922 | A2 | 11/2007 |
| WO | WO 2007/133922 | A3 | 11/2007 |
| WO | WO 2007/143185 | A2 | 12/2007 |
| WO | WO 2007/143185 | A3 | 12/2007 |
| WO | WO 2007/149437 | A1 | 12/2007 |
| WO | WO 2007/149520 | A2 | 12/2007 |
| WO | WO 2007/149520 | A3 | 12/2007 |
| WO | WO 2008/005313 | A2 | 1/2008 |
| WO | WO 2008/005313 | A3 | 1/2008 |
| WO | WO 2008/013633 | A2 | 1/2008 |
| WO | WO 2008/013633 | A3 | 1/2008 |
| WO | WO 2008/020218 | A1 | 2/2008 |
| WO | WO 2008/027203 | A2 | 3/2008 |
| WO | WO 2008/027203 | A3 | 3/2008 |
| WO | WO 2008/062160 | A1 | 5/2008 |
| WO | WO 2008/071242 | A1 | 6/2008 |
| WO | WO 2008/088507 | A2 | 7/2008 |
| WO | WO 2008/088507 | A3 | 7/2008 |

(56) References Cited

FOREIGN PATENT DOCUMENTS

| | | |
|---|---|---|
| WO | WO 2008/095841 A2 | 8/2008 |
| WO | WO 2008/095841 A3 | 8/2008 |
| WO | WO 2008/098192 A2 | 8/2008 |
| WO | WO 2008/098192 A3 | 8/2008 |
| WO | WO 2008/100591 A2 | 8/2008 |
| WO | WO 2008/100591 A3 | 8/2008 |
| WO | WO 2008/112391 A2 | 9/2008 |
| WO | WO 2008/112391 A3 | 9/2008 |
| WO | WO 2008/116497 A1 | 10/2008 |
| WO | WO 2008/116925 A1 | 10/2008 |
| WO | WO 2008/130567 A1 | 10/2008 |
| WO | WO 2008/141416 A1 | 11/2008 |
| WO | WO 2008/150505 A1 | 12/2008 |
| WO | WO 2008/157393 A1 | 12/2008 |
| WO | WO 2009/014616 A1 | 1/2009 |
| WO | WO 2009/014829 A2 | 1/2009 |
| WO | WO 2009/014829 A3 | 1/2009 |
| WO | WO 2009/019498 A2 | 2/2009 |
| WO | WO 2009/019498 A3 | 2/2009 |
| WO | WO 2009/019499 A2 | 2/2009 |
| WO | WO 2009/026680 A1 | 3/2009 |
| WO | WO 2009/036571 A1 | 3/2009 |
| WO | WO 2009/049208 A1 | 4/2009 |
| WO | WO 2009/064861 A2 | 5/2009 |
| WO | WO 2009/064861 A3 | 5/2009 |
| WO | WO 2009/073643 A2 | 6/2009 |
| WO | WO 2009/073643 A3 | 6/2009 |
| WO | WO 2009/073940 A2 | 6/2009 |
| WO | WO 2009/073940 A3 | 6/2009 |
| WO | WO 2009/080795 A1 | 7/2009 |
| WO | WO 2009/086470 A2 | 7/2009 |
| WO | WO 2009/086470 A3 | 7/2009 |
| WO | WO 2009/088433 A1 | 7/2009 |
| WO | WO 2009/098113 A1 | 8/2009 |
| WO | WO 2009/117182 A2 | 9/2009 |
| WO | WO 2009/117182 A3 | 9/2009 |
| WO | WO 2009/117183 A1 | 9/2009 |
| WO | WO 2009/124379 A1 | 10/2009 |
| WO | WO 2009/131931 A1 | 10/2009 |
| WO | WO 2009/155689 A1 | 12/2009 |
| WO | WO 2009/155690 A1 | 12/2009 |
| WO | WO 2010/002450 A2 | 1/2010 |
| WO | WO 2010/002450 A3 | 1/2010 |
| WO | WO 2010/033242 A2 | 3/2010 |
| WO | WO 2010/033242 A3 | 3/2010 |
| WO | WO 2010/045465 A1 | 4/2010 |
| WO | WO 2010/048724 A1 | 5/2010 |
| WO | WO 2010/080213 A2 | 7/2010 |
| WO | WO 2010/080213 A3 | 7/2010 |
| WO | WO 2010/096320 A2 | 8/2010 |
| WO | WO 2010/096320 A3 | 8/2010 |
| WO | WO 2010/114669 A1 | 10/2010 |
| WO | WO 2010/120414 A2 | 10/2010 |
| WO | WO 2010/151505 A1 | 12/2010 |
| WO | WO 2012/118819 A2 | 9/2012 |

OTHER PUBLICATIONS

Ashutosh, K. et al., "Use of nitric oxide inhalation in chronic obstructive pulmonary disease" *Thorax* 55:109-113 (2000).
Azizzadeh, B. et al., "Nitric Oxide Improve Cisplatin Cytotoxicity in Head and Neck Squamous Cell Carcinoma" *Laryngoscope* 111:1896-1900 (2001).
Barst, R.J. et al., "Clinical perspectives with long-term pulsed inhaled nitric oxide for the treatment of pulmonary arterial hypertension" *Pulmonary Circulation* 2(2):139-147 (2012).
Barraud, N., et al., "Involvement of Nitric Oxide in Biofilm Dispersal of Pseudomonas aeruginosa" *Journal of Bacteriology* 188(21):7344-7353 (2006).
Benz S. et al., "Effect of Nitric Oxide in Ischemia/Reperfusion of the Pancreas" *Journal of Surgical Research* 106(1):46-53, (2002).
Bian K. et al., "Vascular System: Role of Nitric Oxide in Cardiovascular Diseases" *The Journal of Clinical Hypertension* 10(4):304-310 (2008).

Bloch K.D. et al. "Inhaled NO as a therapeutic agent" *Cardiovascular Research* 75:339-348 (2007).
Bohl Masters et al., "Effects of nitric oxide releasing vinyl poly(vinyl alcohol) hydrogel dressings on dermal wound healing in diabetic mice" *Wound Repair and Regeneration* 10(5): 286-294 (2002).
Bonavida B. et al., "Novel therapeutic applications of nitric oxide donors in cancer: Roles in chemo- and immunosensitization to apoptosis and inhibition of metastases" *Nitric Oxide* (19) 2:152-157 (2008).
Bonavida B. et al., "Therapeutic potential of nitric oxide in cancer" *Drug Resistance Updates* 9(3):157-73 (2006).
Boykin J.V. et al., "HBO mediates increased nitric oxide production associated with wound healing", *Wound Repair and Regeneration* 12(2) (2004).
Boykin Jr. J.V., "Wound Nitric Oxide Bioactivity: A Promising Diagnostic Indicator for Diabetic Foot Ulcer Management", *Journal of Wound, Ostomy & Continence Nursing* 37(1):25-32 (2010).
Bruch-Gerharz D. et al., "Nitric Oxide in Human Skin: Current Status and Future Prospects", *Journal of Investigative Dermatology* 110:1-7 (1998).
Cals-Grierson M.M. et al., "Nitric oxide function in the skin", *Nitric Oxide* 10(4):179-193 (2004).
Carlsson S. et al., "Intravesical Nitric Oxide Delivery for Prevention of Catheter-Associated Urinary Tract Infections" *Antimicrobial Agents and Chemotherapy* 49(6):2352 (2005).
Coban, A., et al., "The Effect of Nitric Oxide Combined with Fluoroquinolones against *Salmonellaenterica* Serovar Typhimurium in Vitro," *Mem Inst Oswaldo Cruz*, Rio de Janeiro, 98(3):419-423 (2003).
De Groote M.A. et al., "NO Inhibitions: Antimicrobial Properties of Nitric Oxide", *Clinical Infectious Diseases* 21 (Supplement 2):S162-S165 (1995).
Fang F., "Mechanisms of Nitric Oxide-related Antimicrobial Activity" *Journal of Clinical Investigation* 99(12):2818-2825 (1997).
Frederiksen L.J. et al., "Chemosensitization of Cancer In vitro and In vivo by Nitric Oxide Signaling" *Clinical Cancer Research* 13:2199-2206 (2007).
Frost et al., "Synthesis, characterization, and controlled nitric oxide release from S-nitrosothiol-derivatized fumed silica polymer filler particles" *Journal of Biomedical Research, Part A*, 72A:409-419 (2005).
Ghaffari A. et al., "Potential application of gaseous nitric oxide as a topical antimicrobial agent" *Nitric Oxide* 14(1):21-29 (2006).
Gupta, R., et al., "Bioactive materials for biomedical applications using sol-gel technology," *Biomedical Materials* 3:1-15 (2008).
Herman A.G. et al., "Therapeutic potential of nitric oxide donors in the prevention and treatment of atherosclerosis" *European Heart Journal* 26:1945-1955 (2005).
Hetrick E.M. et al., "Bactericidal Efficacy of Nitric Oxide-Releasing Silica Nanoparticles" *ACS Nano* 2(2):235-246 (2008).
Hetrick et al., "Anti-biofilm efficacy of nitric oxide-releasing silica nanoparticles", *Biomaterials* 30:2782-2789 (2009).
Hirst D. et al., "Targeting nitric oxide for cancer therapy", *Journal of Pharmacy and Pharmacology* 59:3-13 (2007).
Howlin R. et al., "Nitric oxide-mediated dispersal and enhanced antibiotic sensitivity in *Pseudomonas aeruginosa* biofilms from the cystic fibrosis lung", *Archives of Disease In Childhood* 96:A45 (2011).
Hrabie et al., "Chemistry of the nitric oxide-releasing diazeniumdiolate ("nitrosohydroxylamine") functional group and its oxygen-substituted derivatives," *Chemical Reviews* 102:1135-1154 (2002).
Huerta S. et al., "Nitric oxide donors: Novel cancer therapeutics (Review)", *International Journal of Oncology* 33:909-927 (2008).
International Search Report and Written Opinion Corresponding to International Application No. PCT/US2012/26972; Date of Mailing: Feb. 28, 2012; 11 Pages.
International Search Report and Written Opinion Corresponding to International Application No. PCT/US2012/26960; Date of Mailing: Feb. 28, 2012; 18 Pages.
Iwakir, N. et al., Synthesis of Amphiphillic polysiloxanes and their properties for formation of nano-aggregates, *Colloid and Polymer Science* 287:577-582 (2009).

(56) References Cited

OTHER PUBLICATIONS

Johnson T. A. et al., "Reduced ischemia/reperfusion injury via glutathione-initiated nitric oxide-releasing dendrimers", *Nitric Oxide*, 2009, 7 Pages.

Jones M.L. et al., "Antimicrobial properties of nitric oxide and its application in antimicrobial formulations and medical devices", *Applied Microbiology and Biotechnology* 88:401-407 (2010).

Kiziltepe T. et al., "JS-K, a GST-activated nitric oxide generator, induces DNA double-strand breaks, activates DNA damage response pathways, and induces apoptosis in vitro and in vivo in human multiple myeloma cells", *Blood* 110:709-718 (2007).

Lamas S. et al., "Nitric oxide signaling comes of age: 20 years and thriving", *Cardiovascular Research* 75:207-209 (2007).

Liu X. et al., "Nitric Oxide Inhalation Improves Microvascular Flow and Decreases Infarction Size After Myocardial Ischemia and Reperfusion", *Journal of the American College of Cardiology*, vol. 50, No. 8 (2007).

Luo J. et al., "Nitric oxide: a newly discovered function on wound healing", *Acta Pharmacologica Sinica* 26(3):259-264 (2005).

McElhaney-Feser, G., et al., "Synergy of Nitric Oxide and Azoles against *Candida* Species In Vitro," *Antimicrobial Agents and Chemotherapy* 42(9):2342-2346 (1998).

Mcgrowder D. et al., "Therapeutic Uses of Nitric Oxide-donating Drugs in the Treatment of Cardiovascular Diseases" *International Journal of Pharmacology* 2(4): 366-373 (2006).

Napoli C. et al., "Nitric oxide and atherosclerosis: An update", *Nitric Oxide* 15(4):265-279 (2006).

Phillips L. et al., "Nitric Oxide Mechanism of Protection in Ischemia and Reperfusion Injury", *Journal of Investigative Surgery* 22:46-55 (2009).

Riccio et al., "Nitric oxide-releasing S-nitrosothiol-modified xerogels" *Biomaterials* 30:4494-4502 (2009).

Robson, MC, "Wound Infection. A Failure of Wound Healing Caused by an Imbalance of Bacteria," *Surgical Clinics of North America* 77(3): 637-50 (1997).

Rothrock A.R. et al., "Synthesis of Nitric Oxide-Releasing Gold Nanoparticles", *Journal of American Chemical Society* 127:9362-9363 (2005).

Saaral, NY, "The Equilibrium Between Endothelin-1/Nitric Oxide in Acne Vulgaris," *Istanbul Tip Fakultesi Dergisi Cilt*, 2008, 71(4).

Saavedra J.E. et al., "Esterase-Sensitive Nitric Oxide Donors of the Diazeniumdiolate Family: In Vitro Antileukemic Activity" *Journal of Medicinal Chemistry* 43:261-269 (2000).

Schäffer M.R. et al., "Diabetes-impaired healing and reduced wound nitric oxide synthesis: A possible pathophysiologic correlation", *Surgery* 121(5):513-519 (1997).

Schairer D.O. et al., "The potential of nitric oxide releasing therapies as antimicrobial agents" *Virulence* 3(3):271-279 (2012).

Schulz R. et al., "Nitric oxide in myocardial ischemia/reperfusion injury", *Cardiovascular Research* 61:402-413 (2004).

Schwentker A. et al., "Nitric oxide and wound repair: role of cytokines?" *Nitric Oxide* 7(1):1-10 (2002).

Shin et al. "Synthesis of Nitric Oxide-Releasing Silica Nanoparticles" *Journal of American Chemical Society* 129(15):4612-4619 (2007).

Shin et al. "Supporting Information: Synthesis of Nitric Oxide-Releasing Silica Nanoparticles" *Journal of American Chemical Society* 129(15):S1-S4 (2007).

Simeone A.M. et al., "N-(4-Hydroxyphenyl) retinamide and nitric oxide pro-drugs exhibit apoptotic and anti-invasive effects against bone metastatic breast cancer cells" *Carcinogenesis* 27(3):568-577 (2006).

Siriussawakul A. et al. "Role of nitric oxide in hepatic ischemia-reperfusion injury", *World Journal of Gastroenterology* 16(48): 6079-6086 (2010).

Shi, HP, et al., "The role of iNOS in wound healing" *Surgery*, vol. 130(2):225-229 (2001).

Stasko, N., et al., "Dendrimers as a Scaffold for Nitric Oxide Release," *J. Am. Chem. Soc.*, 2006, vol. 128, pp. 8265-8271.

Stevens E.V. et al., "Nitric Oxide-Releasing Silica Nanoparticle Inhibition of Ovarian Cancer Cell Growth", *Molecular Pharmaceutics* 7(3):775-785 (2010).

Summersgill, J., et al., "Killing of Legionella pneumophila by nitric oxide in γ-interferon-activated macrophages," *Journal of Leukocyte Biology* 52:625-629 (1992).

Tang, X., et al., "Synthesis of Beta-Lactamase Activated Nitric Oxide Donors," *Biorgania & Medicinal Chemistry Letters* 13:1687-1690 (2003).

Sato et al. "Dynamic Aspect of Reactive Oxygen and Nitric Oxide in Oral Cavity", *J. Clin. Biochem. Nutr.* 42:8-13 (2008).

Slowing et al. "Mesoporous silica nanoparticles as controlled release drug delivery and gene transfection carriers" *Advanced Drug Delivery Reviews* 60:1278-1288 (2008).

Terpolilli N.A. et al., "Inhalation of Nitric Oxide Prevents Ischemic Brain Damage in Experimental Stroke by Selective Dilatation of Collateral Arterioles" *Circulation Research* 110:727-738 (2012).

Thomas D.D. et al., "Hypoxic inducible factor 1α, extracellular signal-regulated kinase, and p53 are regulated by distinct threshold concentrations of nitric oxide", *Proceedings of the National Academy of Sciences* 101(24):8894-8899 (2004).

Weller R. "Nitric oxide donors and the skin: useful therapeutic agents?" *Clinical Science* 105:533-535 (2003).

Wink D.A. et al., "The multifaceted roles of nitric oxide in cancer", *Carcinogenesis* 19(5):711-721 (1998).

Witte M.B. et al., "Nitric oxide enhances experimental wound healing in diabetes", *British Journal of Surgery* 89:1594-1601 (2002).

Witte M.B. et al., "Role of nitric oxide in wound repair", *The American Journal of Surgery* 183(4):406-412 (2002).

Yetik-Anacak G. et al., "Nitric oxide and the endothelium: History and impact on cardiovascular disease", *Vascular Pharmacology* 45(5):268-276 (2006).

Zhang H. et al., "Nitric Oxide-Releasing Fumed Silica Particles: Synthesis, Characterization, and Biomedical Application", *Journal of the American Chemical Society* 125:5015-5024 (2003).

Zhu, D., et al., "Corrosion protection of metals by water-based silane mixtures of bis-[trimethosysilylpropyl]amine and vinyltriacetoxysilane," *Progress in Organic Coatings* 49:42-53 (2004).

Zhu H. et al., "Effects of Nitric Oxide on Skin Burn Wound Healing", *Journal of Burn Care & Research* 29(5):804-814 (2008).

Zhu H. et al., "Nitric Oxide Accelerates the Recovery from Burn Wounds", *World Journal of Surgery* 31: 624-631 (2007).

European Search Report Corresponding to European Patent Application No. 09820905.9; Dated: Feb. 14, 2013; 7 Pages.

Living Water Acid-Alkaline Balance http://www.livingwaterhealthsolutions.com/Articles/alkalize.php Accessed online Nov. 3, 2011.

Salivary pH Testing https://allicincenter.com/pdf/ph_testinq.pdf Accessed online Nov. 3, 2011.

Al-Sa'Doni et al., "S-Nitrosothiols as Nitric Oxide-Donors: Chemistry, Biology and Possible Future Therapeutic Applications", *Current Medicinal Chemistry*, 2004, 11: 2679-2690.

Al-Sa'Doni et al., "Current Status and Future Possibilities of Nitric Oxide-Donor Drugs: Focus on *S*-Nitrosothiols", *Mini-Reviews in Medicinal Chemistry*, 2005, 5: 247-254.

Albert, Klaus, "NMR investigations of stationary phases", *Journal of Separation Science*, 2003, 26: 215-224.

Bainbrigge et al., "The thermal stability of S-nitrosothiols: experimental studies and ab initio calculations on model compounds", *Journal of the Chemical Society, Perkin Transactions*, 1997, 2: 351-353.

Bartberger et al., "Theory, Spectroscopy, and Crystallographic Analysis of *S*-Nitrosothiols: Conformational Distribution Dictates Spectroscopic Behavior", *Journal of the American Chemical Society*, 2000, 122: 5889-5890.

Bogush et al., "Preparation of Monodisperse Silica Particles: Control of Size and Mass Fraction", *Journal of Non-Crystalline Solids*, 1988, 104: 95-106.

Branda et al., "The effect of mixing alkoxides on the Stober particles size", *Colloids and Surfaces A: Physicochemical and Engineering Aspects*, 2007, 299: 252-255.

(56) References Cited

OTHER PUBLICATIONS

Brinker et al., *Sol-Gel Science: The Physics and Chemistry of Sol-Gel Processing*, Chapter 3, "Hydrolysis and Condensation II: Silicates", pp. 97-234, 1990.

Brinker et al., *Sol-Gel Science: The Physics and Chemistry of Sol-Gel Processing*, Chapter 4, "Particulate Sols and Gels", pp. 235-302, 1990.

Brinker et al., *Sol-Gel Science: The Physics and Chemistry of Sol-Gel Processing*, Chapter 8, "Drying", pp. 453-514, 1990.

Brinker et al., *Sol-Gel Science: The Physics and Chemistry of Sol-Gel Processing*, Chapter 9, "Structural Evolution During Consolidation", pp. 515-616, 1990.

Brinker et al., *Sol-Gel Science: The Physics and Chemistry of Sol-Gel Processing*, Chapter 10, "Surface Chemistry and Chemical Modification", pp. 617-674, 1990.

Brinker et al., *Sol-Gel Science: The Physics and Chemistry of Sol-Gel Processing*, Chapter 13, "Film Formation", pp. 787-838, 1990.

Brunner et al., "In Vitro Cytotoxicity of Oxide Nanoparticles: Comparison to Asbestos, Silica, and the Effect of Particle Solubility", *Environmental Science and Technology*, 2006, 40: 4374-4381.

Butler et al., "Chemistry, Analysis, and Biological Roles of S-Nitrosothiols", *Analytical Biochemistry*, 1997, 249: 1-9.

Cassidy et al., "Drug delivery strategies for photodynamic antimicrobial chemotherapy: From benchtop to clinical practice", *Journal Photochemistry and Photobiology B: Biology*, 2009, 95(2): 71-80. (Abstract Only).

Charville et al., "Reduced bacterial adhesion to fibrinogen-coated substrates via nitric oxide release", *Biomaterials*, 2008, 29(30): 4039-4044.

Coneski et al., "Degradable Nitric Oxide-Releasing Biomaterials via Post-Polymerization Functionalization of Cross-Linked Polyesters", *Biomacromolecules*, 2010, 11: 3208-3215.

Coneski et al., "Synthesis of nitric oxide-releasing polyurethanes with S-nitrosothiol-containing hard and soft segments", *Polymer Chemistry*, 2011, 2: 906-913.

Cooke, John, "NO and angiogenesis", *Atherosclerosis Supplements*, 2003, 4: 53-60.

Crichton et al., "Old Iron, Young Copper: from Mars to Venus", *BioMetals*, 2001, 14: 99-112.

De Souza et al., "Leishmanicidal activity of primary S-nitrosothiols against *Leishmania major* and *Leishmania amazonensis*: Implications for the treatment of cutaneous leishmaniasis", *Nitric Oxide*, 2006, 15: 209-216.

Deupree et al., "Morphological analysis of the antimicrobial action of nitric oxide on Gram-negative pathogens using atomic force microscopy", *Acta Biomaterialia*, 2009, 5:1405-1415.

Dicks et al., "Identification of $Cu^+$ as the effective reagent in nitric oxide formation from S-nitrosothiols (RSNO)", *Journal of the Chemical Society*, 1996, 2: 481-487.

Dobmeier et al., "Nitric Oxide-Releasing Xerogel-Based Fiber-Optic pH Sensors", *Analytical Chemistry*, 2006, 78: 7461-7466.

Etchenique et al., "Photodelivery of Nitric Oxide from a Nitrosothiol-Derivatized Surface", *Journal of the American Chemical Society*, 2000, 122: 3967-3968.

Foster et al., "Photocatalytic disinfection using titanium dioxide: spectrum and mechanism of antimicrobial activity", *Applied Microbiology Biotechnology*, 2011, 90(6): 1847-1868.

Frost et al., "Controlled Photoinitiated Release of Nitric Oxide from Polymer Films Containing S-Nitroso-N-acetyl-$_{DL}$penicillamine Derivatized Fumed Silica Filler", *Journal of the American Chemical Society*, 2004, 126: 1348-1349.

Frost et al., "Polymers incorporating nitric oxide releasing/generating substances for improved biocompatibility of blood-contacting medical devices", *Biomaterials*, 2005, 26(14): 1685-1695.

Garcia et al., "S-Nitroso-N-Acetylcysteine (SNAC) Prevents Myocardial Alterations in Hypercholesterolemic LDL Receptor Knockout Mice by Antiinflammatory Action", *Journal of Cardiovascular Pharmacology and Therapeutics*, 2008, 51: 78-85.

Gaslain et al., "One-step preparation of thiol-modified mesoporous silica spheres with various functionalization levels and different pore structures", *Journal of Sol-Gel Science and Technology*, 2009, 49: 112-124.

Grossi et al., "A Kinetic Study of S-Nitrosothiol Decomposition", *Chemistry—A European Journal*, 2002, 8(2): 380-387.

Hatton et al., "Past, Present, and Future of Periodic Mesoporous Organosilicas—The PMOs", *Accounts of Chemical Research*, 2005, 38: 305-312.

Hetrick et al., "Reducing implant-related infections; active release strategies", *Chemical Society Reviews*, 2006, 35: 780-789.

Hetrick et al., "Reduced foreign body response at nitric oxide-releasing subcutaneous implants", *Biomaterials*, 2007, 28(31): 4571-4580.

Hetrick et al., "Antibacterial nitric oxide-releasing xerogels: Cell viability and parallel plate flow cell adhesion studies", *Biomaterials*, 2007, 28(11): 1948-1956.

Hogg, Neil, "Biological Chemistry and Clinical Potential of S-Nitrosothiols", *Free Radical Biology & Medicine*, 2000, 28(10): 1478-1486.

Huang et al., "Synthesis of uniform, spherical sub-100 nm silica particles using a conceptual modification of the classic LaMer model", *Colloids and Surfaces A: Physicochemical and Engineering Aspects*, 2010, 360: 175-183.

International Preliminary Report on Patentability corresponding to International Application No. PCT/US2012/026960; mailed Mar. 13, 2014; 6 pages.

International Preliminary Report on Patentability corresponding to International Application No. PCT/US2012/026972; mailed Mar. 13, 2014; 6 pages.

Johnston et al., "Porous functionalised silica particles: a potential platform for biomolecular screening", *Chemical Communications*, 2005, p. 848-850.

Johnston et al., "A Mechanism for Forming Large Fluorescent Organo-Silica Particles: Potential Supports for Combinatorial Synthesis", *Chemistry of Materials*, 2006, 18: 6163-6169.

Katayama et al., "Design and Evaluation of S-Nitrosylated Human Serum Albumin as a Novel Anticancer Drug", *The Journal of Pharmacology and Experimental Therapeutics*, 2008, 325(1): 69-76.

Katsumi et al., "Physicochemical, Tissue Distribution, and Vasodilation Characteristics of Nitrosated Serum Albumin: Delivery of Nitric Oxide In Vivo", *Journal of Pharmaceutical Sciences*, 2004, 93(9): 2343-2352.

Katsumi et al., "Development of Polyethylene Glycol-Conjugated Poly-S-Nitrosated Serum Albumin, a Novel S-Nitrosothiol for Prolonged Delivery of Nitric Oxide in the Blood Circulation in Vivo", *The Journal of Pharmacology and Experimental Therapeutics*, 2005, 314(3): 1117-1124.

Kim et al., "Effect of electrolyte additives on sol-precipitated nano silica particles", *Ceramics International*, 2004, 30: 171-175.

Kim et al., "Size Control of Silica Nanoparticles and Their Surface Treatment for Fabrication of Dental Nanocomposites", *Biomacromolecules*, 2007, 8: 215-222.

Langford et al., "Inhibition of platelet activity by S-nitrosoglutathione during coronary angioplasty", *The Lancet*, 1994, 344: 1458-1460.

Laszlo et al., "Attenuation by nitrosothiol NO donors of acute intestinal microvascular dysfunction in the rat", *British Journal of Pharmacology*, 1995, 115: 498-502.

Lee et al., "Preparation of Highly Monodispersed Hybrid Silica Spheres Using a One-Step Sol-Gel Reaction in Aqueous Solution", *Langmuir*, 2007, 23(22): 10875-10878.

Lin et al., "Structural and Morphological Control of Cationic Surfactant-Templated Mesoporous Silica", *Accounts of Chemical Research*, 2002, 35: 927-935.

Lin et al., "Preparation of functionalized tertiary thiols and nitrosothiols", *Tetrahedron*, 2006, 62(35): 8410-8418.

Marxer et al., "Preparation of Nitric Oxide (NO)-Releasing Sol-Gels for Biomaterial Application", *Chemistry of Materials*, 2003, 15: 4193-4199.

Marxer et al., "Sol-gel derived nitric oxide-releasing oxygen sensors", *Analyst*, 2005, 130: 206-212.

(56) References Cited

OTHER PUBLICATIONS

Meng et al., "Preparation of Highly Monodisperse Hybrid Silica Nanospheres Using a One-Step Emulsion Reaction in Aqueous Solution", *Langmuir*, 2009, 25(14): 7879-7883.
Miller et al., "Functionalized Organosilica Microspheres via a Novel Emulsion-Based Route", *Langmuir*, 2005, 21: 9733-9740.
Mocellin et al., "Nitric Oxide, a Double Edged Sword in Cancer Biology: Searching for Therapeutic Opportunities", *Medicinal Research Reviews*, 2007, 27: 317-352.
Mosquera et al., "New route for producing crack-free xerogels: Obtaining uniform pore size", *Journal of Non-Crystalline Solids*, 2008, 354: 645-650.
Mowery et al., "Preparation and characterization of hydrophobic polymeric films that are thromboresistant via nitric oxide release", *Biomaterials*, 2000, 21(1): 9-21.
Nablo et al., "Sol-Gel Derived Nitric-Oxide Releasing Materials that Reduce Bacterial Adhesion", *Journal of the American Chemical Society*, 2001, 123: 9712-9713.
Nablo et al., "Antibacterial properties of nitric oxide-releasing sol-gels", *Journal of Biomedical Materials Research Part A*, 2003, 67A: 1276-1283.
Nablo et al., "Poly(vinyl chloride)-Coated Sol-Gels for Studying the Effects of Nitric Oxide Release on Bacterial Adhesion", *Biomacromolecules*, 2004, 5: 2034-2041.
Nablo et al., "Inhibition of implant-associated infections via nitric oxide release", *Biomaterials*, 2005, 26(34): 6984-6990.
Nablo et al., "Nitric oxide-releasing sol-gels as antibacterial coatings for orthopedic implants", *Biomaterials*, 2005, 26: 917-924.
Nakamura et al., "Synthesis and Characterization of Organosilica Nanoparticles Prepared from 3-Mercaptopropyltrimethoxysilane as the Single Silica Source", *The Journal of Physical Chemistry C*, 2007, 111: 18892-18898.
Nakamura et al., "One-Pot Synthesis and Characterization of Three Kinds of Thiol-Organosilica Nanoparticles", *Langmuir*, 2008, 24: 5099-5108.
Noimark et al., "The role of surfaces in catheter-associated infections", *Chemical Society Reviews*, 2009, 38: 3435-3448.
O'Halloran et al., "Metallochaperones, an Intracellular Shuttle Service for Metal Ions", *The Journal of Biological Chemistry*, 2000, 275(33): 25057-25060.
Osterholtz et al., "Kinetics of the hydrolysis and condensation of organofunctional alkoxysilanes: a review", *Journal of Adhesion Science and Technology*, 1992, 6: 127-149.
Page et al., "Antimicrobial surfaces and their potential in reducing the role of the inanimate environment in the incidence of hospital-acquired infections", *Journal Materials Chemistry—The Royal Society of Chemistry*, 2009, 19: 3819-3831.
Park et al., "Preparation of silica nanoparticles: determination of the optimal synthesis conditions for small and uniform particles", *Colloids and Surfaces A: Physicochemical and Engineering Aspects*, 2002, 197: 7-17.
Pavlos et al., "Photosensitive precursors to nitric oxide", *Current Topics in Medicinal Chemistry*, 2005, 5: 635-645.
Polizzi et al., "Water-Soluble Nitric Oxide-Releasing Gold Nanoparticles",*Langmuir*, 2007, 23: 4938-4943.
Privett et al., "Efficacy of surface-generated nitric oxide against Candida albicans adhesion and biofilm formation", *Biofouling*, 2010, 26(8): 973-983.
Radomski et al., "S-nitroso-glutathione inhibits platelet activation in vitro and in vivo", *British Journal of Pharmacology*, 1992, 107: 745-749.
Rahman et al., "An optimized sol-gel synthesis of stable primary equivalent silica particles", *Colloids and Surfaces A: Physicochemical and Engineering Aspects*, 2007, 294: 102-110.
Ramsay et al., "Systemic effects of S-nitroso-glutathione in the human following intravenous infusion", *British Journal of Clinical Pharmacology*, 1995, 40: 101-102.
Rao et al., "Synthesis of flexible silica aerogels using methyltrimethoxysilane (MTMS) precursor", *Journal Colloid Interface Science*, 2006, 300: 279-285.

Reynolds et al., "Nitric Oxide-Releasing Hydrophobic Polymers: Preparation, Characterization, and Potential Biomedical Applications", *Free Radical Biology & Medicine*, 2004, 37(7): 926-936.
Riccio et al., "Stöber Synthesis of Nitric Oxide-Releasing S-Nitrosothiol-Modified Silica Particles", *Chemistry of Materials*, 2011, 23: 1727-1735.
Richardson et al., "Potential therapeutic uses for S-nitrosothiols", *Clinical Science*, 2002, 102: 99-105.
Rojas et al., "Polyurethane coating release bioactive antibodies to reduce bacterial adhesion", *Journal of Controlled Release*, 2000, 63: 175-189.
Sakka et al., "Formation of sheets and coating films from alkoxide solutions", *Journal Non-Crystalline Solids*, 1984, 63(1-2): 223-235.
Scherer, George, "Effect of Shrinkage on the Modulus of Silica Gel", *Journal of Non-Crystalline Solids*, 1989, 109: 183-190.
Schmidt, H., "Organically Modified Silicates by the Sol-Gel Process", *Materials Research Society Symposia Proceedings*, 1984, 32: 327-335.
Schmidt et al., "Principles of hydrolysis and condensation of alkoxysilanes", *Journal Non-Crystalline Solids*, 1984, 63(1-2): 1-11.
Seabra et al., "Polynitrosated Polyesters: Preparation, Characterization, and Potential Use for Topical Nitric Oxide Release", *Biomacromolecules*, 2005, 6: 2512-2520.
Seabra et al., "Nitric oxide-releasing vehicles for biomedical applications", *Journal of Materials Chemistry*, 2009, 20: 1624-1637.
Seabra et al., "Antibacterial Nitric Oxide-Releasing Polyester for the Coating of Blood-Contacting Artificial Materials", *Artificial Organs*, 2010, 34(7): E204-E214.
Shin et al., "Inorganic/Organic Hybrid Silica Nanoparticles as a Nitric Oxide Delivery Scaffold", *Chemistry of Materials*, 2008, 20: 239-249.
Sinha et al., "UV-induced DNA damage and repair: a review", *Photochemical & Photobiological Sciences*, 2002, 1: 225-236.
Sortino et al., "Light-controlled nitric oxide delivering molecular assemblies", *Chemical Society Reviews*, 2010, 39: 2903-2913.
Stasko et al., "S-Nitrosothiol-Modified Dendrimers as Nitric Oxide Delivery Vehicles", *Biomacromolecules*, 2008, 9(3): 834-841.
Stein et al., "Hybrid Inorganic-Organic Mesoporous Silicates—Nanoscopic Reactors Coming of Age", *Advanced Materials*, 2000, 12(19): 1403-1419.
Stober et al., "Controlled Growth of Monodisperse Silica Spheres in the Micron Size Range", *Journal of Colloid and Interface Science*, 1968, 26: 62-69.
Tan et al., "Study of the Effects of Progressive Changes in Alkoxysilane Structure on Sol-Gel Reactivity", *The Journal of Physical Chemistry B*, 2006, 110: 22353-22364.
Valko et al., "Metals, Toxicity and Oxidative Stress", *Current Medicinal Chemistry*, 2005, 12: 1161-1208.
Van Helden et al., "Preparation and Characterization of Spherical Monodisperse Silica Dispersions in Nonaqueous Solvents", *Journal of Colloid and Interface Science*, 1981, 81(2): 354-368.
Varu et al., "Basic Science Review: Nitric Oxide—Releasing Prosthetic Materials", *Vascular & Endovasc Surgery*, 2009, 43:121-131.
Vogel et al., "Fluorescent organosilica micro- and nanoparticles with controllable size", *Journal of Colloid and Interface Science*, 2007, 310: 144-150.
Walcarius et al., "Rate of Access to the Binding Sites in Organically Modified Silicates. 3. Effect of Structure and Density of Functional Groups in Mesoporous Solids Obtained by the Co-Condensation Route", *Chemistry of Materials*, 2003, 15: 4181-4192.
Walshe et al., "Wilson's disease: the importance of measuring serum caeruloplasmin non-immunologically", *Annals of Clinical Biochemistry*, 2003, 40: 115-121.
Wang et al., "Nitric Oxide Donors: Chemical Activites and Biological Applications", *Chemical Reviews*, 2002, 102: 1091-1134.
Williams et al., "The Chemistry of S-Nitrosothials", *Accounts of Chemical Research*, 1999, 32: 869-876.
Williams et al., "A chemist's view of the nitric oxide story", *Organic & Biomolecular Chemistry*, 2003, 1: 441-449.
Yoo et al., "Influence of Reaction Parameters on Size and Shape of Silica Nanoparticles", *Journal of Nanoscience and Nanotechnology*, 2006, 6: 3343-3346.

(56) References Cited

OTHER PUBLICATIONS

Barbe et al., "Silica Particles: A Novel Drug-Delivery System", *Advanced Materials*, 2004, 16(21): 1959-1965.

Dobmeier et al., "Antibacterial Properties of Nitric Oxide-Releasing Sol-Gel Microarrays", *Biomacromolecules*, 2004, 5: 2493-2495.

Farias-Eisner et al., "The Chemistry and Tumoricidal Activity of Nitric Oxide/Hydrogen Peroxide and the Implications to Cell Resistance/Susceptibility", *The Journal of Biological Chemistry*, 1996, 271(11): 6144-6151.

Pulfer et al., "Incorporation of nitric oxide-releasing crosslinked polyethyleneimine microspheres into vascular grafts", *Journal of Biomedical Materials Research*, 1997, 37(2): 182-189.

Shin et al., "Nitric Oxide-Releasing Sol-Gel Particle/Polyurethane Glucose Biosensors", *Analytical Chemistry*, 2004, 76: 4543-4549.

TERTIARY S-NITROSOTHIOL-MODIFIED NITRIC_OXIDE-RELEASING XEROGELS AND METHODS OF USING THE SAME

CROSS-REFERENCE TO RELATED APPLICATIONS

This application is a continuation under 35 U.S.C. §111(a) of PCT Application No. PCT/US2012/026972, filed on Feb. 28, 2012, which claims the benefit, under 35 U.S.C. §119, of U.S. Provisional Application Serial No. 61/447,368, filed Feb. 28, 2011, and U.S. Provisional Application No. 61/565,694, filed Dec. 1, 2011, the disclosure of each of which is hereby incorporated by reference herein in its entirety.

STATEMENT OF GOVERNMENT FUNDING

The present invention was funded in part by government support under grant number 5-R01-EB000708 from the National Institutes of Health. The United States Government has certain rights in this invention.

FIELD OF THE INVENTION

The present invention is directed to nitric oxide (NO)-releasing compounds. In particular, the present invention is related to compounds that may release NO upon exposure to light.

BACKGROUND OF THE INVENTION

Reactive radical species (e.g., hydroxyl radical and superoxide) are well-suited as antimicrobial agents as their biocidal activity is broad-spectrum, lessening the likelihood of bacterial resistance and improving efficacy against multiple microbial species and strains. Light-activated antimicrobial surfaces, including titanium dioxide films and photosensitizer-modified polymers, represent new strategies for eliciting antibacterial activity by light-induced generation of reactive radicals and singlet oxygen. Medical implants, catheters, and hospital-associated surfaces that are plagued by bacterial contamination may greatly benefit from the associated disinfection/sanitization capabilities of such surfaces.

Nitric oxide (NO) is another radical species with potent broad-spectrum antimicrobial activity as evidenced by its role in the innate immune response to pathogens. The antimicrobial therapeutic utility of exogenous NO delivery via NO donors (i.e., compounds that store and release NO) has been an active area of research. However, the clinical success of NO-based antimicrobial therapies has been hindered due to the limited known methods of storing and controllably releasing enhanced payloads of NO. Macromolecular vehicles (e.g., silica nanoparticles, metallic clusters, and dendrimers) and polymers have been functionalized with multiple NO donor moieties to enable larger reservoirs of deliverable NO. The application of these materials as coatings provides localized NO release at a desired interface (e.g., an indwelling medical device) with effective mitigation of bacterial adhesion. Nevertheless, most of these formulations spontaneously liberate NO upon immersion in physiological solution.

SUMMARY OF THE INVENTION

A first aspect of the present invention comprises a co-condensed silica sol-gel coating formed from the reaction of the compound of Formula I and at least one backbone alkoxysilane:

Formula I wherein R, R' and R" are each independently alkyl and n is in a range of 0 to 10.

A second aspect of the present invention comprises a sol-gel coating comprising a tertiary S-nitrosothiol.

A further aspect of the present invention comprises a method of forming a nitric oxide (NO)-releasing sol-gel coating comprising:
(a) co-condensing a sol precursor solution comprising at least one backbone alkoxysilane and at least one tertiary thiol alkoxysilane in a solvent to form a sol;
(b) coating a substrate with the sol;
(c) optionally, drying the sol to form the sol-gel coating; and
(d) contacting the sol-gel coating with a nitrosating agent.

Another aspect of the present invention comprises a method of reducing or eliminating bacterial adhesion to a substrate comprising
(a) coating the substrate with a sol-gel coating that comprises a tertiary nitrosothiol functional group;
(b) exposing the substrate to bacteria; and
(c) irradiating the substrate to release nitric oxide, which reduces or eliminates bacterial adhesion to the substrate.

BRIEF DESCRIPTION OF THE FIGURES

The foregoing and other objects, features and advantages of the invention will become more apparent from the following more particular description of exemplary embodiments of the invention and the accompanying drawings. The drawings are not necessarily to scale, emphasis instead being placed upon illustrating the principles of the invention.

DETAILED DESCRIPTION OF EMBODIMENTS OF THE INVENTION

Figure 1:
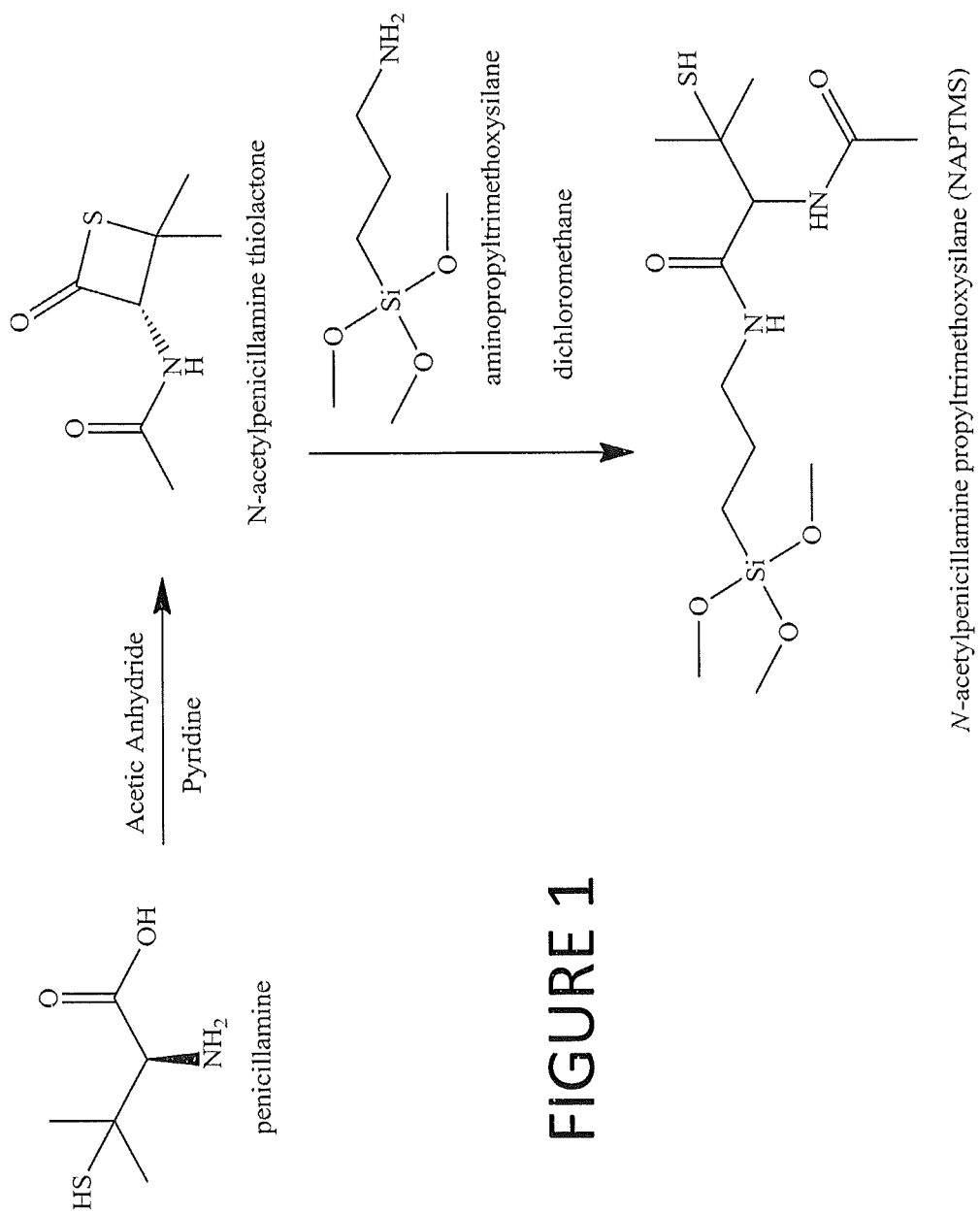
FIG. 1 provides a scheme for the synthesis of N-acetyl-penicillamine propyltrimethoxysilane (NAPTMS).

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about, " as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In the event of conflicting terminology, the present specification is controlling.

The embodiments described in one aspect of the present invention are not limited to the aspect described. The embodiments may also be applied to a different aspect of the invention as long as the embodiments do not prevent these aspects of the invention from operating for its intended purpose.

Chemical Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tent-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR$^1$R", wherein R$^1$ and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, f-butoxyl, and pentoxyl. The term "oxyalkyl" can be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents. " There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e., respectively. The arylene group can also be napthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as NR$_3$, NH$_3$, NHR$_2$, and NH$_2$R, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a cation stabilized diazeniumdiolate (i.e., NONO$^-$X$^+$). The terms "cationic amine" and "quaternary amine" refer to an amino group having an additional (i.e., a fourth) R group, for example a hydrogen or an alkyl group bonded to the nitrogen. Thus, cationic and quaternary amines carry a positive charge.

The term "alkylamine" refers to the -alkyl-NH$_2$ group.

The term "carbonyl" refers to the —(C=O)— group.

The term "carboxyl" refers to the —COOH group and the term "carboxylate" refers to an anion formed from a carboxyl group, i.e., —COO$^-$.

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group. The term "silyl" refers to groups comprising silicon atoms (Si).

The term "silane" refers to any compound that includes four organic groups, such as including any of the organic groups described herein (e.g., alkyl, aryl and alkoxy), bonded to a silicon atom.

As used herein the term "alkoxysilane" refers to a silane that includes one, two, three, or four alkoxy groups bonded to a silicon atom. For example, tetraalkoxysilane refers to Si(OR)$_4$, wherein R is alkyl. Each alkyl group can be the same or different. An "alkylalkoxylsilane" refers to an alkoxysilane wherein one or more of the alkoxy groups has been replaced with an alkyl group. Thus, an alkylalkoxysilane comprises at least one alkyl-Si bond.

The term "fluorinated silane" refers to an alkylsilane wherein one of the alkyl groups is substituted with one or more fluorine atoms.

The term "cationic or anionic silane" refers to an alkylsilane wherein one of the alkyl groups is further substituted with an alkyl substituent that has a positive (i.e., cationic) or a negative (i.e. anionic) charge, or can become charged (i.e., is ionizable) in a particular environment (i.e., in vivo).

The term "silanol" refers to a Si—OH group.

NO-Releasing Sol-Gel Coatings

Provided according to some embodiments of the invention are NO-releasing sol-gel coatings that include a tertiary nitrosothiol functional group. Such sol gel coatings are formed from a tertiary thiol and at least one backbone alkoxysilane. As used herein, the term "backbone alkoxysilane" refers to an alkoxysilane that is not modified with a nitrosothiol functional group. In some embodiments of the invention, the sol-gel coatings are xerogel coatings. The coatings will generally be referred to herein as xerogel coatings, but one of skill in the art will appreciate that the compositions and methods described herein may also be with used to form other types of sol-gel coatings. Therefore, the term "xerogel" may be substituted with the term "sol-gel" in embodiments described herein.

Also provided according to some embodiments of the invention are methods of producing NO-releasing xerogel coatings that include (a) co-condensing a sol precursor solution comprising at least one backbone alkoxysilane and at least one tertiary thiol alkoxysilane in a solvent to form a sol; (b) coating a substrate with the sol; (c) optionally, drying the sol to form the xerogel coating; and (d) contacting the xerogel with a nitrosating agent. The sol precursor solution may further include any additional components, including those described above, and/or any other additives known in the art of forming sol-gel coatings. Additionally, such methods may be performed by any method known to those of skill in the art.

Any suitable backbone alkoxysilane, or mixtures thereof, may be included in the sol precursor solution. However, in some embodiments, the backbone alkoxysilane may include a tetraalkoxysilane having the formula $Si(OR)_4$, wherein each R is independently an H, alkyl or substituted alkyl. As such, the R groups in the backbone alkoxysilane may be the same or may be different. In particular embodiments, the tetraalkoxysilane may include tetramethoxysilane (TMOS), tetraethoxysilane (TEOS), tetra-n-propoxysilane (TPOS) and/or tetra-n-butoxysilane (TBOS). In some embodiments of the invention, the backbone alkoxysilane may include an alkylalkoxysilane having the formula of $R'$—$Si(OR)_3$, wherein R' is an organic functional group (e.g., alkyl, aryl or alkylaryl) and each R is independently H, alkyl or substituted alkyl. As such, each R may be the same or may be different and each R group may be the same or different as R'. In particular embodiments, the backbone alkoxysilane may include methyltrimethoxysilane (MTMOS), ethyltrimethoxysilane (ETMOS), propyltrimethoxysilane (PTMOS), butyltrimethoxysilane (BTMOS), butyltriethoxysilane (BTEOS), and/or octadecyltrimethoxysilane (ODTMOS). In some embodiments of the invention, the backbone alkoxysilane may include an alkoxysilane having the formula $R'R''$—$Si(OR)_2$, wherein R' and R'' are each independently an organic functional group (e.g., alkyl, aryl or alkylaryl) and each R is independently H, alkyl or substituted alkyl. In some embodiments of the invention, the backbone alkoxysilane may include an alkoxysilane having the formula of $R'R''R'''$—$SiOR$, wherein R', R'' and R''' are each independently an organic functional group (e.g., alkyl, aryl or alkylaryl) and R is H, alkyl or substituted alkyl.

Examples of backbone alkoxysilanes that may be used in some embodiments of the invention include acryloxypropylmethyldimethoxysilane, 3-acryloxypropyltrimethoxysilane, allyltriethoxysilane, allytrimethoxysilane, amyltriethoxysilane, amyltrimethoxysilane, 5-(bicycloheptenyl)methyltriethoxysilane, 5-(bicycloheptenyl)methyltrimethoxysilane, 5-(bicycloheptenyl)dimethylmethoxysilane, 5-(bicycloheptenyl)methyldiethoxysilane, bis(3-cyanopropyl)diethoxysilane, bis(3-cyanopropyl)dimethoxysilane, 1,6-bis(trimethoxysilyl)hexane, bis(trimethylsiloxy)methylsilane, bromomethyldimethylmethoxysilane, 3-bromopropyltriethoxysilane, n-butyldimethylmethoxysilane, tert-diphenylmethoxysilane, n-butyldimethoxysilane, n-butyldiethoxysilane, n-butyltrimethoxysilane, 2-(carbomethoxy)ethyltrimethoxysilane, 4-chlorobutyldimethylmethoxysilane, 4-chlorobutyldimethylethoxysilane, 2-chloroethyltriethoxysilane, chloromethyldimethylethoxysilane, p-(chloromethyl)phenyltriethoxysilane, p-(chloromethyl)phenylethoxysilane, chloromethyltriethoxysilane, chlorophenyltrimethoxysilane, 3-chloropropylmethyldimethoxysilane, 3-chloropropyltriethoxysilane, 2-cyanoethylmethyltrimethoxysilane, (cyanomethylphenethyl)triethoxysilane, 2-(3-cyclohexenyl)ethyl]trimethoxysilane, cyclohexydiethoxymethylsilane, cyclopentyltrimethoxysilane, di-n-butyldimethoxysilane, dicyclopentyldimethoxysilane, diethyldiethoxysilane, diethyldimethoxysilane, diethyldibutoxysilane, diethylphosphatoethyltriethoxysilane, diethyl(triethoxysilylpropyl)malonate, di-n-hexyldimethoxysilane, diisopropyldimethoxysilane, dimethyldimethoxysilane, 2,3-dimethylpropyldimethylethoxysilane, dimethylethoxysilane, diphenydiethoxysilane, diphenyldimethoxysilane, diphenylmethylethoxysilane, 2-(diphenylphosphino)ethyltriethoxysilane, divinylethoxysilane, n-dodecyltriethoxysilane, 2-(3,4-epoxycyclohexyl)ethyltrimethoxysilane, ethyltriethoxysilane, ethyltrimethoxysilane, 3-glycidoxypropyldimethylethoxysilane, (3-glycidoxypropyl)methyldimethoxysilane, 3-glycidoxypropyltrimethoxysilane, n-heptylmethyldimethoxysilane, n-hexadecyltriethoxysilane, 5-hexenyltrimethoxysilane, n-hexytriethoxysilane, n-hexyltnethoxysilane, 3-iodopropyltriethoxysilane, 3-iodopropyltrimethoxysilane, isobutyltrimethoxysilane, isobutyltriethoxysilane, isocyanatopropyldimethylmethoxysilane, 3-isocyanatopropyltriethoxysilane, isooctyltriethoxysilane, 3-mercaptopropyl-methyldimethoxysilane, 3-mercaptopropyltrimethoxysilane, 3-mercaptopropyltriethoxysilane, 3-methacryloxypropylmethyldiethoxysilane, 3-methacryloxypropyl-methyldiethoxysilane, 3-methacryloxypropyltrimethoxysilane, 3-(4-methoxyphenyl)propyltrimethoxysilane, methylcyclohexyldiethoxysilane, methyldiethoxysilane, methyldimethoxysilane, methyldodecyldiethoxysilane, methyl-n-octadecyldimethoxysilane, methyl(2-phenethyl)dimethoxysilane, methylphenyldiethoxysilane, methylphenyldimethoxysilane, methyl-n-propyldimethoxysilane, methyltriethoxysilane, neophylmethyldiethoxysilane, n-octadecyldimethylmethoxysilane, n-octadecyltriethoxysilane, n-octadecyltrimethoxysilane, 7-octenyltrimethoxysilane, n-octylmethyldimethoxysilane, n-octyltriethoxysilane, phenethyldimethylmethoxysilane, phenethyltriethoxysilane, phenyldimethylethoxysilane, phenyltriethoxysilane, phenyltriethoxysilane, phthalocyanatodimethoxysilane, n-propyltrimethoxysilane, styrylethyltrimethoxysilane, tetra-n-butoxysilane, tetraethoxysilane, tetrapropoxysilane, (tridecafluoro-1,1,2,2,-tetrahydrooctyl)-1-trimethoxysilane, triethoxysilane, triethoxysilylpropylethyl carbamate, triethylethoxysilane, (3,3,3-trifluoropropyl)methyldimethoxysilane, (3,3,3-trifluoropropyl)triethoxysilane, trimethoxysilane, 1-trimethoxysilyl-2-(p,m-chloromethyl)phenylethane, trimethylethoxysilane, 2-(trimethylsiloxy)ethyl methacrylate, p-trimethylsiloxynitrobenzene, triphenylethoxysilane, n-undeceyltriethoxysilane, vinyldimethylethoxysilane and vinyltrimethoxysilane.

The particular backbone alkoxysilanes used and ratio of each in a sol precursor solution may be varied depending on the particular tertiary thiol alkoxysilanes present in the sol, the particular substrate coated, the porosity of the coating desired, the hydrophobicity of the coating desired, and the NO-release kinetics desired.

Any suitable tertiary thiol alkoxysilane, or mixtures thereof, may be included in the sol precursor solution. In some embodiments, the tertiary thiol alkoxysilane has the following structure: $(OR)(OR')(OR'')Si(R^x)$, wherein R, R' and R'' are each independently H, alkyl or substituted alkyl and $R^x$ is functional group that comprises a tertiary thiol group. In particular embodiments, the tertiary thiol alkoxysilane has the structure:

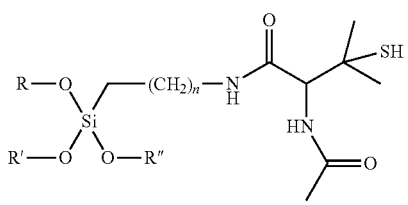

wherein R, R' and R" are each independently H, alkyl or substituted alkyl and n is in a range of 0 to 10. In some embodiments, R, R' and R" are each independently alkyl and n is 0-5. Furthermore, in particular embodiments of the invention, the tertiary thiol is a compound having the structure:

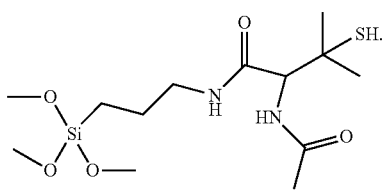

According to some embodiments of the invention, also provided are the nitrosothiol analogs of such compounds.

Once a xerogel coating has been formed, the tertiary thiol may be nitrosated to transform the tertiary thiol groups to tertiary nitrosothiol functional groups. Methods of nitrosating thiol functional groups are known in art and some methods are described in the examples below. Any suitable method of nitrosating the tertiary thiol groups may be used. An example of a nitrosating agent that may be used according to embodiments of the invention is acidified nitrite.

In some embodiments, other NO-releasing functional groups may also be present in the xerogel, including but not limited to, primary or secondary nitrosothiols, diazeniumdiolate, nitrosamine, hydroxyl nitrosamine, hydroxyl amine, hydroxyurea and metal nitrosyl complexes.

In some embodiments of the invention, the sol precursor solution may also include at least one multifunctional alkoxysilane. The term "multifunctional alkoxysilane" refers to an alkoxysilane that includes at least one functionality that provides at least one additional property to the xerogel coating. The multifunctional alkoxysilane may be a backbone alkoxysilane, a nitrosothiol alkoxysilane or may be a different alkoxysilane. In some embodiments, the multifunctional alkoxysilane has the formula R'R"R'"SiOR, wherein R is H, alkyl or substituted alkyl, R', R" and R'" are each independently a substituted or unsubstituted alkyl, a substituted or unsubstituted aryl, a substituted or unsubstituted alkylaryl, a substituted or unsubstituted arylalkyl or an organic moiety that provides at least one additional property to the xero-gel coating. At least one of R', R" and R'" is an organic moiety necessary that provides the at least one additional property to the xerogel coating. This organic moiety may be chosen based on the property desired and the stability of a particular functionality under xerogel processing conditions. The multifunctional alkoxysilane may be introduced into the sol precursor solution with the backbone alkoxysilane and tertiary thiol alkoxysilane to form a sol which may then form a multifunctional co-condensed siloxane coating. Examples of additional properties that may be imparted to a substrate via the multifunctional alkoxysilane include:

Anti-corrosive—Any suitable alkoxysilane that may impart anti-corrosive properties to the xerogel coating may be used. Common inhibitors known to one skilled in the art to prevent corrosion of metallic surfaces include imines formed from the condensation products of aldehydes and amines, cinnamaldehyde and ascorbic acid. As such, in some embodiments, the multifunctional alkoxysilane may include a dipodal alkoxysilane formed from the condensation of glutaraldehyde and two 3-aminopropyltrimethoxysilanes and/or a cinnamamide silane derivative.

Anti-inflammatory—Any suitable alkoxysilane that may impart anti-inflammatory properties to the xerogel coating may be used. Widely accepted anti-inflammatory agents includingibuprofen, diclofenac, and naproxen may be covalently attached to a medical device surface to minimize inflammation and pain caused by device implantation. As such, in some embodiments, the multifunctional alkoxysilane may include an ibuprofen alkoxysilane derivative, a diclofenac alkoxysilane derivative or a naproxen alkoxysilane derivative. Ester linkages sensitive to enzymatic or hydrolytic cleavage may also be employed to provide controlled release of the anti-inflammatory agent into the surrounding tissue.

Anti-microbial—Any suitable alkoxysilane that may impart antimicrobial properties to the xerogel coating may be used. Broad spectrum antimicrobial agents including quaternary ammonium compounds, chlorhexidine, polyhexamethylene biguanide, triclosan, ionic silver complexes, iodine, and hypochlorite may be derivatized with an alkoxysilane to provide microbicidal activity to the device surface or the surrounding tissue. In some embodiments, the multifunctional alkoxysilane may include a quaternary ammonium alkoxysilane derivative, a chlorhexidene alkoxysilane derivative, a polyhexamethylene biguanide alkoxysilane derivative, a triclosan alkoxysilane derivative, an ionic silver alkoxysilane derivative, a iodine-releasing alkoxysilane derivative and a hypochlorite alkoxysilane derivative.

Anti-oxidative—Any suitable alkoxysilane that may impart anti-oxidative properties to the xerogel coating may be used. In some embodiments, the multifunctional alkoxysilane may include a vitamin E alkoxysilane derivative, an ascorbic acid alkoxysilane derivative, a glutathione alkoxysilane derivative, a N-acetylcysteine alkoxysilane derivative and other thiol alkoxysilane derivatives. Such alkoxysilanes may be incorporated into medical device coatings to mediate oxidative stress at the implant surface or in the surrounding tissue.

Crosslinking—Any suitable alkoxysilane that may impart additional crosslinking to the xerogel coating may be used. Functional alkoxysilanes are routinely used by those skilled in the art of xerogel chemistry to enable methods of curing and forming a stable siloxane network via covalent bonding other than siloxane bonds. In the present invention this affords a method for forming stable tertiary thiol coatings that do not involve sintering at high temperatures. In some embodiments, the multifunctional alkoxysilane may include an epoxy group including (3-glycidoxypropyl)trimethoxysilane, (3-glycidoxypropyltriethoxysilane), (3-glycidoxypropyl)methyldiethoxysilane), 1,3-bis(glycidoxypropyl)tetramethyl-disiloxane, 2-(3,4-epoxycyclohexyl) ethyltrimethoxysilane; acrylo including (3acryloxypropyl) trimethoxysilane, acryloxymethyltrimethoxysilane, methacryloxypropyltriethoxysilane, methacryloxypropyltrimethoxysilane); isocyano including 3-isocyanatopropyltriethoxysilane, isocyanatopropyltrimethoxysilane; vinyl including vinylmethyldiethoxysilane, vinylmethyldimethoxysilane amino, vinyltriethoxysilane, vinyltrimethoxysilane, vinyltriisopropxysilane; and amino including 3-aminopropyltrimethoxysilane, 3-aminopropyltriethoxysilane, 4-aminobutyltriethoxysilane.

In addition to intra-silane bonding, the functionalities may be used to facilitate crosslinking of the xerogel coating with a top coated polymer layer. The top-coated polymer layer may be polymerized at the surface and react with the $R_3$ functionality from the multifunctional alkoxysilane in the xerogel coating in order to facilitate bonding between the two surface layers and prevent delamination of the polymer top-coat. The top-coat may be applied during device fabrication or applied on a macroscopic scale upon device implantation as is the case with methacrylate-based bone cement used to anchor artificial joints. Acrylate or methacrylate derivatized alkoxysilane residues can participate in the free-radical initiated polymerization of the two bone cement monomers.

Surface charge—Any suitable alkoxysilane that may impart surface charge to the xerogel coating may be used. One of the most widely known strategies to alter protein adsorption, bacterial adhesion, and concomitant biofouling of implantable devices is to alter the charge of the implant surface. However, these passive surface functionalites alone have been unable to dramatically improve foreign body response. In the present invention, the combination of nitric oxide and surface charge may provide medical devices with improved biocompatibility. Thus, in some embodiments, the multifunctional alkoxysilane may include a cationic alkoxysilane such as (2-N-benyzlaminoethyl)-3-aminopropyl-trimethoxysilane, hydrocholoride; bis(methoxyethyl)-3-trimethoxysilylpropyl-ammonium chloride; N—N-didecyl-N-methyl-N-(3-trimethoxysilyl)ammonium chloride; N-trimethyoxysilylpropyl-N,N,N-trimethyl ammonium chloride; octadecylbis(triethoxysilylpropyl)-ammonium chloride; and octadecyldimethyl(3-trimethoxysilylpropyl) ammonium chloride. In some embodiments, the multifunctional alkoxysilane may include an anionic alkoxysilanes such as 3-trihydroxysilylpropylmethyl phosphonate, sodium salt and carboxyethylsilanetriol, sodium salt.

Surface hydrophilicity—Any suitable alkoxysilane that may impart hydrophilic properties to the xerogel coating may be used. Alkoxysilanes containing repeat poly(ethylene)oxy groups may be used to increase the wetability of the NO-releasing coating thereby helping to improve biocompatibility upon implantation and also enhance the rate of water uptake in the co-condensed siloxane coating. Therefore, in some embodiments, the multifunctional alkoxysilane may include a hydrophilic silane such as N-triethoxysilylpropyl)-O-polyethyleneoxide urethane; N-3-[amino(polypropylenoxy)]aminopropyltrimethoxysilane; bis-[3-(triethoxysilyl-propoxy)-2-hydroxypropoxy]polyethylene oxide; bis(3-triethoxysilylpropyl)polyethylene oxide (25-30); [hydroxy (polyethyleneoxy)propyl]-triethoxysilane; and 2-[methoxy (polyethyleneoxy)propyl]-trimethoxysilane.

Surface hydrophobicity—Any suitable alkoxysilane that may impart hydrophobic properties to the xerogel coating may be used. Hydrophobic silanes are known to those skilled in the art to increase lipophilicity of surfaces. In some embodiments, the multifunctional alkoxysilane may include linear alkyl, branched and cyclic alkylalkoxysilanes having at least three carbon atoms, substituted and unsubstituted phenyl alkoxysilanes, and fluorinated alkoxysilanes. For example, a concentration of 10-20% (v/v) fluoroalkoxysilane may be included in the sol precursor solution. Exemplary fluoroalkoxysilanes may include heptadecafluoro-1,1,2-2-tetrahydrodecyl)triethoxysilane, (3,3,3-trifluoropropyl)trimethoxysilane, (perfluoroalkyl)ethyltriethoxysilane, nonafluorohexyltrimethoxysilane, nonafluorohexyltriethoxysilane, (tridecafluoro-1,1,2,2-tetrahydrooctyl)triethoxysilane, and (tridecafluoro-1, 1, 2, 2-tetrahydrooctyl)trimethoxysilane.

The silane precursors may be combined in any suitable ratio in the sol. In particular embodiments, the concentration of the tertiary thiol alkoxysilane may be in a range of about 1 to about 40 mol percent, and in some embodiments, 10 to 30 mol %, and the concentration of the backbone alkoxysilane may be in a range of about 70 to about 90 mol %. The concentrations are based on the total silane concentration in the sol precursor solution.

The volume and type of the solvent employed in the sol precursor solution may vary. Examples of solvents include water, methanol, ethanol, propanol, butanol, 2-ethoxyethanol, formamide, dimethylformamide, dioxane, tetrahydrofuran, and mixtures thereof. In some embodiments, drying control additives may be included in the sol to facilitate the drying of the gels. Such drying control additives may allow for drying of the gel without cracking. Examples of drying control additives include formamide, dimethylformamide, diethylamine amine, acetonitrile, dioxane, glycerol, oxalic acid, surfactants and mixtures thereof.

In some embodiments of the invention, the sol precursor solution may include an acid or base catalyst. The catalyst may initiate the sol-gel formation process. Any suitable base catalyst may be used. However, examples of base catalysts include ammonia, alkali metal hydroxides, fluorides (NaF) and organic bases. An example of an acid catalyst is HCl. In some embodiments, the concentration of the acid catalyst is in a range of about 0.025M to about 0.75M. In some embodiments, the concentration of the acid catalyst is about 0.050M.

In some embodiments of the invention, a radical initiator may be added to the sol precursor solution. Any suitable radical initiator may be used, but in some embodiments, initiators may include organic peroxides and azo compounds (e.g. azobisisobutyronitrile, AIBN) that may be used to initiate polymerization of modified alkoxysilanes (e.g. 3-methacryloxypropyl trimethoxysilane) to strengthen the siloxane coating.

In some embodiments of the invention, a porogen may be included in the sol precursor solution. Control of porosity of the sol may enable increased or decreased water uptake of the coating, and thus may facilitate tissue and bone ingrowth on and into the device, and may provide a mechanism for analyte diffusion in the case of sensor-based implants. Any suitable porogen may be used. However, examples of porogens include dendrimers, water soluble polymers such as PVP, PVA, PEG, and biodegradable polymers such as PLA, PGA, PLGA, caprolactones, polyesters and polypeptides. In some embodiments, the concentration of the porogen may be in a range of from about 0.05 to about 20% (w/v) of the cast sol solution. The molecular weights and resulting macromolecular structure of the sol may govern pore size and geometry.

The substrate may be coated with the sol and/or sol precursor solution to form the coating. In some embodiments of the present invention, methods of coating the substrate include applying the coating to a device via dip-coating, spread-coating, spray coating, spin coating, brushing, imbibing, rolling and/or electrodeposition. Other methods may be used and are known to those of skill in the art. The casting volume may also affect the properties of the coating because it may affect drying time and the amount of material deposited, and hence the concentration of NO release. In some embodiments, the casting volumes may be in the range of from about 1 to about 200 µL/cm$^2$, and in particular embodiments, in a range of about 4 to about 60 µL/cm$^2$.

In some embodiments of the invention, the coating may be applied to the substrate as only one layer. In some embodiments, the substrate may be coated two or more times to a form multi-layered coating. A multi-layered coating may include multiple layers of a single xerogel containing one NO donor composition according some embodiments of the invention. The multiple layers may allow the combination of relatively thin layers, which may dry more evenly and therefore show less cracking, to form a thicker coated layer.

Alternatively, a multi-layered coating may include at least one layer formed from a different xerogel composition according to an embodiment of the invention. Such a combination of different types of NO-releasing xerogel coatings may impart additional functionality to the device surface. Furthermore, in some embodiments, a multi-layer coating may include at least one coating layer that is formed from a different xerogel composition or a different type of coating material altogether. For example, a NO-releasing xerogel coating according to an embodiment of the invention may be top coated with additional polymeric materials that may impart stability to the underlying xerogel coating and regulate diffusion of water to the coating. Such coatings may also reduce or eliminate biofouling at the surface. Any suitable top coating may be used. However, examples of top coatings include polyurethane, collagen, silicone rubber, polystyrene, polymethylmethacrylate, polyvinylchloride and combinations thereof. While a top coat may be applied, in some embodiments, a NO-releasing xerogel coating according to an embodiment of the invention is the top layer of a multiple layered coating.

In some embodiments, the surface may be coated with an additional polymer substrate designed to impart passive surface functionality in combination with the NO-released from the underlying xerogel coating. Examples may include polyurethane, collagen, silicone rubber, polystyrene, polymethylmethacrylate and polyvinylchloride.

In some embodiments, a sol and/or sol precursor solution according to an embodiment of the invention may be further treated after being applied to the substrate. For example, the coating may be dried under vacuum, photocured, or heat cured to form the xerogel coating. As additional examples, drying agents may also be applied to aid in the complete co-condensation of the components of the sol precursor solution and to prevent cracking/breaking during evaporation of the sol solvent(s). Additionally the siloxane network may be further aged (i.e., driven to complete conversion of silanols into siloxanes bridges) by exposing the coating and substrate to basic solutions up to several orders of magnitude higher in base concentration than that employed during the coating preparation.

Coatings according to embodiments of the invention may be of any suitable thickness. The thickness may depend on the number of layers contained within the coating and on the method used to apply the coating. In some embodiments, the total thickness of the coating (including all layers, both NO-releasing co-condensed siloxane coating layers and other layers) may be in a range of from about 1 to about 250 µm, in some embodiments, in a range of about 20 to about 150 µm, and in some embodiments, in a range of about 5 to about 20 µm.

The NO-releasing xerogel coatings may have desirable properties such as increased NO storage, lengthened NO-release durations, and environmentally triggered mechanisms of NO donor decomposition. Furthermore, in some embodiments of the invention, the NO-releasing xerogel coatings may have a total NO storage ranging from about 0.01 to about 10 µmol NO.cm$^{-2}$, and in particular embodiments, in a range of about 0.8 to 2 µmol NO.cm$^{-2}$. In some embodiments the NO release upon irradiation of light is in a range of about 1 to 150 µmol NO/cm$^2$s$^2$, and in some embodiments, in a range of about 10 to 120 µmol/cm$^2$s$^2$. The NO release may depend on light wattage and distance of the lamp.

The xerogel coating may then be nitrosated by any suitable method, including but not limited to contacting the xerogel with nitrosating agents such as nitrous acid/acidified nitrite. In some embodiments, the nitrosating agent may be in excess of the thiol groups, in some cases an excess in a range of 10 fold to 100 fold.

Substrates

NO-releasing xerogel coatings according to embodiments of the invention may be applied to any suitable substrate. However, in some embodiments, the NO-releasing xerogel coating may be applied to a medical device. As used herein, the term "medical device" refers to any devices or structures used in medical diagnosis, therapy or surgical procedure, including any physical object that can be implanted into the body or which comes in direct contact with the body. These devices may be useful for diagnostic or therapeutic purposes, and can be implanted for use on a permanent or temporary basis. They may be made to replace and act as a missing biological structure. They may be sensors or probes. They may be devices, such as drug delivery devices, for example, in the form of implantable pills or drug-eluting implants. Medical devices may contain electronics, such as artificial pacemakers, retinal implants, cochlear implants, and pulse-generators. Also included are components of these devices, such as electrical leads and guide wires.

Specific medical devices include but are not limited to orthopedic implants, including replacement joints, re-constructive prosthesis (e.g. maxillofacial prostheses), bone cement, bone defect fillers, spinal cages, bone anchors, bone screws, fracture-fixation plates, screws, and tacks, artificial tendons and ligaments, and dental implants; cardiovascular implants, including vascular grafts, vascular access devices and ports, stents, balloons, pacemakers, myocardial plugs, lead coatings including coatings for pacemaker leads, defibrillation leads and coils; ventricular-assist-device devices (e.g. left ventricular assist hearts and pumps, total artificial hearts, shunts, valves including heart valves and vascular valves, anastomosis clips and rings, suture anchors, tissue staples and ligating clips at surgical sites); ophthalmic implants, including corneal implants, retinal implants, and introcular lenses; drug delivery systems; cochlear implants; tissue screws and tacks; tissue adhesives and sealants; tissue staples and ligating clips at surgical sites; matrices for cell encapsulation and tissue engineering; tissue bulking devices and agents; tissue engineering scaffolds for cartilage, bone, skin and other in vivo tissue regeneration; sutures; suture anchors; surgical drapes; gauze; protective platings; breast enlargement prostheses; ostomy devices and long-term urinary devices; bracheotherapy devices; ventriculo-peritoneal shunts; pumps (including implantable infusion pumps); stents (e.g. coronary vascular stents, arterial stents, peripheral vascular stents, cerebral, urethral, ureteral, biliary, tracheal, gastrointestinal and esophageal stents); stent grafts; catheters (e.g., renal or vascular catheters such as balloon catheters, dialysis catheters, long term tunneled central venous catheters, peripheral venous catheters, short-term central venous catheters, arterial catheters, pulmonary artery Swan-Ganz catheters, urinary catheters, long term non-tunneled central venous catheters, peritoneal catheters, and ventricular catheters); guide wires; trocar needles; electrical leads, balloons; implantable stimulators; implantable pulse generators; filters (e.g., vena cava filters and mesh filters for distil protection devices); vascular grafts, abdominal aortic aneurysm devices such as stents and grafts; dialysis ports, embolization devices including cerebral aneurysm filler coils (including Guglilmi detachable coils and metal coils); embolic agents; bulking agents; septal defect closure devices; anastomosis clips and rings; cannulae; contraceptive intrauterine devices; metal wire ligatures; urethral slings; hernia "meshes;" sensors, including biosensors, and biopsy devices, as well as any other device that is implanted or inserted into the body for medical purposes.

The medical device itself may be formed from or include any suitable material. The material comprising a given medical device is chosen based in part on the particular application; for example, the mechanical properties of the device may need to conform to the natural tissue surrounding it. Thus, a different material may be used, for example, for a sensor versus a suture, and for an orthopedic implant versus a retinal implant. For a discussion of the many materials that can be used in medical devices, see Helmus et al., *Toxicologic Pathology* 36:70-80 (2008), incorporated herein by reference. Examples of materials that may form or be included in the medical device include metals (including germanium, cobalt, chromium, nickel, aluminum, zirconium, tin, hafnium, vandaium, and titanium), metal alloys (including titanium-niobium, titanium-aluminum-vanadium, titanium-aluminum-niobium, vanadium steel, cobalt chrome, the superalloy CoCrMo, and stainless steel), carbon, carbon fibers, carbon polymer, ceramics and glasses (including oxides, carbides, nitrides, or nitro-carbides of silicon, titanium, tantalum, tungsten, zirconium, niobium, chromium, or aluminum), ceramic-metal composites; synthetic and natural polymers and copolymers (including rubber, nylon, silicone, polyurethane, polyethylene, polyvinyl chloride, polystyrene, polyeretherketone, polytetrafluoroethylene tetraphthalate, polyethylene tetraphthalate, polytetrafluoroethylene, polyglycolic acid, latex, polyglycolic acid, polylactide-co-glycolide, polylactic acid polymethyl methacrylate; latex, gelatin, collagen, albumin, and globulin) and any combination thereof.

In some embodiments of the present invention, at least one material of a medical device may be pretreated prior to the coating of the device with a NO-releasing xerogel coating according to an embodiment of the invention. For example, mechanical surface modifications may include machining, grinding, polishing, or blasting metal surfaces prior to deposition of the NO-releasing coating to increase interfacial surface area and allow for increased silane bonding/functionalization. Chemical methods of surface preparation may include alkaline treatment, acidic treatment, hydrogen peroxide treatment, argon and oxygen plasma cleaning, and ozone cleaning. In some embodiments of the the present invention, the surface is pretreated with a dipodal alkoxysilane or an aminoalkoxysilane/glutaraldehyde treatment to facilitate proper adhesion of the NO-releasing siloxane coating and prevent hydrolysis at the substrate surface. In some embodiments, a metal surface may be pretreated, for example with an alkaline treatment, in order to form a metal hydroxide layer that may react with a silane such as a backbone alkoxysilane or tertiary thiol alkoxysilane. The bonding between the silanes in the sol precursor solution with the metal surface may facilitate adhesion and stability of the xerogel coating on the surface.

Also provided herein are methods of reducing or eliminating microbial adhesion to a substrate that include (a) coating the substrate with a sol-gel coating that comprises a tertiary nitrosothiol functional group; (b) exposing the substrate to microbes; and (c) irradiating the substrate to release nitric oxide, which reduces or eliminates microbe adhesion to the substrate. In some embodiments, the microbes are bacterial and such methods reduce bacterial adhesion. Any sol-gel coating described herein may be used, including xerogel coatings.

EXAMPLES

Materials

3-Aminopropyltrimethoxysilane (APTMS), tetraethoxysilane (TEOS), and isobutyltrimethoxysilane (BTMOS) were purchased from Gelest (Tullytown, Pa.). Methyltrimethoxysilane (MTMOS) and diethylenetriamine pentaacetic acid (DTPA) were purchased from Fluka (Bucks, Switzerland). Tetramethoxysilane (TMOS) and Dulbecco's Modified Eagle's Medium (DMEM) were purchased from Sigma (St. Louis, Mo.). D(−)-Penicillamine, ethanol, and tetrahydrofuran (THF) were obtained from Fisher Scientific, (Fair Lawn, N.J.). *Pseudomonas aeruginosa*(ATCC #19143) was obtained from American Type Culture Collection (Manassas, Va.). Nitric oxide calibration gas (26.8 ppm; balance $N_2$) was purchased from National Welders Supply Co. (Durham, N.C.). Type A19 60 and 100 W General Electric and type A21 200 W Sylvania incandescent light bulbs were purchased from Lowe's (Chapel Hill, N.C.). Tecoflex SG-80A polyurethane was a gift from Thermedics (Woburn, Ma.). Other solvents and chemicals were analytical-reagent grade and used as received. Distilled water was purified to 18. 2 MΩ·cm with a Millipore Milli-Q Gradient A-10 water purification system (Bedford, Mass.).

Silane and Xerogel Synthesis

Synthesis of N-Acetyl Penicillamine (NAP) Thiolactone. Acetic anhydride (96 mmol, 9.80 g) was added dropwise to a well stirred solution of D-(−) penicillamine (40 mmol, 5.97 g) in pyridine (50 mL) at 0° C. After 30 min, the flask was removed from ice and allowed to stir at room temperature for 15 h. The resultant orange solution was partitioned between chloroform and dilute HCl and washed 4× with dilute HCl. After drying over $MgSO_4$, the organic phase was evaporated to yield an orange residue. The residue was first dissolved in absolute ethanol (20 mL), and then precipitated in pentane at −78° C. The light yellow crystalline product was isolated by filtration (2.07 g, 30%). $^1$H NMR ($CDCl_3$) δ 1.65 (s, $CH_3$), 1.86 (s, $CH_3$), 2.05 (s, $NHCOCH_3$), 5.68-5.70 (d, $CH(CH_3)_2$), 6.56 ($NHCOCH_3$). $^{13}$C NMR ($CDCl_3$) δ 22.52 ($NHCOCH_3$), 26.20 ($CH(CH_3)_2$), 30.22 ($CH(CH_3)_2$), 51.23 (CH), 169.37 ($NHCOCH_3$), 192.21 (SCO).

Synthesis of N-Acetyl Penicillamine Propyltrimethoxysilane (NAPTMS). APTMS (10 mmol, 1.78 g). was added to a stirring solution of NAP thiolactone (10 mmol, 1.72 g) in methylene chloride (20 mL). The light yellow solution was stirred for 4 h at room temperature before distillation of the methylene chloride to yield NAPTMS as a viscous clear oil. $^1$H NMR ($CDCl_3$) δ 0.54 (t, $SiCH_2$), 1.24 and 1.39 (s, $CH(CH_3)_2SH$), 1.54 (m, $SiCH_2CH_2$), 1.96 (s, $NHCOCH_3$), 2.96 and 3.21 (m, $SiCH_2CH_2CH_2$), 3.44 (s, $Si(OCH_3)_3$), 4.63 (d, $CHC(CH_3)_2SH$), 6.99 (d, $CHNHCOCH_3$), 7.70 (t, $CH_2NHCOCH$). $^{13}$C NMR ($CDCl_3$) δ □6.59 ($SiCH_2$), 22.42 and 22.97 ($CH(CH_3)_2SH$), 28.64 ($NHCOCH_3$), 30.80 ($SiCH_2CH_2$), 41.93 ($CHC(CH_3)_2SH$), 46.23 ($SiCH_2CH_2CH_2$), 50.35 ($Si(OCH_3)_3$), 60.32 (CHC $(CH_3)_2SH$), 169. 64 ($CHNHCOCH_3$), 170.17 (CHCONH).

Synthesis of NAPTMS-derived Xerogels. Xerogel coatings were prepared as follows. Sols containing 10-40 mol % NAPTMS (balance MTMOS, BTMOS, TMOS, or TEOS) were prepared by shaking ethanol (1050 µL), backbone alkylalkoxy- or alkoxysilane (86-201 µL), NAPTMS (53-210 mg; total silane molar amount=1 mmol), water (46 µL) and 0.5 M HCl (136 μl) for 30 min-4 h. All substrates were sonicated in ethanol for 20 min, dried under $N_2$, and ozone (UV) cleaned for 20 min in a BioForce TipCleaner (Ames, Iowa) prior to casting. Aliquots of 30-120 μl were cast onto 9×25 mm² precleaned glass substrates. After casting of the sol, all physisorbed films were allowed to dry at room temperature overnight, and then transferred to a 45° C. oven for 2 d. S-Nitrosothiols were then formed on the room temperature-cooled films.

S-Nitrosothiol Formation. Thiols of xerogels were nitrosated by reaction with acidified nitrite. Films were protected from light and incubated for fixed intervals in solution (2 mL) containing a 100-fold molar excess of $NaNO_2$ and HCl (vs. moles thiol) and 500 μM DTPA. The xerogels were washed with 500 μM DTPA and stored in the dark at −20° C. until used, Spectral characterization of RSNO formation was performed by affixing the slides normal to the light path of a PerkinElmer Lambda 40 UV/vis spectrophotometer (Norwalk, Conn.) in cuvettes containing 2 mL phosphate buffered saline (PBS; 10 mM phosphate, pH 7.4). Absorbance at 590 nm was monitored as a function of nitrosation reaction time and concentration of excess nitrosating agent for each composition of xerogel, Characterization Nitric Oxide Release. Nitric oxide release from RSNO-modified xerogels was monitored in 1 s intervals using a Sievers model 280i chemiluminescence nitric oxide analyzer (NOA) (Boulder, Colo.), Calibration of the instrument was performed prior to each experiment using 26.8 ppm NO gas (balance $N_2$) and air passed through a Sievers NO zero filter. Individual slides were immersed in 25 mL PBS containing 500 μM DTPA and sparged with a 200 mL/min $N_2$ stream. Temperature of the sample was maintained at 37° C. during irradiation by circulating thermostatted water through a custom-made flow cell. The water was circulated between the flow-cell housing the sample flask and a thermostatted water bath shielded from the lamp. Light-initiated NO release was examined by using incandescent bulbs of various wattages placed 0.6 m above the sample flask to monitor light induced fluxes and at a distance of 0.3 m without thermostatting for assaying total NO storage. The sample flask was shielded from light with aluminum foil when light was not the intended initiator of NO release.

Xerogel Film Stability. Nitrosated xerogel films on glass slides (n=3) were immersed in 10 mL PBS and incubated at 37° C. Films were removed and transferred to fresh solutions of PBS at fixed intervals of 6, 12, 24 h and 7 d. Silicon (Si) concentrations in the PBS soak solutions were determined using a Teledyne Leeman Labs Prodigy inductively coupled plasma optical emission spectrometer (ICP-OES) (Hudson, N.H.) calibrated with 0-50 ppm Si standard solutions in PBS, Blank glass slides as well as slides cast with 30 μL of a 20 mg $mL^{-1}$ polyurethane in THF solution (to examine Si leaching of glass substrates with one side coated with a polymer) were assessed as controls.

Film Thickness. Measurements of the RSNO-modified xerogels were acquired with a KLA Tencor P15 Profilometer (Milpitas, Calif.) at a scan speed of 100 μm $s^{-1}$, 200 Hz sampling rate, and a scan length of 2000 μm. Half of the RSNO-modified xerogel coating was physically removed from the glass substrate and this interface probed to acquire film thickness.

Elemental analysis of RSNO Xerogels. The xerogel materials were analyzed for sulfur weight percent (S wt %) by Midwest Microlab, LLC (Indianapolis, Ind.).

Bacterial Assays. *P. aeruginosa* was cultured at 37° C. in tryptic soy broth (TSB), pelleted by centrifugation, resuspended in 15% glycerol (v:v in PBS), and stored at −80° C. Cultures for bacterial adhesion studies were grown from a −80° C. stock in 37° C. TSB overnight. A 1 mL aliquot of overnight culture was inoculated into 100 mL fresh TSB, incubated at 37° C. with rotation, and grown to a concentration of $10^8$ colony forming units (cfu) $mL^{-1}$ (verified by 10-fold serial dilutions in PBS, plating on tryptic soy agar nutrient plates, and subsequent cfu enumeration). The bacteria were pelleted by centrifugation, rinsed with ultrapure water, and resuspended in sterile PBS. Control (unnitrosated) and RSNO-modified xerogels were immersed in 4 mL aliquots of bacterial suspension and incubated at 37° C. in dark or light conditions (200 W at a distance of 0.6 in). Temperature was maintained during irradiation by circulating thermostatted water through a custom-made flow cell housing the samples. The xerogel substrates were removed from the bacterial suspension after 1 h and gently immersed in ultrapure water to dislodge loosely adhered cells. The slides were dried under a stream of $N_2$. To quantify bacterial adhesion, substrates were imaged in phase-contrast mode using a Zeiss Axiovert 200 inverted optical microscope (Chester, Va.) at 20× magnification. Digital micrographs were captured with a Zeiss Axiocam digital camera (Chester, Va.) and digitally processed to differentiate adhered cells from background. The darkened pixels, corresponding to adhered bacteria, were digitally enumerated with the extent of bacterial adhesion reported as the percent of the xerogel substrate surface covered with bacterial cells. The viable (still alive) bacteria adhered to the xerogel were determined by swabbing the non-xerogel-coated side of the slide with 70% EtOH and PBS to remove/kill adhered bacteria and residual EtOH, respectively. The slide was then placed in 4 mL of sterile PBS and bacteria adhered to the xerogel-coated side were removed from the substrate surface via sonication (40 kHz, 15 min).[36] The resulting bacterial suspensions were subjected to serial 10-fold dilutions in sterile PBS, and 100 μL aliquots of each dilution were plated on tryptic soy agar (TSA) nutrient plates. The plates were incubated at 37° C. overnight and the number of live bacteria was determined by counting the number of colonies that grew on each plate overnight.

Cytotoxicity. To assess the impact of xerogel fragmentation on healthy cells, L929 murine fibroblasts were exposed directly to the xerogel fragmentation solutions. Briefly, the fibroblasts were cultivated in DMEM supplemented with 10% fetal bovine serum (v/v), 100 units penicillin, and 100 μg streptomycin, then incubated in 5% $CO_2$/95% air under humidified conditions at 37° C. After attaining confluency, the cells were trypsinized and then seeded onto tissue-culture-treated polystyrene 96-well plates at a density of $1×10^5$ cells $mL^{-1}$. Three days later, the media was aspirated and replaced with 1:1 dilution of the fragmentation solutions with media for 24 h viability experiments, respectively. Subsequently, the solutions were aspirated, cells were washed with sterile PBS, and 100 μL of fresh media was added to the cells. Cellular viability was assessed using the MTS assay (CellTiter 96 Aqueous Non-Radioactive Cell Proliferation Assay; Promega, Madison, Wis.). Briefly, the MTS reagent (20 μL) was added to each well until a purple formazan color was formed in the control (untreated) wells. The supernatant from each well was then transferred to a new 96-well plate prior to reading the absorbance at 490 nm using a Labsystems Multiskan RC microplate reader (Helsinki, Finland). Viability was expressed as a percent viability relative to cells treated to control PBS solutions.

Results and Discussion

Figure 2:
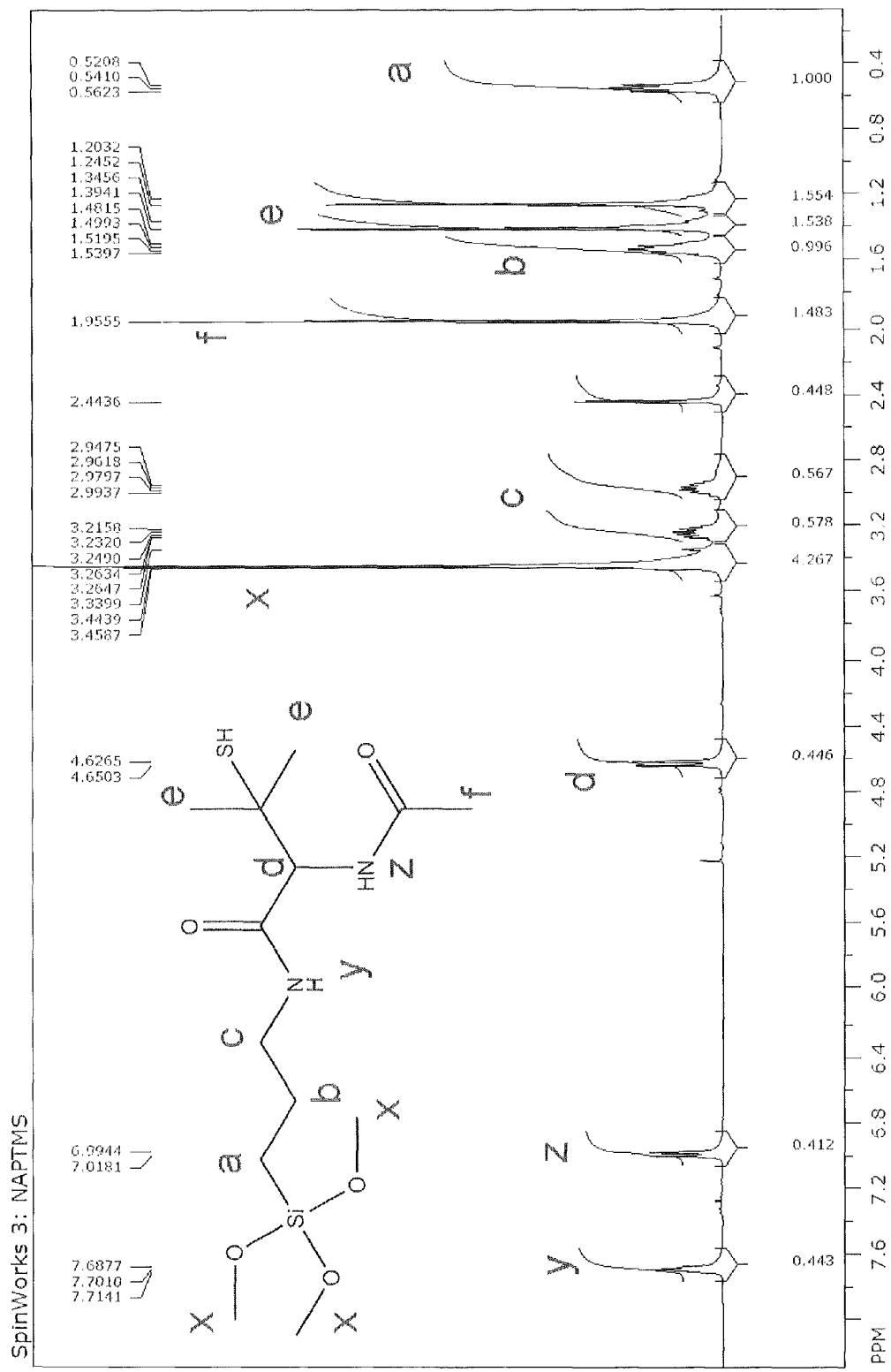
FIG. 2 provides an $^1$H NMR spectrum of the NAPTMS compound.

The preparation of tertiary thiol-based precursors was investigated for the development of biomedical devices/ therapeutics with continuous and photoactivatable NO release. A NAP thiolactone was thus synthesized to design such a precursor for the synthesis of NO-releasing xerogels. Penicillamine was reacted in the presence of acetic anhydride to generate the NAP thiolactone in situ. After characterization by $^1$H and $^{13}$CNMR, the NAP thiolactone was directly coupled with APTMS to result in a tertiary thiol-bearing silane, referred to as NAPTMS (see FIG. 1). Successful synthesis of this tertiary thiol-bearing silane was verified via $^1$HNMR characterization (FIG. 2).

Figure 3:
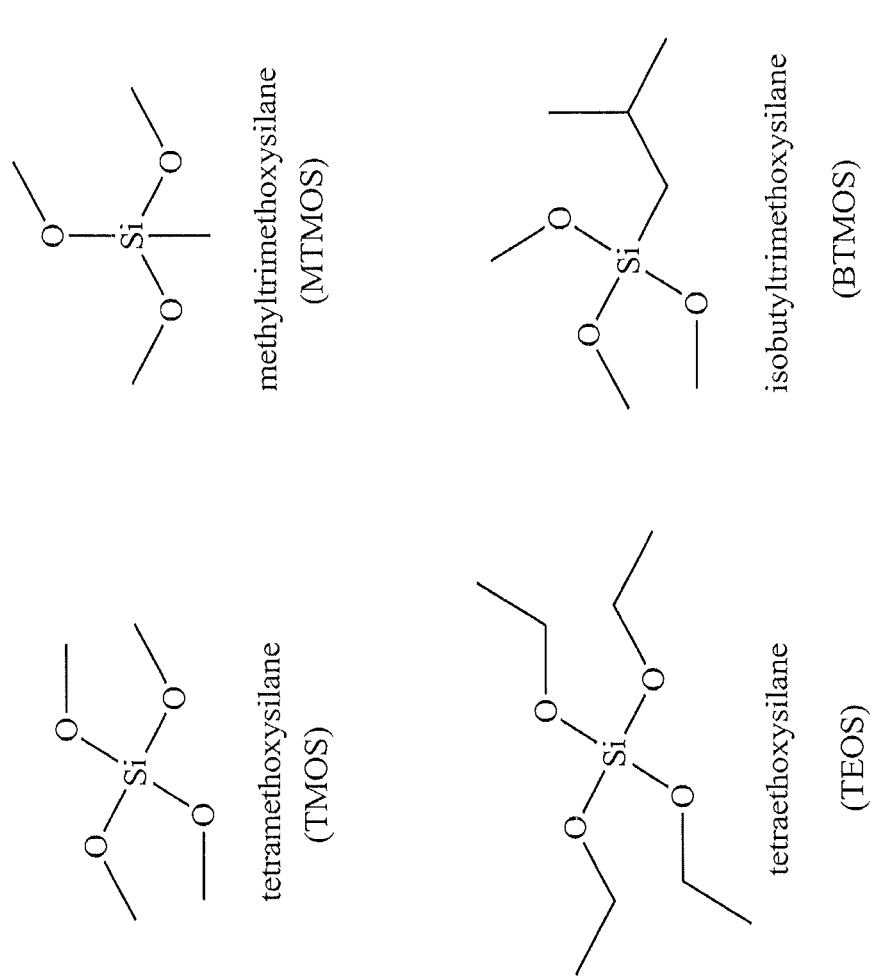
FIG. 3 provides the chemical structures of backbone alkylalkoxy- and alkoxysilanes.

Nitric oxide-releasing xerogels may be composed of organosilanes hydrolyzed and co-condensed with alkoxy- or alkylalkoxysilanes (termed "backbone silanes"). The backbone silanes impart both structural stability and tunable NO payloads by varying the silane molar ratio. Unfortunately, co-condensation of silanes is not a trivial objective. Disparate hydrolysis and condensation rates between mixed silanes impact xerogel formation, at times preventing it altogether. As NAPTMS is a novel silane with uncharacterized reaction rates, a systematic examination of the most favorable conditions to form NAPTMS-based xerogels was undertaken. Co-condensation of NAPTMS was attempted with backbones of varying structures and reaction rates (FIG. 3), including tetramethoxysilane (TMOS), tetraethoxysilane (TEOS), methyltrimethoxysilane (MTMOS), and isobutyltrimethoxysilane (BTMOS), to determine which composition allowed for suitable xerogel synthesis.

Initial investigations into the synthesis of tertiary thiol-modified films began with 40 mol % NAPTMS as a mid-range concentration to produce films that release significant amounts of NO while maintaining desirable physical characteristics (e.g., smooth, crack-free, and optically transparent). After being dried, these NAPTMS films appeared well-formed regardless of backbone identity. However, each composition became opaque when immersed in water. Such behavior may be attributed to the presence of unreacted silicate oil within the xerogel network, leading to phase separation from reacted silanes. Exposure of the xerogels to ethanol resulted in complete film dissolution as unreacted and partially reacted silanes were washed away, corroborating the hypothesis of incomplete xerogel formation. While not being bound to any particular theory, incomplete formation of 40 mol % NAPTMS xerogels is attributed to significant disparity between the slow condensation rate of NAPTMS, due to substantial steric hindrance around the silicon atom, and the more rapid reaction of the backbone silanes. Multiple synthetic parameters that influence silane reaction rates were varied to investigate this problem. Strategies such as altering the water to total silane ratio (1:4, 2:1, 4:1, 10:1, and 20:1) did not lead to improved stability, nor did modifications to the reaction time (0.5-5 h), acid catalyst concentration (0.01-0.20M), catalyst type (NaOH vs. HCl), ethanol solvent volume (25-1050 µL), drying time (0.25-5 d), or drying temperature (25-70° C.). In the end, the high concentration of NAPTMS (i.e., ≥40 mol %) was concluded to be prohibitive for xerogel formation under the wide range of conditions assessed.

Lowering the amount of NAPTMS in the sols resulted in stable xerogels. Films were formed by systematically adjusting a wide range of synthetic parameters in the xerogel synthesis using a model composition consisting of 20 mol % NAPTMS balanced with MTMOS. While not entirely stable, the initial 40 mol % NAPTMS films indicated that a 10:1 water to silane ratio resulted in slightly better formulations (i.e., xerogels turned less opaque in aqueous solution). This water to silane ratio (based on a 1 mmol total silane amount) was thus selected for study. The amount of acid catalyst may also influence the resulting xerogel formation.

NAPTMS-based xerogels synthesized with greater amounts of catalyst (i.e., 0.075 M HCl) led to non-uniform coatings and resulted in opaque xerogels with significant topographical heterogeneity. Reactions with lower amounts of catalyst (i.e., 0.025MHCl) did not adequately promote xerogel formation. However, films synthesized with 0.05M HCl had desirable properties. Diluting sols when fabricating xerogel coatings with highly viscous sols may ensure a homogenous casting solution. Based on these preliminary experiments, a large volume of ethanol (1054 µL) and an acid concentration of 0.05M were used for all subsequent investigations. Using this water to silane ratio and acid catalyst molarity, xerogel composition was varied by altering the backbone silane structure. Initially, films were formed using TMOS because of its similar hydrolysis/condensation kinetics to MTMOS, suggesting potential for well-formed films. Unfortunately, TMOS-derived solutions did not coat substrates uniformly and resulting xerogels fractured upon drying/curing. During xerogel drying, a meniscus at the vapor/liquid interface causes a pressure gradient within the polymer structure. If the network is not sufficiently pliant or porous to deal with such stress, evaporation may proceed non-uniformly and result in cracking. The inflexible and regimented silica network observed when using TMOS may be attributed to its four bridging ligands that enhance polymer crosslinking and interchain cohesion. The main strategy to decrease the pressure gradient and resulting xerogel fracture is to reduce the evaporation rate. However, applying this strategy (e.g., drying at 25° C.) to NAPTMS/TMOS xerogels still led to cracking.

The similarities in size and associated steric hindrance between TMOS and MTMOS suggest that another reason might be responsible for the successful film formation using MTMOS and failure (i.e., cracking) with TMOS. The incorporation of one nonhydrolyzable ligand when using MTMOS as compared to TMOS lessens steric constraints and interchain cohesion within the silica network and is the predominant factor for preparing films with high integrity upon drying MTMOS-based xerogels.

Varying the backbone from TMOS to TEOS represents a less significant alteration to the structure of the backbone (i.e., ethoxy instead of methoxy ligands at the silicon center) yet resulted in a significant improvement to xerogel stability and uniformity. The increase in steric hindrance that accompanies the increased carbon chain length effectively decreases the rate of hydrolysis and condensation under acid-catalyzed xerogel reactions. Successful xerogel formation in this instance likely results from similar kinetic rates of TEOS and NAPTMS, thus facilitating successful co-condensation. Similar to TMOS, TEOS features four bridging ligands and therefore should also form non-pliant networks. However, cracking was not observed in NAPTMS/TEOS xerogels. Successful xerogel formation may be attributed to more successful incorporation of NAPTMS within the network, affording greater flexibility of the network as a result of the nonhydrolyzable ligand. Additionally, reactions with TEOS produced films of greater integrity at shorter reaction times (i.e., 30 min vs. 1 h) than MTMOS. If the TEOS precursor retained a large degree of unhydrolyzed ligands due to the shorter reaction time, the resulting network would be more pliant and avoid fracture upon drying.

Increasing the size of the nonhydrolyzable ligand in the backbone silane from a methyl (MTMOS) to a branched isobutyl group (BTMOS) represents a large contribution to steric hindrance and should significantly decrease condensation rates for acid-catalyzed xerogel reactions. Akin to the 40 mol % NAPTMS films, xerogels derived from BTMOS exhibited incomplete co-condensation and xerogel formation. It can be assumed that although BTMOS and NAPTMS may have similarly matched reaction rates, both rates are too slow for adequate xerogel formation. Increasing the catalyst amount or the reaction time to promote reaction between the two silanes did not improve xerogel stability for BTMOS-based films.

Since the NAPTMS concentrations were ideally ≤30 mol %, alternative strategies were investigated to increase/tune NO release kinetics and payloads. We thus focused on increasing the amount of sol cast per surface area of substrate. To evaluate xerogel thickness and NAPTMS concentration as means of affecting NO release, 30-120 µL aliquots of 10, 20, and 30 mol % NAPTMS compositions with either TEOS or MTMOS were cast on glass substrates. Marked differences in xerogel stability were observed for the variations in mol %, casting volume, and backbone.

Xerogels formed from casting volumes >60 µL cracked upon drying regardless of backbone identity or mol %. An upper threshold was expected as increasing the thickness would contribute to an enhanced pressure gradient within the xerogel that causes fracturing upon drying. Unfortunately, 10 mol % NAPTMS balance MTMOS compositions were opaque and did not uniformly coat substrates. These films were stable in ethanol, indicating that xerogel formation was complete despite the opacity. Thus, the opacity is attributed to microsyneresis or the clustering of the silica network that results in phase separation from the residual solvent. Xerogels lacking optical transparency are considered undesirable if photoinitiated NO release is the intended application of such materials. While 30 µL cast from a 20 mol % NAPTMS balance MTMOS composition formed glassy, homogenous films (7.84±0.91 µm), 45 and 60 µL casts were similar in opaque appearance to the 10 mol % compositions. Xerogels consisting of 30 mol % NAPTMS balance MTMOS at 30, 45, and 60 µL casting volumes formed, optically transparent xerogels with resulting thicknesses of 10.03±1.42, 15.43±2.28, and 19.05±2.05 µm, respectively.

Similarly, ideal TEOS films were formed using 20 mol % NAPTMS at 30, 45, and 60 µL casting volumes and 30% NAPTMS at 30 µL cast with corresponding thicknesses of 8.65±0.81, 14.35±0.34, 19.33±3.32, and 10.28±1.95 µm, respectively. Greater casting volumes for the 30% NAPTMS balance TEOS films exhibited cracking upon drying. Compositions derived from 10 mol % NAPTMS balance TEOS cracked upon drying as well, ostensibly due to an excessive concentration of TEOS in the silica network causing a lack of pliancy within the xerogel framework. Altogether, eight stable xerogel formulations composed of NAPTMS/MTMOS and NAPTMS/TEOS as a function of silane mol % and casting volumes were further investigated as novel NO-releasing photoantimicrobial surfaces.

Thiols are readily converted to NO donor form (i.e., RSNOs) by exposure to nitrosating agents such as nitrous acid (commonly generated in situ from acidified nitrite solutions). S-Nitrosothiol formation is accompanied by a color change with primary RSNOs red in appearance and tertiary RSNOs green. Thus, characteristic RSNO absorbance bands in the UV (330-350 $n_O \rightarrow \pi^*$) and visible (550-600 nm; $n_N \rightarrow \pi^*$) regions are used to monitor RSNO formation. Initial UV/vis spectroscopy studies indicated that optimal nitrosation of the NAPTMS-derived films required a 100-fold molar excess of acidified nitrite.

Figure 4:
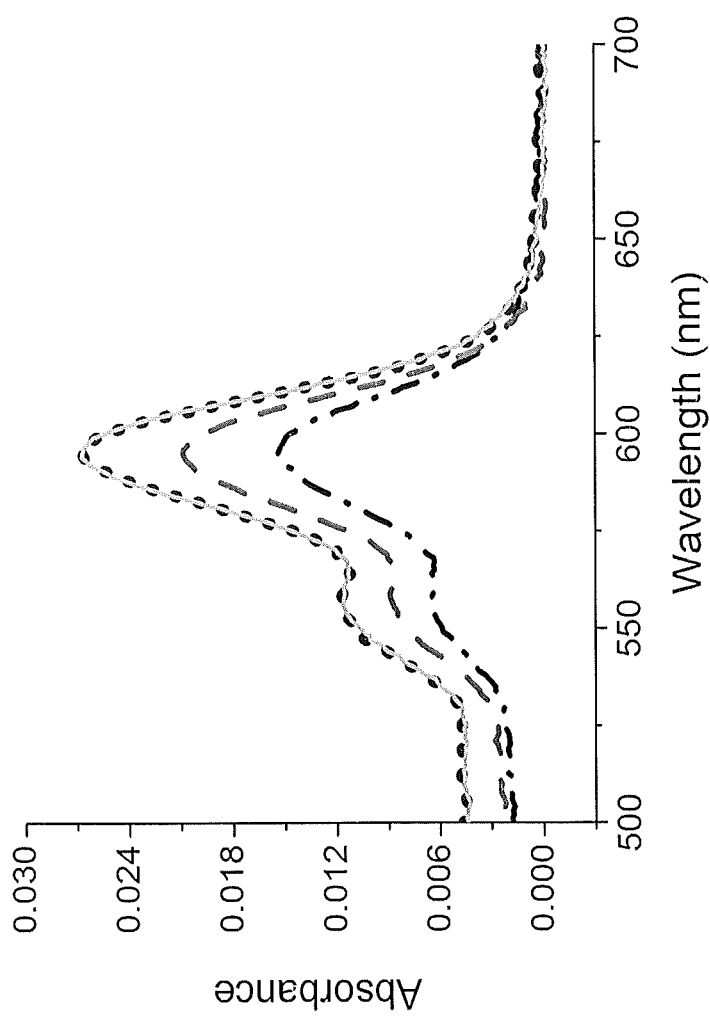
FIG. 4 provides an absorbance spectrum of a 20 mol % NAPTMS balance MTMOS (30 cast) xerogel film after 1 (dashed dotted black line), 2 (dashed red line), 3 (dotted blue line) and 4 h (solid green line) of nitrosation in a 100× molar excess (vs. thiols) of acidified nitrite.

The optimal nitrosation time was studied as a function of backbone and casting volume and determined after absorbance at 590 nm no longer increased, indicating extent of nitrosation had ceased. As shown in FIG. 4, the degree of nitrosation was not enhanced with reaction times >3 h for the MTMOS-based films (casting volume of 30 µL). Identical analysis revealed that 45 and 60 µL casts of MTMOS-based films (regardless of NAPTMS mol %) required slightly longer reaction time (4 h), presumably due to slowed diffusion of the nitrosating agent through the thicker coatings. Xerogels derived from TEOS reacted more rapidly and were nitrosated to a maximum extent after 1 h incubation, regardless of casting volume. The difference between TEOS and MTMOS may be attributed to the less organic character associated with TEOS-based network that facilitates more rapid penetration of the aqueous nitrosating agent within the xerogel network.

Although more stable than their primary counterparts, tertiary RSNOs still undergo decomposition (and NO release) by typical RSNO pathways including thermal and photolytic-based S—NO cleavage and copper ion-mediated reduction. However, minimal amounts of "free" copper ions are found physiologically, suggesting this method of NO release may be physiologically irrelevant. While previous primary RSNO-modified xerogels exhibited NO release that had a slight dependence on copper ion concentration, thermal and photo-initiated fluxes led to more substantial NO. Due to this knowledge and the intended photoinitiated release of NO from these tertiary RSNO-modified xerogels, the effect of copper on NO release was deemed extraneous. Accordingly, trace copper ions in PBS buffer were chelated with diethylenetriaminepentaacetic acid (DTPA) to inhibit any Cu-ion mediated decomposition when characterizing the NO release of these films.

Figure 5:
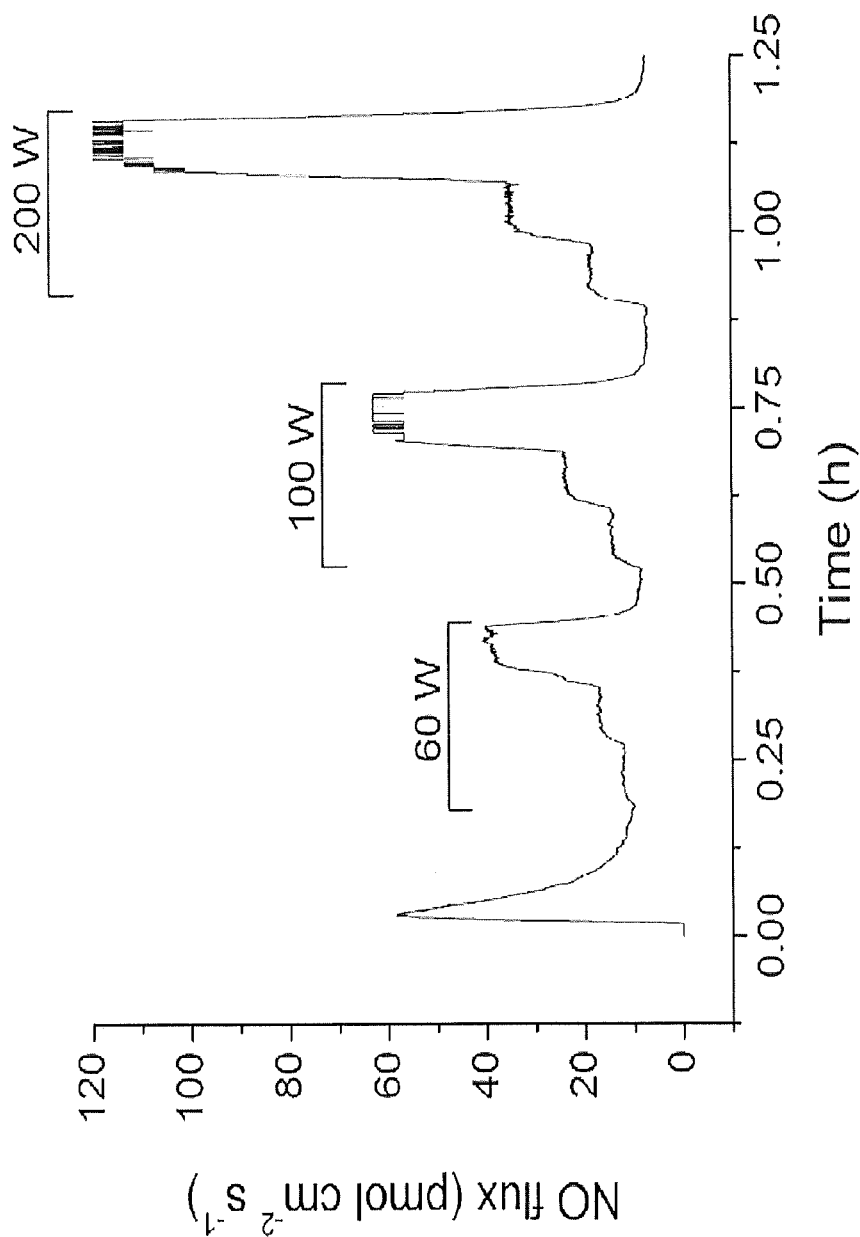
FIG. 5 shows the nitric oxide flux from a 30 mol % NAPTMS balance TEOS (30 μL cast) xerogel at 37° C. and under periods of visible irradiation. Increasing bulb wattages are noted. Successive steps under each period of irradiation correspond to distances between the light source and sample of 0.9, 0.6, and 0.3 m.

Photoinitiated NO release from RSNO-modified xerogels was measured in real time using chemiluminescence. Individual films were immersed in 500 µM DTPA (pH 7.4 PBS) at 37° C. As expected, exposure to visible irradiation greatly influenced the NO release from the coatings. As shown in FIG. 5, the NO flux from a representative xerogel film (30 mol % NAPTMS balance TEOS, 30 µL cast) increased with both greater bulb wattage and decreasing distance between the lamp and sample flask. The rapid NO release kinetics associated with the 200 W light at a distance of 0.3 m were ideal for quantifying the total amount of NO stored within the films. A period of 16 h of irradiation under these conditions was sufficient to completely liberate all of the NO from the films as indicated by both a return to baseline on the instrument and the absence of a greenish hue within assayed films.

To aid in comparison among different compositions as well as previous materials, two criteria should be met when reporting the total NO storage. The total should be reported relative to the surface area of the coating as well as normalized per mass of deposited material. As shown in Table 1, the tertiary RSNO-modified xerogels were found to store 0.20-0.62 µmol NO per mg of material.

TABLE 1

Total NO stored, sulfur content, and degree of thiol to S-nitrosothiol conversion for tertiary RSNO-modified xerogels.

| (mol %) | Backbone | (µL) | (µmol cm$^{-2}$) | (µmolmg$^{-1}$) | (weight %) | conversion efficiency (%) |
|---|---|---|---|---|---|---|
| 20 | TEOS | 30 | 1.02 ± 0.26 | 0.25 ± 0.06 | 3.89 | 20.2 |
| 20 | TEOS | 45 | 1.16 ± 0.44 | 0.20 ± 0.08 | 3.89 | 16.9 |
| 20 | TEOS | 60 | 1.48 ± 0.29 | 0.24 ± 0.05 | 3.89 | 19.9 |
| 30 | TEOS | 30 | 1.78 ± 0.09 | 0.62 ± 0.03 | 5.05 | 39.2 |

TABLE 1-continued

Total NO stored, sulfur content, and degree of thiol to S-nitrosothiol conversion for tertiary RSNO-modified xerogels.

| (mol %) | Backbone | (µL) | (µmol cm$^{-2}$) | (µmol mg$^{-1}$) | (weight %) | conversion efficiency (%) |
|---|---|---|---|---|---|---|
| 20 | MTMOS | 30 | 0.87 ± 0.31 | 0.31 ± 0.11 | 2.51 | 39.3 |
| 30 | MTMOS | 30 | 1.13 ± 0.23 | 0.47 ± 0.10 | 4.57 | 32.9 |
| 30 | MTMOS | 45 | 1.22 ± 0.48 | 0.27 ± 0.11 | 4.57 | 19.1 |
| 30 | MTMOS | 60 | 1.64 ± 0.39 | 0.28 ± 0.07 | 4.57 | 19.9 |

Of note, the mass-normalized NO storage was not equivalent at different casting volumes of the same composition. For example, 30 mol % NAPTMS/MTMOS compositions stored 0.47±0.10 µmol mg$^{-1}$ when cast at 30 µL (~5 mg of xerogel upon drying), but only 0.28±0.07 µmol mg$^{-1}$ when 60 µL was cast (~12 mg of deposited material). Although nitrosation times were optimized for individual casting volume, this non-linearity indicates the extent of nitrosation for each film differs and is presumably limited by casting volume (thickness). For example, thiols located within the interior of the coating may be inaccessible to the nitrosating agent.

Although thicker films stored less NO per mass of identical xerogel for all compositions, the difference was more pronounced for MTMOS-derived films. This was somewhat expected as these films also required different nitrosation times dependent on casting volume, whereas TEOS-based films reached optimal nitrosation at equivalent times regardless of casting volume. Nevertheless, the variation in NO storage per mass was small enough such that when total NO storage is normalized to surface area of coating, a clear correlation was observed between xerogel thickness and NAPTMS mol % (Table 1). Increasing either the thickness or NAPTMS concentration of the coating enhanced NO storage to the range of 0.87-1.78 µmol cm$^{-2}$. When comparing equivalent concentrations of NAPTMS and casting volumes, the TEOS-based films stored slightly more NO than MTMOS-based films. The large reservoirs of NO stored within these coatings are comparable to previously reported NO-releasing xerogels that have shown efficacy in reducing bacterial adhesion, fighting infection, and mitigating the foreign body response, illustrating the biomedical potential of these tertiary RSNO-modified xerogels.

To confirm that the degree of nitrosation varied for each composition, elemental analysis of the films was used to deduce the amount of sulfur in the xerogels. As provided in Table 1, 20 mol % NAPTMS balance TEOS films consisted of 3.89 wt % sulfur while the equivalent MTMOS counterpart contained 2.51 wt % sulfur. Likewise, the 30 mol % NAPTMS xerogels contained 5.05 and 4.57 wt % for films formed with TEOS and MTMOS, respectively. As shown in Table 1, nitrosation efficiencies for 20 mol % NAPTMS/TEOS films were ~17-20% regardless of casting volume. Increasing the NAPTMS concentration to 30 mol % resulted in a greater nitrosation efficiency (~39%), suggesting that higher thiol incorporation increases thiol accessibility to the nitrosating agent (i.e., nearer to the surface). Xerogels derived from MTMOS were characterized by similar conversion efficiencies at 20 and 30 mol % NAPTMS, but the nitrosation efficiency decreased for greater casting volumes (i.e., ~33 vs. ~20% for 30 and 60 µL casting volume, respectively). These results again indicate that thicker films limit the extent of nitrosation, due most likely to the dense structure of the xerogel and a large degree of thiols being solvent inaccessible.

One motivation for employing tertiary RSNO-modified xerogels as photoantimicrobials is that the enhanced stability may negate substantial thermal decomposition leading to NO release in the absence of light. To verify such thermal stability, NO fluxes were measured from xerogels immersed in 500 µM DTPA (pH 7.4 PBS) at 37° C. without light. As expected, little if any NO was released under these conditions (see Table 2).

TABLE 2

Nitric oxide flux from tertiary RSNO-modified films at 37° C. and in the dark.

| NAPTMS (mol %) | Backbone | Casting volume (µL) | Nitric oxide flux (pmol cm$^{-2}$ s$^{-1}$) | | | | | | | | |
|---|---|---|---|---|---|---|---|---|---|---|---|
| | | | 0 h | 1 h | 6 h | 12 h | 1 d | 2 d | 3 d | 5 d | 1 week |
| 20 | TEOS | 30 | 21.6 ± 0.7 | 2.20 ± 0.02 | 1.23 ± 0.06 | 0.55 ± 0.01 | 0.25 ± 0.01 | 0.43 ± 0.01 | 0.29 ± 0.01 | 0.28 ± 0.01 | 0.22 ± 0.01 |
| 20 | TEOS | 45 | 18.5 ± 0.6 | 2.90 ± 0.50 | 1.84 ± 0.02 | 0.87 ± 0.02 | 0.54 ± 0.08 | 0.40 ± 0.03 | 0.31 ± 0.01 | 0.40 ± 0.01 | 0.29 ± 0.01 |
| 20 | TEOS | 60 | 31.9 ± 1.0 | 3.95 ± 0.04 | 2.73 ± 0.03 | 1.29 ± 0.02 | 0.97 ± 0.02 | 0.67 ± 0.01 | 0.44 ± 0.01 | 0.37 ± 0.01 | 0.31 ± 0.01 |
| 30 | TEOS | 30 | 40.0 ± 0.5 | 2.70 ± 0.03 | 2.07 ± 0.02 | 1.27 ± 0.02 | 1.17 ± 0.02 | 0.91 ± 0.01 | 0.51 ± 0.01 | 0.39 ± 0.01 | 0.41 ± 0.01 |
| 20 | MTMOS | 30 | 6.3 ± 0.9 | 3.05 ± 0.03 | 2.03 ± 0.02 | 1.44 ± 0.03 | 0.95 ± 0.02 | 0.72 ± 0.01 | 0.61 ± 0.01 | 0.38 ± 0.10 | 0.22 ± 0.05 |
| 30 | MTMOS | 30 | 9.5 ± 0.7 | 2.10 ± 0.02 | 1.86 ± 0.04 | 1.26 ± 0.02 | 0.83 ± 0.02 | 0.61 ± 0.01 | 0.52 ± 0.01 | 0.60 ± 0.01 | 0.28 ± 0.07 |
| 30 | MTMOS | 45 | 30.3 ± 6.8 | 2.07 ± 0.02 | 2.32 ± 0.04 | 1.38 ± 0.02 | 0.89 ± 0.02 | 0.80 ± 0.03 | 0.58 ± 0.01 | 0.49 ± 0.01 | 0.39 ± 0.01 |
| 30 | MTMOS | 60 | 26.9 ± 2.0 | 2.26 ± 0.02 | 2.26 ± 0.03 | 1.67 ± 0.02 | 1.33 ± 0.03 | 0.91 ± 0.01 | 0.61 ± 0.01 | 0.66 ± 0.01 | 0.51 ± 0.01 |

Any initial NO release (~6-40 pmol cm$^{-2}$ s$^{-1}$) rapidly subsided within 10 min to fluxes <4 pmol cm$^{-2}$ s$^{-1}$. The initial NO release is attributed to RSNO decomposition resulting from the sudden temperature increase when films at room temperature are immersed in 37° C. PBS. The fluxes monitored over the one week period proved to be stable yet low, dropping to <1 pmol cm$^{-2}$s$^{-1}$ for all compositions after 48 h. After 7 d at 37° C. in the dark, the xerogels released 0.24-0.54 µmol NO per cm$^{-2}$, corresponding to an average of ~32% of the total NO storage. Shorter periods (i.e., 24 h) resulted in an average of only ~11% of the NO reservoir being depleted, illustrating a stronger than expected thermal stability for the RSNO-modified films. Furthermore, xerogels still retained their greenish hue (indicative of tertiary RSNOs) after 1 week of soaking at these conditions with irradiation of these xerogels at that time resulting in NO liberation with fluxes comparable to freshly nitrosated xerogels (data not shown).

Figure 6:
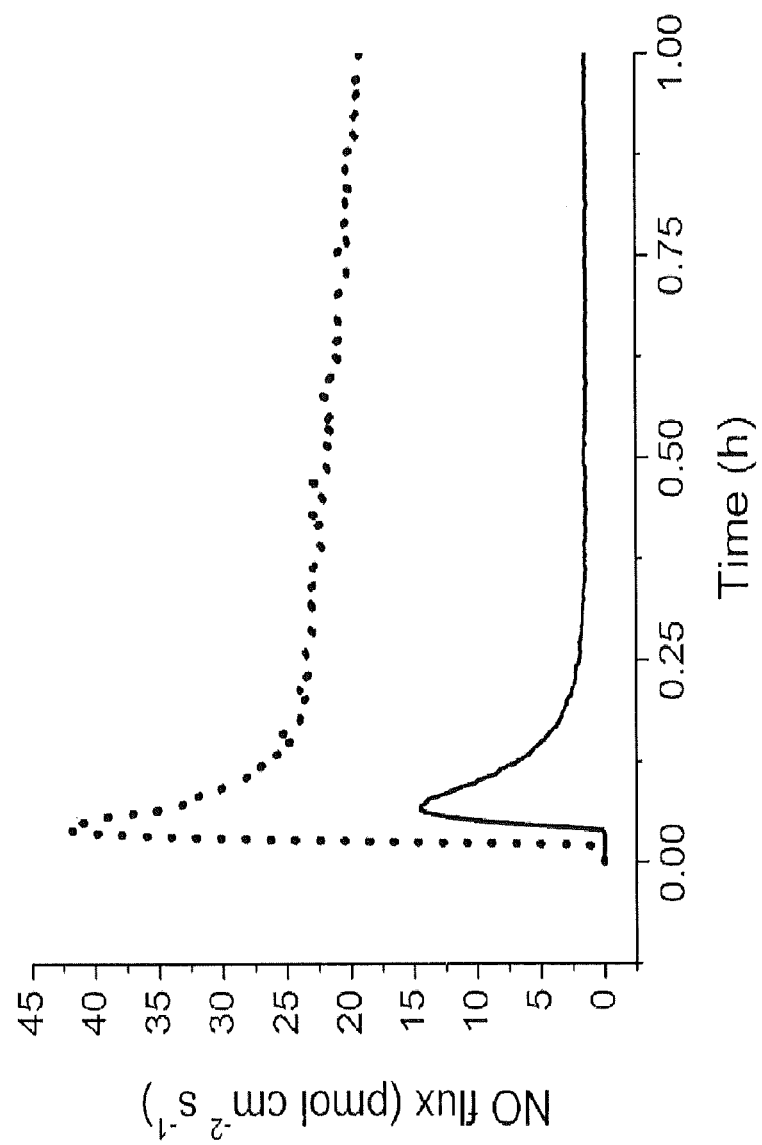
FIG. 6 shows nitric oxide flux from a 20 mol % NAPTMS balance TEOS (30 μL cast) xerogel at 37° C. in the dark (solid line) and irradiated with 200 W light at a distance of 0.6 m (dotted line).

Photoinitiated NO release due to a 200 W light at a distance of 0.6 m above the sample was assessed at physiological temperature maintained via circulating water from a thermostatted bath shielded from direct irradiation. As shown in Table 2, the average NO flux over 1 h of irradiation was steady for each composition (21.9-39.0 pmol cm$^{-2}$ s$^{-1}$). When compared to the average NO fluxes for identical compositions assayed in the dark, a marked contrast is observed as illustrated in FIG. 6. Photoactivation enhanced NO release from the materials by an order of magnitude compared to the strictly thermally-induced fluxes (Table 3).

TABLE 3

Average NO flux from RSNO-modified xerogels over 1 h at 37° C. either irradiated or in the dark.

| NAPTMS (mol %) | Backbone | Casting volume(µL) | Nitric oxide flux (pmol cm–2 s–1) | |
|---|---|---|---|---|
| | | | 200 W irradiation | Dark |
| 20 | TEOS | 30 | 22.7 ± 3.0 | 2.7 ± 0.4 |
| 20 | TEOS | 45 | 27.3 ± 3.2 | 3.4 ± 0.4 |
| 20 | TEOS | 60 | 27.4 ± 3.6 | 4.2 ± 0.4 |
| 30 | TEOS | 30 | 39.0 ± 6.5 | 3.2 ± 0.5 |
| 20 | MTMOS | 30 | 23.8 ± 2.4 | 3.3 ± 0.1 |
| 30 | MTMOS | 30 | 21.9 ± 2.1 | 2.3 ± 0.2 |
| 30 | MTMOS | 45 | 22.4 ± 2.3 | 2.3 ± 0.2 |
| 30 | MTMOS | 60 | 28.0 ± 2.9 | 2.5 ± 0.2 |

While increasing mol % and casting volume (i.e., xerogel thickness) led to slight increases in the observed NO fluxes, the backbone identity had seemingly no effect on light-induced NO fluxes from the xerogels. In general, the photoinitiated fluxes were comparable across all compositions. Thus, the variation in mol % and casting volume seemingly has a greater impact on the total reservoir of stored NO rather than the achievable fluxes under irradiation. Methods to achieve varied fluxes include alterations to irradiation intensity (FIG. 5).

The structural stability of a biomaterial is important to its potential utility for a particular biomedical application. The stability of the xerogel films was thus evaluated by soaking the RSNO-modified coatings in pH 7.4 PBS for 1 week. Film degradation was evaluated at specific intervals by monitoring the silicon concentration in solution using ICP-OES.

In this manner, observed silicon in the soak solutions would represent fragmentation or instability of the siloxane bonds constituting the xerogel network. As the xerogels were cast on glass substrates, a measurable background of silicon was expected for controls. Surprisingly, the background measured for control xerogels was lower than glass alone (blanks). This behavior was attributed to the xerogels masking ~50% of the surface of the substrates and reducing leached silicon from the glass. To control for this when assessing the fragmentation of tertiary RSNO-modified xerogels, both bare glass substrates and glass substrates coated with polyurethane (a non Si-containing polymer) were employed as controls. As expected, the polyurethane-coated films exhibited roughly half the silicon observed for glass slides alone up to 24 h, after which the difference was narrower due to delamination of the polyurethane from the glass substrate. Thus, the polyurethane-coated substrates are more suitable controls and were used for background correction to quantify xerogel leaching.

Figure 7:
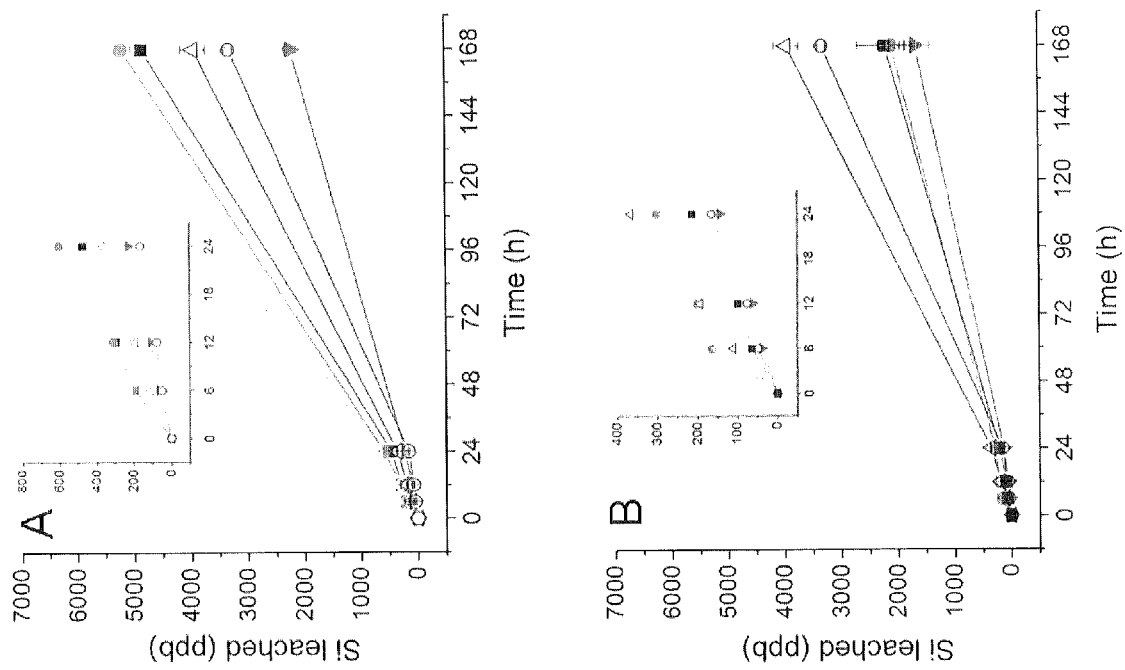
FIG. 7 shows the fragmentation for (A) TEOS and (B) MTMOS-derived xerogels during soaking in PBS at 37° C. for 1 week. Controls of uncoated glass substrates (open triangle) and glass substrates coated with polyurethane (open circles) were treated similarly. The compositions are as follows: (A) 20 mol % NAPTMS, 30 μL cast (black square), 45 μL cast (red circle), and 60 μL cast (green triangle); 30 mol % NAPTMS, 30 μL cast (blue inverted triangle). (B) 20 mol % NAPTMS, 30 μL cast (blue inverted triangle); 30 mol % NAPTMS 30 μL cast (black square), 45 μL cast (red circle), and 60 μL cast (green triangle). Measurements are mean ±SD for n=3.

More leaching due to xerogel instability was observed for thicker xerogel coatings (controlled by casting volumes). As shown in FIG. 7, xerogels formed using 60 µL of sol exhibited the most fragmentation for both backbone groups. Coatings derived from TEOS exhibited greater fragmentation than MTMOS-based films. The presence of the methyl group on MTMOS likely sterically hinders cleavage of the siloxane backbone and provides one less hydrolyzable ligand in the network. Additionally, the longer reaction time for MTMOS-based films may contribute to enhanced condensation and stability compared to TEOS-based films.

Figure 8:
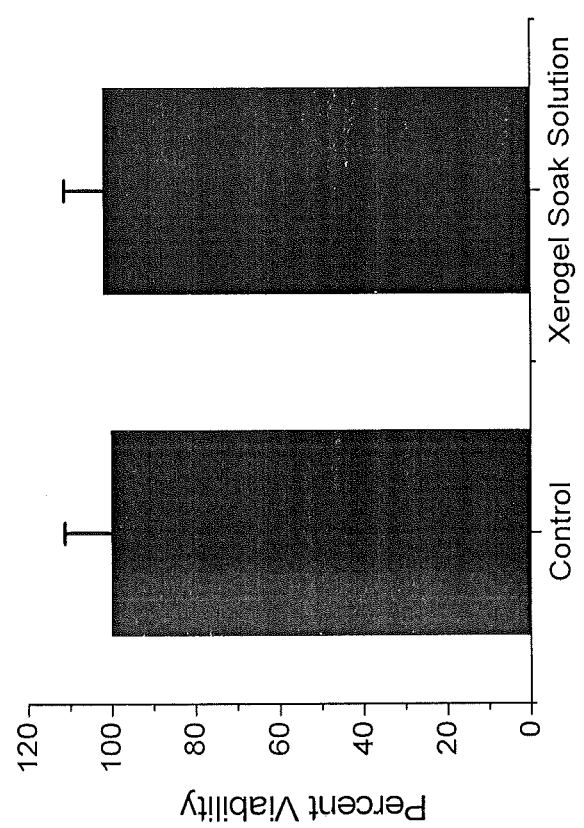
FIG. 8 shows cytotoxicity of control (PBS) and 20 mol % NAPTMS balance TEOS (60 μL cast) xerogel soak solution against L929 mouse fibroblast cells as measured via the MTS assay after 24 h exposure.

Although some silicon leached from the xerogels, the level of leaching was still less than controls at 24 h with the exception of the 20 mol % NAPTMS/TEOS compositions. Longer incubation times (i.e., 7 d) resulted in greater observed leaching for all materials and controls. After 7 d PBS immersion, the MTMOS-based films were still characterized by less leaching than controls, while the 20 mol % NAPTMS/TEOS films leached up to 2.4 ppm silicon into solution at levels proportional to the thickness. Visual inspection of the films after this soaking verified material instability for the xerogels cast from 60 µL. However, those of 30 and 45 µL casting volumes appeared intact, implicating the detected silicon to be due to microleaching and not a major detriment to material stability. Nevertheless, the potential toxicity of this minimal degree of xerogel fragmentation was evaluated. The fragmentation soak solution of the least stable composition, 20 mol % NAPTMS balance TEOS 60 µL cast, was diluted to 2. 4 ppm silicon with cell culture media to match the actual amount of silicon leached from just xerogel fragmentation and not background silicon from the substrate. The solution was incubated with L929 mouse fibroblast cells for 24 h, after which cell viability was assessed. The amount of fragmentation did not result in any loss to viability as compared to control cells in PBS and media (FIG. 8).

The shelf-life of NO-releasing xerogels was evaluated as a function of storage conditions to assess the suitability of these materials for future applications and clinical potential. As NO release is photoinitiated from these materials, exposure to ambient light during storage may reduce the material's NO release capacity. Moreover, thermally-induced NO release may still prove to be a factor even for tertiary-derived RSNOs for extended storage periods. If appreciable levels of NO were liberated (either photolytically or thermally) in the presence of oxygen, the formation of $NO_2$ and $N_2O_3$ would result, making the autocatalytic decomposition of RSNOs by $N_2O_3$ a concern.

Figure 9:
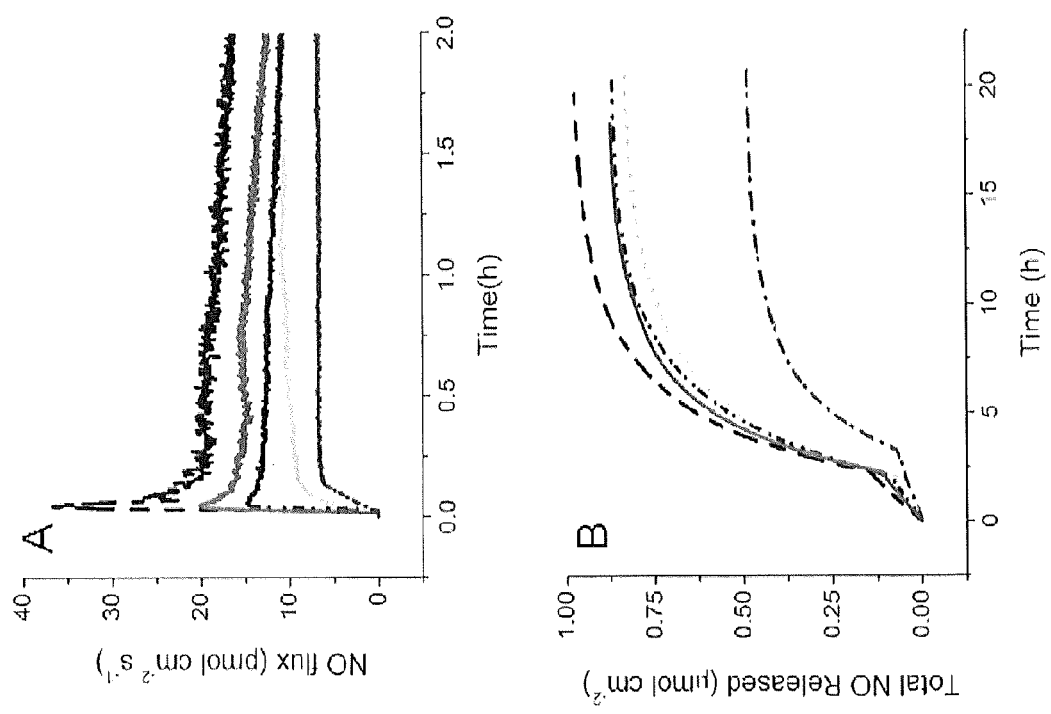
FIG. 9 shows the effect of various storage conditions on (A) NO flux and (B) total NO released for 20 mol % NAPTMS (balance TEOS, 30 μL cast) xerogels after 30 d under the following conditions: in vacuo dark and −20° C. (black dashed line); in ambient air dark and −20° C. (purple solid line); in vacuo dark and room temperature (blue dash dot dotted line); in ambient air dark and room temperature (green dotted line); and in ambient air ambient light and room temperature (red dash dotted line).

The effects of ambient light exposure, temperature, and under vacuum on NO payload after 30 d of storage were thus tested to evaluate the shelf life of RSNO-modified 20 mol % NAPTMS balance TEOS (30 µL cast) xerogels. As shown in FIG. 9, storage in vacuo in the dark at –20° C. were effective at preserving RSNO functionalities; xerogels stored in this manner exhibited the greatest NO fluxes and payloads. RSNO-modified xerogels stored at ambient pressure in the dark at –20° C. resulted in a slight decrease in both achievable NO fluxes (9A) and payloads (9B). Storage in vacuo in the dark and room temperature further decreased the available NO, yet yielded similar total NO storage to conditions of ambient pressure in the dark at –20° C.

Lastly, films stored at ambient pressure in the dark and room temperature were characterized as having slightly less NO storage capacity. Overall, the total NO released for xerogels stored under these conditions were not vastly different from each other. As expected, the storage of films at ambient pressure in ambient light and room temperature was the most detrimental to NO storage and flux. As a whole, the results suggest that light exposure even at ambient levels most negatively affects long-term stability. The presence of oxygen is only problematic if sufficient NO is generated to result in autocatalytic decomposition of RSNO groups by $N_2O_3$. Due to the stability of the tertiary RSNO to thermally-induced cleavage, the levels of NO generated via this pathway were minimal at room temperature and did not lead to significant additional NO loss. The only means where enough NO was generated in the presence of oxygen to drastically reduce the stored NO was ambient light exposure. While long-term tertiary RSNO-modified xerogel stability would benefit from storage under anaerobic conditions at reduced temperatures, protection from light is the most pressing condition that should be met to ensure sufficient NO donor stability within xerogels.

Figure 10:
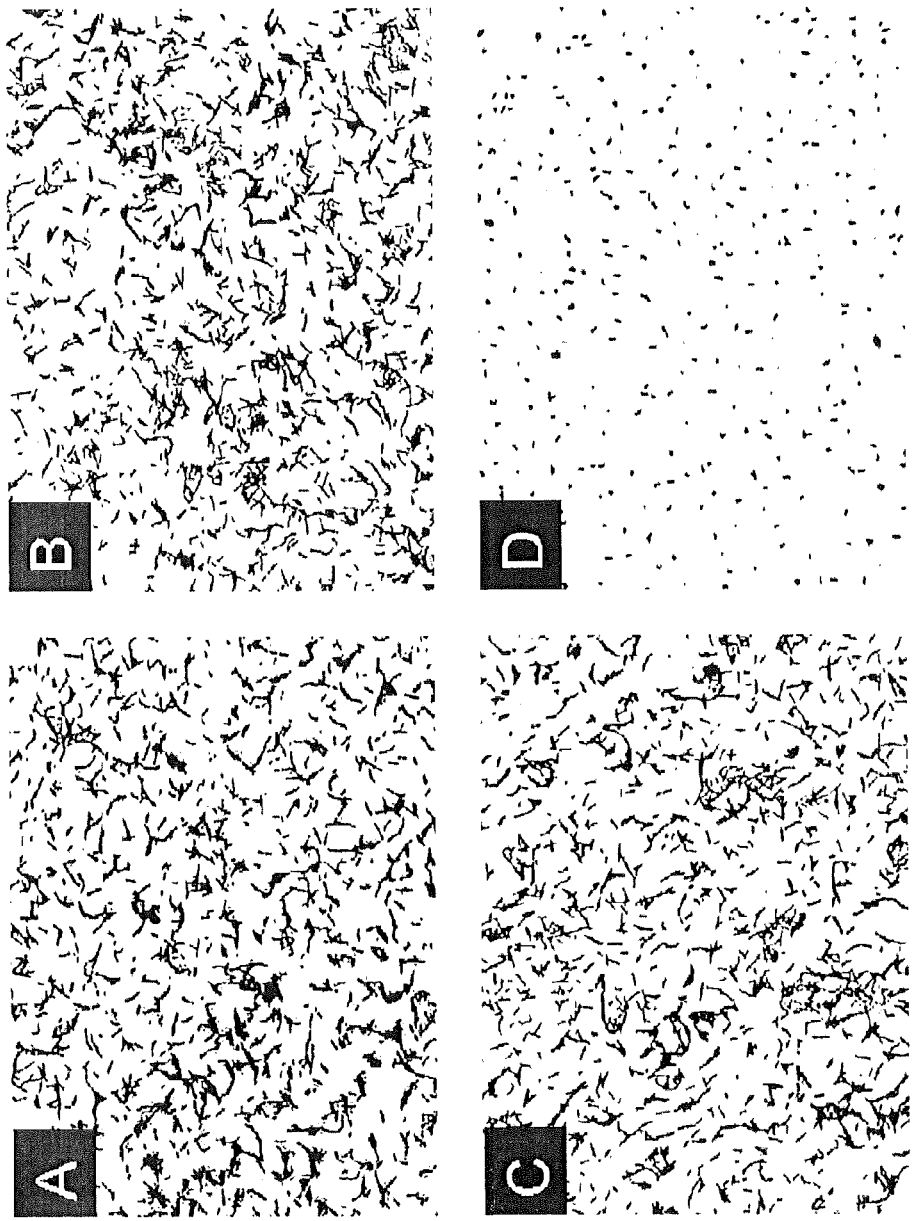
FIG. 10 provides representative optical micrographs of bacterial adhesion to unnitrosated control (A, B) and RSNO-modified (C, D) xerogels at 37° C. in the dark (A, C) and under irradiation (B, D). Black regions are the adhered bacteria.

The xerogels described here exhibit light-initiated fluxes exceeding ~20 pmol NO $cm^{-2}s^{-1}$, indicating their potential to reduce bacterial adhesion. To evaluate the anti-fouling potential of these materials, we investigated the antibacterial adhesion properties for a model composition (20 mol % NAPTMS balance TEOS, 30 µL cast) under various NO release conditions. P. aeruginosa ($10^8$ CFU $mL^{-1}$) were incubated under static conditions (i.e., non-nutrient, PBS) with nitrosated and control (unnitrosated) xerogels for 1 h at 37° C. either with exposure to 200 W irradiation (at a distance of 2 ft) or in the dark. The extent of bacterial adhesion was subsequently determined by phase-contrast optical microscopy. Light irradiation itself did not reduce bacterial adhesion to control xerogels (FIG. 10). The minimal NO release from the RSNO-modified.xerogels in the dark proved ineffective at reducing bacterial adhesion as expected for NO fluxes below the previously determined thresholds capable of reducing bacterial adhesion.

Figure 11:
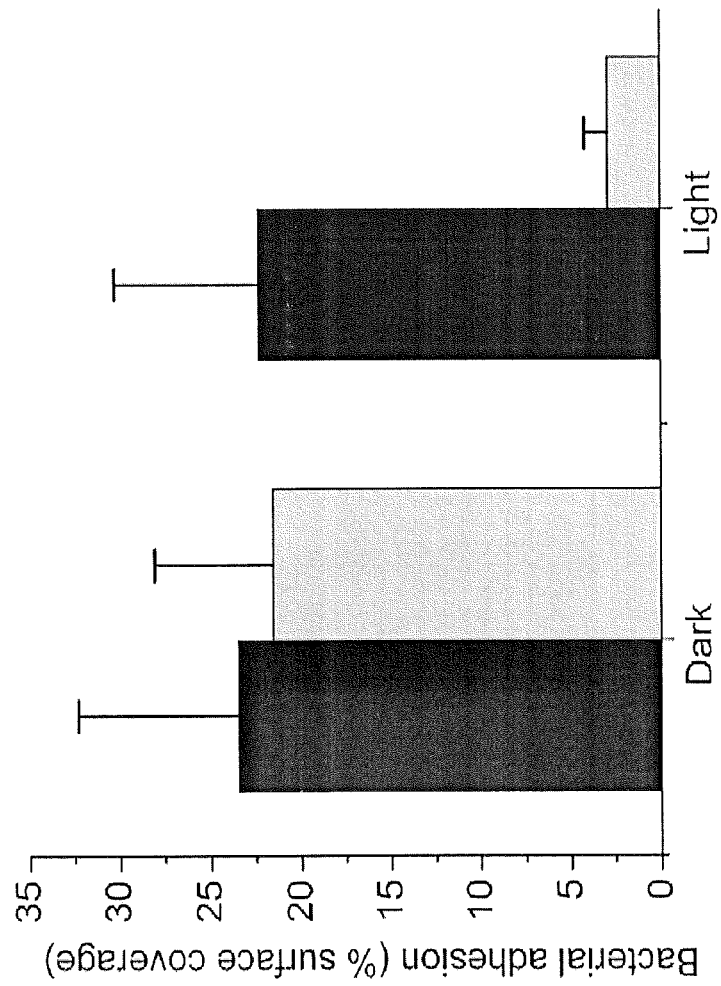
FIG. 11 shows *P. aeruginosa* adhesion to control, unnitrosated (dark) and RSNO-modified (light gray) 20 mol % NAPTMS balance TEOS (30 μL cast) xerogels at 37° C. in the dark or under irradiation. Bacterial adhesion reported as percent surface coverage.

Upon exposing the RSNO-modified xerogels to visible irradiation, the observed bacterial adhesion was significantly reduced relative to controls. Indeed, bacterial adhesion was reduced by 88, 87, and 87% on RSNO-modified xerogels in the presence of light when compared to controls under irradiation, controls in the dark, and RSNO-modified xerogels in the dark, respectively (FIG. 11). Clearly, the decrease in bacterial adhesion is solely due to the photoinitiated release of NO. To verify the antibacterial efficacy, the viability of adhered bacteria was also assessed. A significant reduction in bacterial viability was only observed for the RSNO-modified xerogels under irradiation, corroborating the photoantimicrobial efficacy of these films (Table 4).

TABLE 4

Bacterial viability of adhered bacteria to either control (unnitrosated) or RSNO-modified xerogels under various conditions at 37° C.

| | Bacterial Viability (CFU $mL^{-1}$) | |
|---|---|---|
| | 200 W irradiation | Dark |
| Control | 4.0 (±2.3) × $10^5$ | 6.2 (±1.5) × $10^5$ |
| RSNO-modified | 0.2 (±0.1) × $10^5$ | 4.4 (±3.7) × $10^5$ |

The amount of NO released during this 1 h period of irradiation was ~0.08 µmol $cm^{-2}$, corresponding to only <10% of the large reservoir of NO stored within the materials. Since the impinging irradiation dictates the ensuing NO flux (See, FIG. 5), variation of the light source and irradiation intensity may be used to maintain a constant flux of ~20 pmol NO $cm^{-2} s^{-1}$ as long as there is sufficient NO stored within the films.

As the total NO storage of the xerogels ranges from 0.7-1.78 µmol $cm^{-2}$, a theoretical duration of 12.1-24.7 h of NO release at this critical flux may be achieved before the NO reservoir is depleted. As such, the potential of these materials to reduce bacterial adhesion for prolonged time is promising. Overall, these results illustrate the promise of these films as photoantimicrobial NO-releasing surfaces with enhanced NO storage stability at physiological temperatures.

Future development of successful NO-based therapies hinge on the ability to store and release NO in a controlled manner. The RSNO-modified xerogels described herein represent materials that offer such control over release via photoinitiation. Furthermore, the stability of the NO reservoir is enhanced over previous NO release coatings by using sterically-hindered tertiary RSNOs rather than thermally labile primary RSNOs. Exposure to physiological temperature (i.e., 37° C.) does not significantly deplete the NO payload, indicating these films may be suitable for biomedical applications necessitating precisely controlled delivery of NO via light.

Indeed, the generation of NO under ambient room lighting, evident by the loss of NO storage after 30 d of ambient light exposure, suggest these materials may prove useful for common household or hospital surfaces requiring bacterial disinfection. With UV irradiation, even more powerful antibacterial action is envisioned since such irradiation alone also kills microbes. Xerogel materials are amenable to several forms including stand-alone coatings, particles and dopants that allow their application to different substrates and devices. For example, application of tertiary RSNO-modified xerogels to optical fibers would enable NO generation from a point source. Akin to an endoscope, such a device could be positioned at a specific location in the body (e.g., a tumor mass) to facilitate localized NO release when coupled to a light source of appropriate intensity.

Alterations to the impinging irradiation proved to be more critical in achieving varied NO flux as xerogel compositions of different mol % and casting volume exhibited diverse total NO storage but similar NO fluxes under a set irradiation intensity. The ability to deliver a specific NO flux determined solely by the irradiation intensity may allow for the systematic examination of concentration-dependant roles of NO within physiological systems. As NO plays a highly concentration-dependent role in tumor biology and the immune response, such knowledge would be beneficial in the design of future anticancer therapies. As such, the potential of tertiary RSNO-modified xerogels encompass both their application as novel therapeutics as well as tools in elucidating NO's flux-dependant role in physiology.

The synthesis of a tertiary thiol-bearing silane precursor (i.e., NAPTMS) is described to enable enhanced NO storage stability at physiological temperature. The novel silane was co-condensed with a range of alkoxy- and alkylalkoxysilanes (i.e., TMOS, TEOS, MTMOS, and BTMOS) under various synthetic parameters to systematically evaluate the formation of stable xerogel films. Resulting xerogels were subsequently nitrosated to yield tertiary RSNO-modified coatings. Variation in both the concentration of the NAPTMS and xerogel coating thickness provided tunability in the total NO storage of the films (0.87-1.78 µmol Steric hindrance surrounding the nitroso functionality resulted in limited NO release at physiological temperature and allowed photolysis to be used as a more selective trigger for controlled NO delivery. Over a 1 h incubation period at 37° C., average NO fluxes were an order of magnitude larger under irradiation than in the dark for a given composition (e.g., ~23 vs. 3 pmol $cm^{-2}s^{-1}$ for 20% NAPTMS balance TEOS, 30 µL cast in the light and dark, respectively). The utility of such controllable NO-releasing films was demonstrated in their ability to significantly reduce bacterial adhesion (by ~90%) exclusively under irradiation, illustrating the potential of these films as photoantimicrobial surfaces.

We claim:

1. A co-condensed silica sol-gel coating formed from the reaction of the compound of Formula I and at least one backbone alkoxysilane:

Formula I

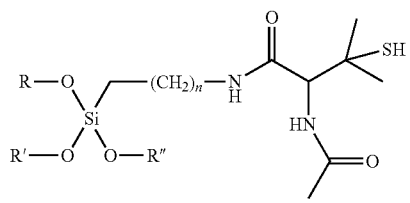

wherein R, R' and R" are each independently alkyl and n is in a range of 0 to 10.

2. The co-condensed silica sol-gel coating of claim 1, wherein compound of Formula I has the following structure:

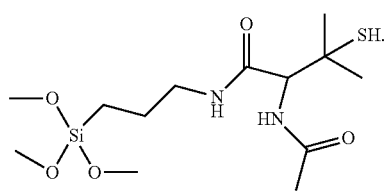 [SMILES: CO[Si](CCCNC(=O)C(NC(C)=O)C(C)(C)S)(OC)OC]

3. The co-condensed silica sol-gel coating of claim 1, wherein the sol-gel coating is a xerogel.

4. The co-condensed silica sol-gel coating of claim 3, wherein the compound of Formula I is present at a concentration in a range of 10 mol% and 30 mol% based on total silane monomer concentration.

5. The co-condensed silica sol-gel coating of claim 3, wherein the backbone alkoxysilane comprises tetraethoxysilane (TEOS) and/or methyltrimethoxysilane (MTMOS).

6. The co-condensed silica sol-gel coating of claim 1, wherein at least some of the thiol groups in the coating have been reacted with a nitrosating agent to form S-nitrosothiol functional groups.

7. A sol-gel coating comprising a tertiary S-nitrosothiol.

8. The sol-gel coating of claim 7, wherein the sol gel coating is a xerogel.

9. The sol-gel coating of claim 8, wherein the NO storage of the xerogel is at a concentration in a range of 0.8 to 2 $\mu mol/cm^2$.

10. A method of forming a nitric oxide (NO)-releasing sol-gel coating comprising:
(a) co-condensing a sol precursor solution comprising at least one backbone alkoxysilane and at least one tertiary thiol alkoxysilane in a solvent to form a sol;
(b) coating a substrate with the sol;
(c) optionally, drying the sol to form the sol-gel coating; and
(d) contacting the sol-gel coating with a nitrosating agent.

11. The method of claim 10, wherein the sol-gel coating is a xerogel.

12. The method of claim 10, wherein the at least one tertiary thiol alkoxysilane has the structure of (OR)(OR')(OR")Si($R^x$), wherein R, R' and R" are each independently H, alkyl or substituted alkyl and $R^x$ is functional group that comprises a tertiary thiol group.

13. The method of claim 8, wherein the tertiary thiol alkoxysilane has the structure:

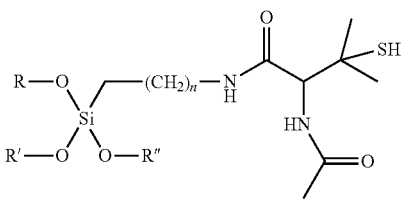

wherein R, R' and R" are each independently alkyl and n is in a range of 0 to 10.

14. The method of claim 13, wherein the tertiary thiol alkoxysilane has the structure

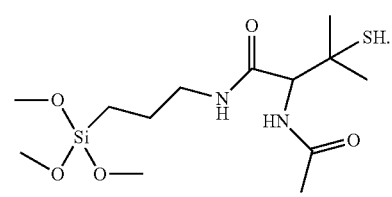 [SMILES: CO[Si](CCCNC(=O)C(NC(C)=O)C(C)(C)S)(OC)OC]

15. The method of claim 10, wherein the at least one backbone alkoxysilane comprises TEOS and/or MTMOS.

16. The method of claim 10, wherein the sol precursor solution further comprises an acid catalyst.

17. The method of claim 16, wherein the acid catalyst is present in the sol precursor solution at a concentration in a range of 0.025M to 0.075M.

18. The method of claim 10, wherein the tertiary thiol alkoxysilane is present at a concentration of less than 40 mol % based on the total alkoxysilane concentration.

19. A method of reducing or eliminating bacterial adhesion to a substrate comprising
(a) coating the substrate with the co-condensed silica_sol-gel coating of claim 1;
(b) exposing the substrate to bacteria; and
(c) irradiating the substrate to release nitric oxide, which reduces or eliminates bacterial adhesion to the substrate.

20. The method of claim 19, wherein the sol-gel coating is a xerogel.

* * * * *

UNITED STATES PATENT AND TRADEMARK OFFICE
CERTIFICATE OF CORRECTION

PATENT NO.         : 8,981,139 B2                              Page 1 of 1
APPLICATION NO.    : 13/975995
DATED              : March 17, 2015
INVENTOR(S)        : Schoenfisch et al.

It is certified that error appears in the above-identified patent and that said Letters Patent is hereby corrected as shown below:

On the Title Page:
Item 54, Column 1, Lines 1-3 Title:
    Please correct "TERTIARY $S$-NITROSOTHIOL-MODIFIED NITRIC_OXIDE-RELEASING XEROGELS AND METHODS OF USING THE SAME"

to read -- TERTIARY $S$-NITROSOTHIOL-MODIFIED NITRIC OXIDE-RELEASING XEROGELS AND METHODS OF USING THE SAME --

In the Specification:
Column 2, Line 50: Please correct "(30 cast)" to read -- (30μL cast) --

Column 14, Line 3: Please correct "150 μmol" to read -- 150 pmol --

Column 14, Line 4: Please correct "120 μmol" to read -- 120 pmol --

Column 16, Line 13: Please correct "(Bucks, Switzerland)." to read -- (Buchs, Switzerland). --

Column 18, Line 13: Please correct "of 0.6 in)." to read -- of 0.6 m). --

Column 20, Line 12: Please correct "(1054 μL)" to read -- (1050μL) --

Column 21, Line 61: Please correct "(330-350 $n_o \rightarrow \pi^*$)" to read -- (330-350nm; $n_O \rightarrow \pi^*$) --

Column 28, Line 59: Please correct "(0.87-1.78 μmol Steric hindrance"
              to read -- (0.87-1.78 μmol cm$^{-2}$). Steric hindrance --

Signed and Sealed this
Twenty-fourth Day of November, 2015

Michelle K. Lee
*Director of the United States Patent and Trademark Office*